(12) United States Patent
Ichiyanagi et al.

(10) Patent No.: US 11,111,517 B2
(45) Date of Patent: Sep. 7, 2021

(54) HBA1C DEHYDROGENASE

(71) Applicant: Kikkoman Corporation, Noda (JP)

(72) Inventors: Atsushi Ichiyanagi, Chiba (JP); Yosuke Masakari, Chiba (JP)

(73) Assignee: Kikkoman Corporation, Chiba (JP)

( * ) Notice: Subject to any disclaimer, the term of this patent is extended or adjusted under 35 U.S.C. 154(b) by 177 days.

(21) Appl. No.: 16/094,924

(22) PCT Filed: Apr. 21, 2017

(86) PCT No.: PCT/JP2017/016058
§ 371 (c)(1),
(2) Date: Oct. 19, 2018

(87) PCT Pub. No.: WO2017/183717
PCT Pub. Date: Oct. 26, 2017

(65) Prior Publication Data
US 2019/0119715 A1    Apr. 25, 2019

(30) Foreign Application Priority Data

Apr. 22, 2016  (JP) .............................. JP2016-086592

(51) Int. Cl.
*C12Q 1/32*        (2006.01)
*C12N 15/09*       (2006.01)
(Continued)

(52) U.S. Cl.
CPC .............. *C12Q 1/006* (2013.01); *C12M 1/40* (2013.01); *C12N 9/0036* (2013.01); *C12N 15/09* (2013.01);
(Continued)

(58) Field of Classification Search
CPC .......... C12Q 1/006; C12Q 1/32; C12Q 1/001; C12N 15/09; C12N 9/0036; C12N 9/88;
(Continued)

(56) References Cited

U.S. PATENT DOCUMENTS 5,370,990 A    12/1994  Staniford et al.
7,070,948 B1   7/2006   Sakaue et al.
(Continued)

FOREIGN PATENT DOCUMENTS

EP    2287295 A1     2/2011
JP    05-033997 B2   5/1993
(Continued)

OTHER PUBLICATIONS

International Search Report dated Jul. 18, 2017, in PCT/JP2017/016058.
(Continued)

*Primary Examiner* — Jennifer Wecker
*Assistant Examiner* — Michael Paul Shimek
(74) *Attorney, Agent, or Firm* — Foley & Lardner LLP

(57) ABSTRACT

This invention provides an HbA1c dehydrogenase that is capable of directly acting on hemoglobin A1c and is less likely to be influenced by oxygen concentration and a method for measurement and a kit of assay reagents using such HbA1c dehydrogenase. The HbA1c dehydrogenase having dehydrogenase activity and capable of directly acting on HbA1c is obtained by substitution of one or more amino acid residues at positions corresponding to positions 280, 269, 54, 241, and 267 of the amadoriase that is capable of directly acting on hemoglobin A1c and is derived from, for example, the genus *Coniochaeta*. This invention also provides a method for measurement of HbA1c, a kit of assay reagents, and a sensor using such HbA1c dehydrogenase. Such HbA1c dehydrogenase is capable of directly acting on hemoglobin A1c and has lowered oxidase activity and/or enhanced dehydrogenase activity. This not only eliminates the need for treatment of hemoglobin A1c with a protease but also enables the use of an electron mediator in the measurement of HbA1c, thereby reducing effects due to
(Continued)

oxygen concentration, and enables HbA1c measured with high sensitivity.

2 Claims, 18 Drawing Sheets

Specification includes a Sequence Listing.

(51) Int. Cl.
| | | |
|---|---|---|
| *C12M 1/40* | (2006.01) | |
| *G01N 33/483* | (2006.01) | |
| *G01N 27/416* | (2006.01) | |
| *G01N 33/49* | (2006.01) | |
| *G01N 27/327* | (2006.01) | |
| *C12N 9/88* | (2006.01) | |
| *C12Q 1/00* | (2006.01) | |
| *G01N 33/72* | (2006.01) | |
| *C12N 9/02* | (2006.01) | |

(52) U.S. Cl.
CPC ............ *C12Q 1/32* (2013.01); *G01N 27/327* (2013.01); *G01N 27/3271* (2013.01); *G01N 27/416* (2013.01); *G01N 33/483* (2013.01); *G01N 33/49* (2013.01); *G01N 33/723* (2013.01); *C12N 9/88* (2013.01)

(58) Field of Classification Search
CPC .. C12N 9/0004; G01N 33/723; G01N 33/483; G01N 27/416; G01N 33/49; G01N 27/327; G01N 27/3271; G01N 33/72; G01N 2333/805; C12M 1/40
See application file for complete search history.

(56) References Cited

U.S. PATENT DOCUMENTS

| | | | |
|---|---|---|---|
| 2006/0240501 A1 | 10/2006 | Ebinuma | |
| 2008/0113381 A1 | 5/2008 | Matsuoka et al. | |
| 2008/0233605 A1 | 9/2008 | Taniguchi et al. | |
| 2011/0003361 A1 | 1/2011 | Kurosawa et al. | |
| 2011/0195444 A1 | 8/2011 | Hirao et al. | |
| 2014/0234886 A1 | 8/2014 | Aisaka et al. | |
| 2014/0356928 A1 | 12/2014 | Masakari et al. | |
| 2015/0118700 A1 | 4/2015 | Ichiyanagi et al. | |
| 2016/0123999 A1* | 5/2016 | Ogawa ..................... | C12Q 1/26 435/28 |
| 2016/0138073 A1 | 5/2016 | Ogawa | |
| 2016/0251695 A1 | 9/2016 | Masakari et al. | |
| 2017/0355967 A1 | 12/2017 | Masakari et al. | |

FOREIGN PATENT DOCUMENTS

| | | |
|---|---|---|
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2008076143 A * | 4/2008 |
| JP | 2010-035469 A | 2/2010 |
| JP | 2010-057474 A | 3/2010 |
| JP | 2011-229526 A | 11/2011 |
| JP | 2013-500729 A | 1/2013 |
| WO | WO 97/13872 A1 | 4/1997 |
| WO | WO 2004/038034 A1 | 5/2004 |
| WO | WO 2004/104203 A1 | 12/2004 |
| WO | WO 2005/049857 A1 | 6/2005 |
| WO | WO 2008/108385 A1 | 9/2008 |
| WO | WO 2010/041419 A1 | 4/2010 |
| WO | WO 2010/041715 A1 | 4/2010 |
| WO | WO 2011/015325 A1 | 2/2011 |
| WO | WO 2011/015326 A2 | 2/2011 |
| WO | WO 2013/100006 A1 | 7/2013 |
| WO | WO 2013/162035 A1 | 10/2013 |
| WO | WO 2015/005257 A1 | 1/2015 |
| WO | WO 2015/005258 A1 | 1/2015 |
| WO | WO 2015/060429 A1 | 4/2015 |
| WO | WO 2016/063984 A1 | 4/2016 |

OTHER PUBLICATIONS

Ferri et al., "Cloning and Expression of Fructosyl-amine Oxidase from Marine Yeast *Pichia* Species N1-1," Mar. Biotechnol., 2004, 6:625-632.

Ferri et al., "Isolation and characterization of a fructosyl-amine oxidase from an *Arthrobacter* sp.," Biotechnology Letters, 2005, 27:27-32.

Fujiwara et al., "Alteration of Substrate Specificity of Fructosyl-Amino Acid Oxidase from *Ulocladium* sp. JS-103," Journal of Bioscience and Bioengineering, 2006, 102(3):241-243.

Fujiwara et al., "Alteration of substrate specificity of fructosyl-amino acid oxidase from Fusarium oxysporum," Appl. Microbiol. Biotechnol., 2007, 74:813-819.

Hirokawa et al., "Molecular cloning and expression of novel fructosyl peptide oxidases and their application for the measurement of glycated protein," Biochemical and Biophysical Research Communications, 2003, 311:104-111.

Hirokawa et al., "Recombinant Agrobacterium AgaE-like Protein with Fructosyl Amino Acid Oxidase Activity," Biosci. Biotechnol. Biochem., 2002, 66(11):2323-2329.

Jeong et al., "The veA gene is necessary for the inducible expression by fructosyl amines of the Aspergillus nidulans faoA gene encoding fructosyl amino acid oxidase (amadoriase, EC 1.5.3)," Arch. Microbiol., 2002, 178:344-350.

Jeppsson et al., "Approved IFCC Reference Method for the Measurement of HbA$_{1c}$ in Human Blood," Clin. Chem. Lab. Med., 2002, 40(1):78-89.

Kim et al., "Motif-Based Search for a Novel Fructosyl Peptide Oxidase from Genome Databases," Biotechnology and Bioengineering, Jun. 15, 2010, 106(3):358-366.

Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.

Sakai et al., "Purification and Properties of Fructosyl Lysine Oxidase from Fusarium oxysporum S-1F4," Biosci. Biotech. Biochem., 1995, 59(3):487-491.

Yoshida et al., "Primary structures of fungal fructosyl amino acid oxidases and their application to the measurement of glycated proteins," Eur. J. Biochem., 1996, 242:499-505.

Supplementary European Search Report dated Sep. 2, 2019, in EP 17786054.1.

Kameya et al., "Advancing the Development of Glycated Protein Biosensing Technology: Next-Generation Sensing Molecules," Journal of Diabetes Science and Technology, Mar. 17, 2015, 9(2):183-191.

\* cited by examiner

Sequence alignment (positions shown at start and end of each row):

```
Co  399  EEMAYQ WRPG-G DDALKS RRAAPP AKDLAD MPGWKHD -PKL--  ------ -----  437
Et  399  QEMAGA WRWRPG-GDDAL RSRRGA AAPAKD LAEMPGWKHDAHL- ----- ----- -  437
Py  397  ADLAHA WRWRPG QGDDAL QSRR-A AAPAKD LADMPGWNHD-ES PRAKL ----- -  440
Ar  400  DDLAEA WRWRPG -GDDAL KKS-RR GAAAPA KDLADMPGWKHD-E SPRAK L---- -  449
Cc  397  DDLAEA WRWRPG SGGDDA LLLRR- RRAAPA KDLADMPGWKHD-D VKSKL ----- -  440
Nv  399  EDLAES WRWRPG QGGDDA LARRSR RRSAAP AKDLADLPGWKHD-Q DSGNA TSGTS SE 441
Cn  399  DDLAFK DAWRWR PGGGGD DAPKLL RKKSRR RRAAPAKDLADMPGWNHD-DVKSRL--  448
Pn  395  SVSVFK DAWRWR PGSGGD DALLLK KS-SRR RRAAPAKDLADMPGWNHD-EPSDDM DVKDVA 437
An  399  DDDLAH AWRWRP GSGGDD ALLRP- LLKRKS SRRRRR AAPAKD LADMPGWNHD -AKM  438
En  399  QDLAGA WRWRPG -GDDAL ALLKSR KSS-KR RRAAPA KDLAEMP GWRNEAKM ---  438
Ul  397  -----  -----  -----  -----  -----  -----  -----  -----  ---  441
Pj  399  QDLAGA WRWRPG -GDDAL AL-KS KKSRR SAAAPA KDLAEMP GWKHDA KL---  437
```

Right column positions: 437, 437, 440, 449, 440, 441, 448, 437, 438, 438, 441, 437

Co  437 (SEQ ID NO: 1)
Et  437 (SEQ ID NO: 3)
Py  440 (SEQ ID NO: 4)
Ar  452 (SEQ ID NO: 5)
Cc  440 (SEQ ID NO: 6)
Nv  441 (SEQ ID NO: 7)
Cn  477 VSLASVKIGENIGEKVVEDGARVGVKVLA (SEQ ID NO: 8)
Pn  437 (SEQ ID NO: 9)
An  438 (SEQ ID NO: 10)
En  438 (SEQ ID NO: 11)
Ul  441 HKL (SEQ ID NO: 12)
Pj  437 (SEQ ID NO: 13)

| | | | | | | | | | | | | | | |
|---|---|---|---|---|---|---|---|---|---|---|---|---|---|---|
| Co | 92 | TGRMDCEHTPEGIEDLKKQYQALHDAGAGLEKTHAWLDNEDEILSKMPLL | 141 |
| Et | 92 | VGM-DDCSSSKEGIENLRRKYQTLLDAGIGLEKTNVWLESEDEILAKAPNF | 141 |
| Py | 92 | TGRRDDCAHGEKGINAALKRQAYQTLLDANAGLEKTNEWLDSEDAILAKMPLL | 141 |
| Ar | 92 | TGRRDDCEGTEKGIAADLRQAYQALLDADVGLEKTTEWLDSEDAILAKMPLL | 141 |
| Cc | 92 | TGRRDDCAHGEESAEGVEGLRREYQKLLVEAGVGLEETHEWLDSEEAILEKAPLL | 141 |
| Nv | 92 | TGRRDDCAHTPESIASLRKSGYQALVDA-LLDAGIGLEKTHHWLSTEDEILARAPLL | 141 |
| Cn | 92 | VGM-DDCAHGEKDIADLRKKYQSLLDAGIGLEKTNFMLESEDEILKRMPLL | 139 |
| Ph | 92 | VGQMDDCAHGSSTEEGLRKLRMRYQALLDAGIGLEKTNFLLESEDEILAKAPLL | 140 |
| An | 91 | TGRRDDCAHGEKGLASLRRKHQDLIDANAGLEKTNWLESEDDILAKAPHF | 140 |
| En | 91 | VGM-LDDCSSSQEGLASLDRLG-IRVRVRPGEDP---DVSEVTKPEHFRQLAPA-VLK | 141 |
| Uj | 92 | VGQMLDDCSSSQEGLDRLG-VRVRVRPGEDP---NLVELTRPEQFRKLAPEG-VLQ | 141 |
| Pj | 92 | TGR-LDDCAHGSSSAGLERLG-VEDE-IGDD-ID---DVAELTRPEQFRKTMPEG-ILT | 139 |
| Ao2 | 94 | TGGALDDCSSSAGLVEDE-IGDD-ID---QYTPLNTAEDFRKTMPEG-ILT | 140 |
| Af2 | 94 | TGGSVDDCSSSAGLVEHE-IDSSDA---EF-IKLNTAEDFRKTMPPG-ILT | 139 |
| At | 94 | TGGSV----DDCVAGSTPKSLIKQLVEHE-IDSSDA---EF-IKLNTAEDFRRTMPPGV-LT | 143 |
| Fo | 97 | HGGA---DDVAGSTPALSLIKH-IQEHE-IRKDEVEPSET---NFVKLETAEDFREYLP---LT | 145 |
| Ao1 | 99 | VGFI---LAASSDAPLLHDKH-IDH-IRKDEVEPSET---NFVKLETAEDFREYLPI--LK | 145 |
| Af1 | 99 | VGFI---LAASSDAPLLHDKEYYEELQKNGLRNYRY-ISTPEEFREYLPI--LK | 135 |
| Pi | 88 | VGFI---YAATGKEQRESIDYRYEYLLGRK-DKVVKLNSVEDYEKYVPNKEGS | 134 |
| Dh | 86 | TGI-I---YAATGKEQRESIDYRYEYLLGRK-DKVVKLNSVEDYEKYVPNKEGS | 134 |

Fig. 2-4

| | | | | | | | |
|---|---|---|---|---|---|---|---|
| Co | 142 | QRDQIQG- | -WKAIWSQDG- | -GWLAAAKA-INAIGQFLKERGVKFFGFGGAGSF | 188 |
| Et | 142 | TREQVKG- | -WKGLFCTDG- | -GWLAAAKA-INAIG-FLQDLRKELLQDKGVKFFGFGGAGTF | 188 |
| Py | 142 | SREQIKG- | -WKAVFSRDG- | -GWLAAGKA-INAIGEYLRRAQQRVKFFGFGGAGSF | 188 |
| Ar | 142 | ERDQIKG- | -WKAIFSQDG- | -GWLAAAKA-INAIGEEYLRKRAQQRVNFFGFGGAGAF | 188 |
| Cc | 142 | DREQIKG- | -WKAVYSQDG- | -GWLAAAKA-INAIGGEYLRDAQRQVKRFGFGGAGSF | 188 |
| Nv | 142 | QREEIEG- | -WKAIWSEEG- | -GWLAAAKA-INSIGQVLKEKGVTFFGFGGAGSF | 188 |
| Cn | 142 | DRKQIKG- | -WKAIYSEDG- | -GWLAAAKA-INAIGGEYLRDKEQGVRFFGFGGAGSF | 186 |
| Pn | 140 | SRDQIKG- | -WKAI-FSKDG- | -GWLAAAKA-INAIGQFLKEKGVKFFGFGGAGSF | 187 |
| An | 141 | TQEQIKG- | -WKGLFCGDG- | -GWLAAAKA-INAIGQFLRDQQGVKFFGFGGAGSF | 187 |
| En | 141 | TREQIKG- | -WKGLFCGDG- | -GWLAAAKA-INAIG-TIREAEKLGVKFFGFGGEAGTF | 188 |
| Ul | 142 | NRDQIKG- | -WKAVFSEDG- | -GWLAAAKA-INAIAAAREAQRMGVRFFGFGGAGSF | 188 |
| Pj | 142 | TREQIKG- | -WKGLFCGDG- | -GWLAAAHA-LVAAAARLGVKFFVTG--TQGR | 184 |
| Ao2 | 140 | GNFPG-- | -WRGYHIRSNA | GWAHAAAHA-LVAAAREAFEESRLGVRFFVAGSPQGR | 186 |
| Af2 | 141 | GDFPPG-- | -WKGYFARSGA | GWAAAAHARRNALVKAAMFSAYTEAKRLGVKFTFPEGK | 185 |
| At | 140 | GNFPG-- | -WRGYHIRSNA | GWVHAAAHARRNALVAAAREAKRLGVTFTFTGSPEGD | 189 |
| Fo | 144 | GNFPG-- | -WKGFYKPTGSG | GWIHAKKAMFSAFNEAKRLGVEFFVTGSPEGN | 191 |
| Ao1 | 146 | GNFPG-- | -WKGWLNKTGAG | GWI--HAKKAMISAFNEAKRLGVEFFVTGSPEGN | 191 |
| Af1 | 146 | GDFPG-- | -WKGWLHKSGAG | GWI--HAKKAMFSLKSAYEECKRLGVEFFVFG--DDGE | 180 |
| Pj | 136 | GPLPN-- | -WRGYVLDGDNG | WLHARDSLKSAYEECKRLGVEFFVFG--DDGE | 180 |
| Dh | 135 | KSYPNKFQKW | YGGYYQEKNC | GWAFARLALENCVEECRKLGAKFVIDSAEEL | 184 |

Fig. 2-5

| | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Co | 189 | K Q P L F D - D E G T T C I G V E T A D G T K Y Y A D K V V L A A G A W S P T L V D L E D Q C C S K | 237 |
| Et | 189 | Q Q P L F A - A D G K T C I G L E T T D G T K Y F A D K V V L A A G A W S P T L V D L E D Q C V S K | 237 |
| Py | 189 | Q Q Q P L L A - E G - - P D G S T C I G V E T V D G T R Y Y A D K V V L A A G A W S P A L V D L E D Q C C S K | 235 |
| Ar | 189 | K K K P L F A - D D G T T C I G V E T V D G T K Y Y G D K V V L A A G A W S P T L V D L E E Q C V S K | 237 |
| Cc | 189 | K K K P L F A - E G - - D D G T T C I G V E T V D G T R Y Y A D K V V L A A G A W S P T L V D L E D Q C C S K | 235 |
| Nv | 189 | K K K P L F A - E D G T T C I G V E T V D G T Q Y F A D K V V L A A G A W S P T L V E L H E D Q C V S K | 237 |
| Cn | 189 | K A P L L A - A E - - - V C I G V E T V D G T Q Y Y A D K V V L A A G A W S S T L V D L E E Q C C S K | 233 |
| Pn | 187 | K K K P L F A D A H E K T C I G V E T V D G T R K Y Y A D K V V L A A G A W S S T L V D L E E Q C V S K | 237 |
| An | 188 | K K K P L F A D A D A D E K T C - - V C I G V E T V D G T K Y Y A D K V V L A A G A W S P A L V D L Q D D Q C C S K | 235 |
| En | 188 | K Q P L F A - P D G A T C S G V E T A D G T K Y F A D K V V L C A G A N A A Q F L L D F K D Q L R P T | 237 |
| Ui | 189 | K R P L F A - - F - - E N N D V C C V G A V T G D D G K I W R A E Q T V L C C A G A S A G Q F L L D F K N Q L R P T | 232 |
| Pj | 189 | V I T L - I F - - - E N N D V K G A V T A D D G K I W R A E R T F I I C A G A A A E F F L L D F E N Q I Q P T | 234 |
| Ao2 | 185 | V V T L I F - - - E N N D V K G A V T A D D G K E H R A D H T I L C A G A S A E F L L D F K K D Q L R P T | 233 |
| Af2 | 187 | V I T L - I F - - - E D G D V R G A K T A D D G K E H R A D R T I L S A G A G S A E F L L D F K K Q L R P T | 237 |
| At | 186 | V E S L I F - - - E N G D V R G A V T A D D G T V H R A D H T - - L S A G A G S D R L L L D F K K Q L E G K | 239 |
| Fo | 190 | V V S L Y - - - E D G D V V G A R T A D D G R V H K A H R T - - L S A G A G S D S L L L N F Q R Q L R P T | 239 |
| Ao1 | 192 | V V S L V Y - - E N G K L T G I R A R S G A I F S A Q K Y V L I S S G A N A V T L L L N F Q R Q L E G K | 228 |
| Af1 | 192 | I V E L L N - - - - - - - - - - G I R A R S G A I F S A Q K Y V L I S S G A N A V T L L L N F Q R Q L E G K | 228 |
| Pi | 181 | L F S - - - - E D G A C V G V H T S N G N I I E A D R T I I C A G A N S F K F L N F E Q Q L L A K | 229 |
| Dh | 185 | | |

| | Start | Sequence | End |
|---|---|---|---|
| Co | 287 | SRF-KEHQPYGAPSPKRISVPRSHAKKHPTDTYPDDASEVSIKKATATFLPR | 335 |
| Et | 287 | SRF-KLHQPYGAASPKMISVPRSHAKKHPTDTYPDDASEVTIRKKA--VARFLPE | 335 |
| Py | 285 | TRF-KKEQHQSYGAPFGARAPKRVSVPRSHAKKHPTDTYPDDASEQSIKKRAAAFLPQ | 333 |
| Ar | 287 | TRF-KQHQPYGAPAPTRVSVPRSHAAKHPTDTYPDDASEKSIRRKA--VATFLPR | 336 |
| Cc | 285 | TRF-KQHQPYGAKAPAPKRISFPRSHAKKHPTDTYPDDASEESIKRRA--VSTFLPQ | 333 |
| Nv | 287 | TRF-KQHQPYGAPAPKPHISVPRSHAKKHPTDTYPDESDDASEVTIKRRA--SATFMPR | 335 |
| Cn | 287 | THF-KMHQPYGASSTKAPKRISVPRSHAKKHPTDTYPDDASEVTIKKKA--ATFNRFLPQ | 331 |
| Pn | 283 | THF-KMHQPFGAKAPAPKRPISVPRSHAKKHPTDTYPDHASEVSIKRRA--ATFARFLPR | 335 |
| An | 287 | TRF-KMHQPYGSSPAPKVPKLISVPRSHAKKHPTDTYPDHASEEESIRRRA--VSETMPR | 335 |
| En | 287 | SRF-KLHQPYGASAPKRISVPRSHAAKHPTDTYPDSSEET-IRRRA--LSETMPQ | 333 |
| Uf | 285 | - - - - - - - - - - - - - - - - - GHLTSLPFFEKTQ-VPPTEARVRALLLSLLKETMPQ | 335 |
| Pj | 287 | - - - - - - - - - - - - - - - - - GTMMS-IPFFEKTQ-VPPTEAEMRARVRKLLKDTMPH | 321 |
| Ao2 | 283 | TNMVKSAD - - - - - - - - - - - - GRVRS-IPFFEKTQ-VPPT-LEAEERRMKQFLRDFLIMPH | 323 |
| Af2 | 285 | TNMVQSAD - - - - - - - - - - - - KYPQS-IPFAKHQ-IPL-LEAEARARDFLRQYLKETMPQ | 322 |
| At | 284 | TNMTTGAD - - - - - - - - - - - - GEVRS-IPFAKHQ-IPL-LEAEARALEIRQMRAFLRQVFPE | 327 |
| Fo | 288 | CNWVEKPG-S - - - - - - - - - - - GQEKS-VPFAKHG- | 330 |
| Ao1 | 290 | CNFVPDPKHG - - - - - - - - - - SIPLYRME-IPL-LESALE | 330 |
| Af1 | 290 | CNFLPDPNRP - - - - - - - - - - - - - - - - - - | 278 |
| Pi | 278 | THTNESGE - - - - - - - - - - - - - - - - - - - - - - - - | 312 |
| Dh | 279 | VNIVNEDS - - - - - - - - - - - - -VPSFKDS - - - - - - - - - | 312 |

| | | | | | | | | | | | | |
|---|---|---|---|---|---|---|---|---|---|---|---|---|
| Co | 386 | GKY | VVEL | IEG- | --- | RLPEEM | AYQWRWR | PG- | GDALK | ----- | SRRAAPPKD | LAD | 427 |
| Et | 386 | GKH | VVEL | LEG- | --- | SLSQEM | AGAWRWR | PG- | GDALR | ----- | SRRGAPAKD | LAE | 427 |
| Py | 384 | GKH | VVEL | IEG- | --- | TLAADL | AHALAWR | PG- | IGDALQ | ----- | SRRAAPAKD | LAD | 426 |
| Ar | 387 | GKH | VVEL | LEG- | --- | RLADDL | AQAWRWR | PG- | QGDALK | ----- | SRRAAPAKD | LAD | 429 |
| Cc | 384 | GKH | VVEL | VEG- | --- | RLADDL | AEAWRWR | PG- | TGDALK | ----- | S-RRAAPAKD | LAD | 426 |
| Nv | 386 | GKH | VVEL | LEG- | --- | TLAEDL | AESWRWR | PG- | QGDALK | ----- | SRRAAPAKD | LAD | 428 |
| Cn | 386 | GKH | VVEL | LEG- | --- | RLADDL | AHAWRWR | PG- | SGDDPL | I--- | SRRAAPAKD | LAD | 428 |
| Pn | 382 | GKH | VVEL | IEG- | --- | RLESVF | KDAWRWR | PG- | SGDALK | ----- | SRRSAPAKD | LAD | 424 |
| An | 386 | GKH | VVEL | LEE- | --- | RLESVF | KDAWRWR | PG- | SGDALK | ----- | SRRAAPAKD | LAD | 428 |
| En | 386 | GKH | VVEL | LEG- | --- | TLADDL | AHAWRWR | PG- | TGDALK | ----- | SRRAAPARD | LAD | 428 |
| Ul | 384 | GKH | VVEL | IEG- | --- | RLPQDL | AGAWRWR | PG- | GDALK- | ---- | SKRSAPAKD | LAE | 426 |
| Pj | 386 | GKN | L--- | VDA | IED- | KVPEKV | HKLTRWS | PDI | AVDRKWR | DTLGR | FGGPNRV | MDD | 418 |
| Ao2 | 372 | GGN | L--- | VDA | MEG- | KVPQKI | HELI-KW | NPD | IAANRNWR | DTLGR | FGGPNRV | MDD | 420 |
| Af2 | 374 | GGS | I--- | ADA | MED- | KTPAKI | HKLI-RW | SPE | AINRNWG | DRLGR | FGGPNRV | MDD | 419 |
| At | 373 | GKF | I--- | ADA | MEG- | TLEERF | AKYWRWR | PEK | FTEFWG | KDPLDR | FGADDK-I | MDD | 424 |
| Fo | 378 | GGF | I--- | ADA | LEG- | NLQKEL | KHALRWR | PEA | AQRDWK | DTQNR | FGGPNKV | MDD | 427 |
| Ao1 | 381 | GGF | I--- | ADA | LES- | KLQKEV | KDI-VRW | PET | AVDRDWR | ATQNR | FGGPDRY | RVAD | 427 |
| Af1 | 381 | GKY | VVTK | GDK | GDKG | LDPEDK | ECWKWR | PET | WDKRG- | --- | QVRWGGRYRV | AD | 408 |
| Pi | 363 | GKY | VSKV | VTK | GDKG | LDPEDK | ECWKWR | PET | WDKRG- | --- | QVRWGGRY | RVAD | 408 |
| Dh | 363 | GKY | I-SQ | VAL | KGENS | LDKDKK | ELWRWR | PDM | GKKRDL | KDLQGR | YGGSNEV | KD | 412 |

Fig. 2-10

| | | | | |
|---|---|---|---|---|
| Co | 428 | MPGWKHDPKL---------------------------- | 437 | (SEQ ID NO: 1) |
| Et | 428 | MPGWKHDAHL---------------------------- | 437 | (SEQ ID NO: 3) |
| Py | 427 | MPGWNHD-ESPRAKL------------------------ | 440 | (SEQ ID NO: 4) |
| Ar | 430 | MPGWNHDGDSGNATSGTSSEHKL---------------- | 452 | (SEQ ID NO: 5) |
| Cc | 427 | MPGWKHD-DVVKSKL------------------------ | 440 | (SEQ ID NO: 6) |
| Nv | 429 | MPGWKHDQDSESR-------------------------- | 441 | (SEQ ID NO: 7) |
| Cn | 429 | LPGWNHDEPSDDDMDVKDVAVSLASVKIGENIGEKVVEDGARVGVKVLA | 477 | (SEQ ID NO: 8) |
| Pn | 425 | MPGWNHD--KPRANL------------------------ | 437 | (SEQ ID NO: 9) |
| An | 429 | MPGWRNEAKM----------------------------- | 438 | (SEQ ID NO: 10) |
| En | 429 | MPGWRNEAKM----------------------------- | 438 | (SEQ ID NO: 11) |
| Ul | 427 | MPGWNHDGEAPRAKL------------------------ | 441 | (SEQ ID NO: 12) |
| Pl | 428 | MPGWKHDAKL----------------------------- | 437 | (SEQ ID NO: 13) |
| Ao2 | 419 | FH--DVKEWTNVQNKDTAKL------------------- | 436 | (SEQ ID NO: 19) |
| Af2 | 421 | FH--DVKEWTNVQYRDISKL------------------- | 438 | (SEQ ID NO: 20) |
| At | 420 | FN--EVKEWTNVTQRDISKL------------------- | 437 | (SEQ ID NO: 21) |
| Fo | 425 | LPKSDVEGWTNIKNDI----------------------- | 440 | (SEQ ID NO: 22) |
| Ao1 | 428 | FQKVGENEWTKIGDKSRL--------------------- | 445 | (SEQ ID NO: 23) |
| Af1 | 428 | FQQVGEDQWTKIGESRGP--------------------- | 445 | (SEQ ID NO: 24) |
| Pi | 409 | LN--EIEEWVSVENPTPHKLE------------------ | 427 | (SEQ ID NO: 25) |
| Dh | 413 | LK--NVKQWSNGKSHL----------------------- | 426 | (SEQ ID NO: 26) |

SEQUENCE LISTING

```
<160> NUMBER OF SEQ ID NOS: 37

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
```

```
1               5                   10                  15
Gly Thr Ile Gly Ser Ser Thr Ala Leu His Leu Val Arg Ser Gly Tyr
                20                  25                  30
Ala Pro Ala Asn Ile Thr Val Leu Asp Thr Phe Glu Ile Pro Ser Ala
                35                  40                  45
Gln Ser Ala Gly His Asp Leu Asn Lys Ile Met Gly Ile Arg Leu Arg
 50                  55                  60
Asn Lys Val Asp Leu Gln Met Ser Leu Glu Ala Arg Gln Met Trp Lys
 65                  70                  75                  80
Glu Asp Glu Leu Phe Gln Pro Phe Phe His Asn Thr Gly Arg Met Asp
                85                  90                  95
Cys Glu His Thr Pro Glu Gly Ile Glu Asp Leu Lys Lys Gln Tyr Gln
                100                 105                 110
Ala Leu His Asp Ala Gly Ala Gly Leu Glu Lys Thr His Ala Trp Leu
                115                 120                 125
Asp Asn Glu Asp Glu Ile Leu Ser Lys Met Pro Leu Leu Gln Arg Asp
                130                 135                 140
Gln Ile Gln Gly Trp Lys Ala Ile Trp Ser Gln Asp Gly Gly Trp Leu
145                 150                 155                 160
Ala Ala Ala Lys Ala Ile Asn Ala Ile Gly Gln Phe Leu Lys Glu Arg
                165                 170                 175
Gly Val Lys Phe Gly Phe Gly Gly Ala Gly Ser Phe Lys Gln Pro Leu
                180                 185                 190
Phe Asp Asp Glu Gly Thr Thr Cys Ile Gly Val Glu Thr Ala Asp Gly
                195                 200                 205
Thr Lys Tyr Tyr Ala Asp Lys Val Val Leu Ala Ala Gly Ala Trp Ser
210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Glu Tyr Lys Gly
                245                 250                 255
Val Pro Val Val Tyr Asn Gly Glu Phe Gly Phe Phe Phe Glu Pro Asp
                260                 265                 270
Glu Phe Gly Val Ile Lys Val Cys Asp Glu Phe Pro Gly Phe Ser Arg
                275                 280                 285
Phe Lys Glu His Gln Pro Tyr Gly Ala Pro Ser Pro Lys Arg Ile Ser
                290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
                340                 345                 350
Ala Asp Ala Ala Leu Leu Met Cys Glu His Pro Lys Trp Lys Asn Phe
                355                 360                 365
Ile Leu Ala Thr Gly Asp Ser Gly His Ser Phe Lys Ile Leu Pro Asn
                370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
                420                 425                 430
```

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atacgactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540
ggattcggcg cgctggatc cttcaagcaa cccctttcg acgatgaagg cacaacttgc       600
attggcgttg agacgcaga tggtaccaaa tattacgctg acaaggtggt cttagcagct      660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta ccagacgca      960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 3
<211> LENGTH: 437
<212> TYPE: PRT
<213> ORGANISM: Eupenicillium terrenum

<400> SEQUENCE: 3

Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
                20                  25                  30

Thr Pro Ser Asn Ile Thr Val Leu Asp Val Tyr Lys Thr Pro Ser Leu
            35                  40                  45

Gln Ser Ala Gly His Asp Leu Asn Lys Ile Met Gly Ile Arg Leu Arg
        50                  55                  60

Asn Gly Pro Asp Leu Gln Leu Ser Leu Glu Ser Leu Asp Met Trp Gln
65                  70                  75                  80

```
Asn Asp Glu Leu Phe Lys Pro Phe Phe His Gln Val Gly Met Ile Asp
                85                  90                  95

Cys Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
            130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Glu Pro Asn
            260                 265                 270

Glu Tyr Gly Val Ile Lys Val Cys Asp Glu Phe Pro Gly Phe Ser Arg
    275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
            435

<210> SEQ ID NO 4
<211> LENGTH: 440
<212> TYPE: PRT
<213> ORGANISM: Pyrenochaeta sp.

<400> SEQUENCE: 4

Met Ala Ala Ser Arg Ala Lys Thr Thr Val Ile Val Val Gly Gly Gly
1               5                   10                  15
```

```
Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gln Ser Ala Gly Asn Asp Leu Asn Lys Ile Met Gly Ile Arg Leu Arg
 50                  55                  60

Asn Lys Val Asp Leu Gln Leu Ser Leu Glu Ala Arg Glu Met Trp Arg
65                   70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
 210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
 370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430
```

Asp Glu Ser Pro Arg Ala Lys Leu
            435                 440

<210> SEQ ID NO 5
<211> LENGTH: 452
<212> TYPE: PRT
<213> ORGANISM: Arthrinium sp.

<400> SEQUENCE: 5

Met Ala Ala Ser Arg Lys Thr Thr Lys Val Ile Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
            115                 120                 125

Asp Ser Glu Asp Ala Ile Leu Ala Lys Met Pro Leu Leu Glu Arg Asp
            130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
            195                 200                 205

Thr Lys Tyr Tyr Gly Asp Lys Val Val Leu Ala Ala Gly Ala Trp Ser
            210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
            275                 280                 285

Phe Leu Glu Gln His Gln Ser Tyr Gly Ala Pro Ala Pro Thr Arg Val
            290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
            355                 360                 365

```
Phe Ile Leu Ala Thr Gly Asp Ser Gly His Ser Phe Lys Leu Leu Pro
        370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
                420                 425                 430

Trp Asn His Asp Gly Asp Ser Gly Asn Ala Thr Ser Gly Thr Ser Ser
                435                 440                 445

Glu His Lys Leu
        450

<210> SEQ ID NO 6
<211> LENGTH: 440
<212> TYPE: PRT
<213> ORGANISM: Curvularia clavata

<400> SEQUENCE: 6

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
```

```
                275                 280                 285
Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
        435                 440

<210> SEQ ID NO 7
<211> LENGTH: 441
<212> TYPE: PRT
<213> ORGANISM: Neocosmospora vasinfecta

<400> SEQUENCE: 7

Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205
```

-continued

```
Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Ala Ala Val Tyr Lys Gly
                245                 250                 255

Cys Pro Val Val Tyr His Gly Asp Val Gly Phe Phe Glu Pro Asn
                260                 265                 270

Glu Asn Gly Val Ile Lys Val Cys Asp Glu Phe Pro Gly Phe Thr Arg
                275                 280                 285

Phe Lys Gln His Gln Pro Tyr Gly Ala Pro Ala Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
                340                 345                 350

Ala Asp Ser Ala Leu Leu Ile Cys Glu His Pro Arg Trp Lys Asn Phe
                355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
                420                 425                 430

Lys His Asp Gln Asp Ser Glu Ser Arg
                435                 440

<210> SEQ ID NO 8
<211> LENGTH: 477
<212> TYPE: PRT
<213> ORGANISM: Cryptococcus neoformans

<400> SEQUENCE: 8

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140
```

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
            165                 170                 175

Gly Val Thr Phe Gly Phe Gly Ser Ala Gly Ser Phe Lys Lys Pro Leu
        180                 185                 190

Phe Asp Glu Asp Gly Thr Lys Ala Ile Gly Ile Glu Thr Val Asp Gly
    195                 200                 205

Thr Gln Tyr Phe Ala Asp Lys Val Leu Ala Ala Gly Ala Trp Ser
210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp Val Lys Asp Val Ala
        435                 440                 445

Val Ser Leu Ala Ser Val Lys Ile Gly Glu Asn Ile Gly Glu Lys Val
    450                 455                 460

Val Glu Asp Gly Ala Arg Val Gly Val Lys Val Leu Ala
465                 470                 475

<210> SEQ ID NO 9
<211> LENGTH: 437
<212> TYPE: PRT
<213> ORGANISM: Phaeosphaeria nodorum

<400> SEQUENCE: 9

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser

```
            35                  40                  45
Gln Ser Ala Gly Asn Asp Leu Asn Lys Ile Met Gly Val Ser Leu Arg
 50                  55                  60

Asn Pro Val Asp Leu Gln Leu Ala Leu Glu Ala Arg Gln Met Trp Asn
 65                  70                  75                  80

Glu Asp Glu Leu Phe Lys Lys Phe Phe His Asn Thr Gly Arg Leu Asp
                 85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
130                 135                 140

Lys Gly Trp Lys Ala Ile Phe Ser Lys Asp Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 10
```

```
<211> LENGTH: 438
<212> TYPE: PRT
<213> ORGANISM: Aspergillus nidulans

<400> SEQUENCE: 10
```

| | | | | | | | | | | | | | | |
|---|---|---|---|---|---|---|---|---|---|---|---|---|---|---|
| Met | Thr | Pro | Arg | Ala | Asn | Thr | Lys | Ile | Ile | Val | Val | Gly | Gly | Gly |
| 1 | | | | 5 | | | | | 10 | | | | | 15 |
| Thr | Met | Gly | Ser | Ser | Thr | Ala | Leu | His | Leu | Leu | Arg | Ala | Gly | Tyr | Thr |
| | | | 20 | | | | | 25 | | | | | 30 | | |
| Pro | Ser | Asn | Ile | Thr | Val | Leu | Asp | Thr | Cys | Pro | Ile | Pro | Ser | Ala | Gln |
| | | 35 | | | | | 40 | | | | | 45 | | | |
| Ser | Ala | Gly | Tyr | Asp | Leu | Asn | Lys | Ile | Met | Ser | Ile | Arg | Leu | Arg | Asn |
| | 50 | | | | | 55 | | | | | 60 | | | | |
| Lys | Pro | Asp | Leu | Gln | Leu | Ser | Leu | Glu | Ala | Leu | Asp | Met | Trp | Lys | Asn |
| 65 | | | | | 70 | | | | | 75 | | | | | 80 |
| Asp | Pro | Leu | Phe | Lys | Pro | Phe | Phe | His | Asn | Val | Gly | Met | Ile | Asp | Val |
| | | | | 85 | | | | | 90 | | | | | 95 | |
| Ser | Ser | Thr | Glu | Glu | Gly | Ile | Glu | Gly | Leu | Arg | Lys | Lys | Tyr | Gln | Ser |
| | | | 100 | | | | | 105 | | | | | 110 | | |
| Leu | Leu | Asp | Ala | Gly | Ile | Gly | Leu | Glu | Lys | Thr | Asn | Phe | Met | Leu | Glu |
| | | | 115 | | | | | 120 | | | | | 125 | | |
| Ser | Glu | Asp | Glu | Ile | Leu | Ala | Lys | Ala | Pro | His | Phe | Thr | Gln | Glu | Gln |
| | | 130 | | | | | 135 | | | | | 140 | | | |
| Ile | Lys | Gly | Trp | Lys | Gly | Leu | Phe | Cys | Gly | Asp | Gly | Gly | Trp | Leu | Ala |
| 145 | | | | | 150 | | | | | 155 | | | | | 160 |
| Ala | Ala | Lys | Ala | Ile | Asn | Ala | Ile | Gly | Gln | Phe | Leu | Lys | Glu | Gln | Gly |
| | | | | 165 | | | | | 170 | | | | | 175 | |
| Val | Lys | Phe | Gly | Phe | Gly | Gly | Ala | Gly | Thr | Phe | Lys | Lys | Pro | Leu | Phe |
| | | | 180 | | | | | 185 | | | | | 190 | | |
| Ala | Asp | Ala | His | Glu | Lys | Thr | Cys | Ile | Gly | Val | Glu | Thr | Val | Asp | Gly |
| | | | 195 | | | | | 200 | | | | | 205 | | |
| Thr | Lys | Tyr | Tyr | Ala | Asp | Lys | Val | Val | Leu | Ala | Ala | Gly | Ala | Trp | Ser |
| | 210 | | | | | 215 | | | | | 220 | | | | |
| Ser | Thr | Leu | Val | Asp | Leu | Glu | Glu | Gln | Cys | Val | Ser | Lys | Ala | Trp | Val |
| 225 | | | | | 230 | | | | | 235 | | | | | 240 |
| Phe | Ala | His | Ile | Gln | Leu | Thr | Pro | Ala | Glu | Ala | Ala | Tyr | Lys | Asn |
| | | | | 245 | | | | | 250 | | | | | 255 |
| Thr | Pro | Val | Ile | Tyr | Asp | Gly | Asp | Tyr | Gly | Phe | Phe | Glu | Pro | Asn |
| | | | 260 | | | | | 265 | | | | | 270 | |
| Glu | Asn | Gly | Ile | Ile | Lys | Val | Cys | Asp | Glu | Phe | Pro | Gly | Phe | Thr | His |
| | | 275 | | | | | 280 | | | | | 285 | | | |
| Phe | Lys | Met | His | Gln | Pro | Tyr | Gly | Ser | Pro | Ala | Pro | Lys | Pro | Ile | Ser |
| | 290 | | | | | 295 | | | | | 300 | | | | |
| Val | Pro | Arg | Ser | His | Ala | Lys | His | Pro | Thr | Asp | Thr | Tyr | Pro | His | Ala |
| 305 | | | | | 310 | | | | | 315 | | | | | 320 |
| Ser | Glu | Val | Thr | Ile | Lys | Lys | Ala | Ile | Asn | Arg | Phe | Leu | Pro | Arg | Phe |
| | | | | 325 | | | | | 330 | | | | | 335 | |
| Asn | Asp | Lys | Glu | Leu | Phe | Asn | Arg | Ala | Met | Cys | Trp | Cys | Thr | Asp | Thr |
| | | | 340 | | | | | 345 | | | | | 350 | | |
| Ala | Asp | Ala | Asn | Leu | Leu | Val | Cys | Glu | His | Pro | Arg | Trp | Lys | Gly | Phe |
| | | | 355 | | | | | 360 | | | | | 365 | | |
| Tyr | Leu | Ala | Thr | Gly | Asp | Ser | Gly | His | Ser | Phe | Lys | Leu | Leu | Pro | Asn |
| | 370 | | | | | 375 | | | | | 380 | | | | |
| Ile | Gly | Lys | His | Val | Val | Glu | Leu | Leu | Glu | Glu | Arg | Leu | Glu | Ser | Val |

```
                385                 390                 395                 400
        Phe Lys Asp Ala Trp Arg Trp Arg Pro Gly Ser Gly Asp Ala Leu Lys
                        405                 410                 415

Ser Arg Arg Ala Ala Pro Ala Lys Asp Leu Ala Asp Met Pro Gly Trp
                        420                 425                 430

Arg Asn Glu Ala Lys Met
                        435

<210> SEQ ID NO 11
<211> LENGTH: 438
<212> TYPE: PRT
<213> ORGANISM: Emericella nidulans

<400> SEQUENCE: 11

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
    195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
    275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320
```

```
Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
            405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 12
<211> LENGTH: 441
<212> TYPE: PRT
<213> ORGANISM: Ulocladium sp.

<400> SEQUENCE: 12

Met Ala Pro Asn Arg Ala Asn Ile Ser Val Ile Val Gly Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
            35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
            85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
            115                 120                 125

Asp Ser Glu Asp Lys Ile Leu Glu Lys Met Pro Leu Leu Asn Arg Asp
            130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
            165                 170                 175

Gly Val Lys Phe Gly Phe Gly Ala Gly Ser Phe Lys Gln Pro Leu
            180                 185                 190

Leu Ala Glu Gly Val Cys Val Gly Val Glu Thr Val Asp Gly Thr Arg
            195                 200                 205

Tyr Tyr Ala Asp Lys Val Val Leu Ala Ala Gly Ala Trp Ser Pro Ala
            210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
            245                 250                 255
```

```
Val Val Tyr Asn Gly Asp Val Gly Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
            325                 330                 335

Lys Glu Val Phe Asn Arg His Leu Cys Trp Cys Thr Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
            405                 410                 415

Arg Ala Ala Arg Ala Lys Asp Leu Ala Asp Met Pro Gly Trp Asn His
        420                 425                 430

Asp Gly Glu Ala Pro Arg Ala Lys Leu
    435                 440

<210> SEQ ID NO 13
<211> LENGTH: 437
<212> TYPE: PRT
<213> ORGANISM: Penicillium janthinellum

<400> SEQUENCE: 13

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
```

```
                180                 185                 190
Phe Ala Pro Asp Gly Ala Thr Cys Ser Gly Val Glu Thr Val Asp Gly
            195                 200                 205

Thr Lys Tyr Phe Ala Asp Lys Val Val Leu Ala Ala Gly Ala Trp Ser
            210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
            275                 280                 285

Phe Lys Leu His Gln Pro Tyr Gly Ala Thr Ser Pro Lys Leu Ile Ser
            290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
            355                 360                 365

Ile Leu Ala Thr Gly Asp Ser Gly His Ser Phe Lys Val Leu Pro Asn
            370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435

<210> SEQ ID NO 14
<211> LENGTH: 437
<212> TYPE: PRT
<213> ORGANISM: Coniochaeta sp.

<400> SEQUENCE: 14

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
            100                 105                 110
```

| | | | | | | | | | | | | |
|---|---|---|---|---|---|---|---|---|---|---|---|---|
|Lys|Leu|His|Asp|Ala|Gly|Ala|Gly|Leu|Glu|Lys|Thr|His|Ala|Trp|Leu|
| | |115| | | |120| | | |125| | | | | |

Lys Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Trp Leu
145                 150                 155                 160

Ala Ala Ala Lys Ala Ile Asn Ala Ile Gly Gln Phe Leu Lys Glu Arg
            165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
            210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
            245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 15
<211> LENGTH: 1314
<212> TYPE: DNA
<213> ORGANISM: Coniochaeta sp.

<400> SEQUENCE: 15
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatcatc gcaacaaggt gaacctgcaa atgagtctag aggctagaca gatgtggaag     240

-continued

```
gaggatgagt tattccagcc cttctttcac aataccggca gaatggactg cgaacacacg    300
cctaagggta tcgagaaact gaaaaagctg taccagaaac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtgg tgtaaagttc      540
ggattcggcg cgctggatc cttcaagcaa ccccttttcg acgatgaagg cacaacttgc      600
attggcgttg agacggcaga tggtaccaaa tattacgctg acaaggtggt cttagcagct    660
ggcgcatgga gcccaaccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg actctactct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 16
<211> LENGTH: 437
<212> TYPE: PRT
<213> ORGANISM: Coniochaeta sp.

<400> SEQUENCE: 16

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190
```

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Ala Ala Glu Tyr Lys Gly
            245                 250                 255

Val Pro Val Val Tyr Asn Gly Glu Phe Gly Phe Phe Glu Pro Asp
        260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
        340                 345                 350

Ala Asp Ser Thr Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
            405                 410                 415

Arg Arg Ala Ala Pro Pro Lys Asp Leu Ala Asp Met Pro Gly Trp Lys
        420                 425                 430

His Asp Pro Lys Leu
        435

<210> SEQ ID NO 17
<211> LENGTH: 437
<212> TYPE: PRT
<213> ORGANISM: Coniochaeta sp.

<400> SEQUENCE: 17

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
            85                  90                  95

Cys His Thr Pro Lys Gly Ile Glu Lys Leu Lys Lys Tyr Tyr Gln
            100                 105                 110

Lys Leu His Asp Ala Gly Ala Gly Leu Glu Lys Thr His Ala Trp Leu

Asp Asn Glu Asp Glu Ile Leu Ser Lys Met Pro Leu Leu Gln Arg Asp
                130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
                180                 185                 190

Phe Asp Asp Glu Gly Thr Thr Cys Ile Gly Val Glu Thr Ala Asp Gly
                195                 200                 205

Thr Lys Tyr Tyr Ala Asp Lys Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
                340                 345                 350

Ala Asp Ser Thr Leu Leu Met Cys Glu His Pro Lys Trp Lys Asn Phe
                355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp Pro Lys Leu
            435

<210> SEQ ID NO 18
<211> LENGTH: 437
<212> TYPE: PRT
<213> ORGANISM: Coniochaeta sp.

<400> SEQUENCE: 18

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
                35                  40                  45

```
Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu Ser Thr Pro Lys Gly Ile Glu Lys Leu Lys Lys Tyr Tyr Gln
            100                 105                 110

Lys Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 19
<211> LENGTH: 436
<212> TYPE: PRT
```

<213> ORGANISM: Aspergillus oryzae

<400> SEQUENCE: 19

```
Met Thr Val Ala Lys Ser Ser Ile Leu Ile Ile Gly Ala Gly Thr
  1               5                  10                  15

Trp Gly Ala Ser Thr Ala Leu His Leu Gly Arg Arg Gly Tyr Thr Asn
                 20                  25                  30

Val Thr Val Leu Asp Pro Tyr Thr Val Pro Ser Ala Ile Ser Ala Gly
             35                  40                  45

Asn Asp Val Asn Lys Ile Ile Ser Ser Gly Gln Tyr Ser Asn Lys Lys
 50                  55                  60

Asp Glu Ile Glu Val Asn Glu Ile Leu Ala Glu Ala Phe Lys Gly
 65                  70                  75                  80

Trp Thr Thr Asp Pro Leu Phe Lys Pro Tyr Tyr His Asp Thr Gly Val
                 85                  90                  95

Val Met Ser Ala Cys Ser Ser Ala Gly Leu Asp Arg Leu Gly Ile Arg
            100                 105                 110

Val Arg Pro Glu Glu Pro Asp Val Ser Glu Val Thr Lys Pro Glu
            115                 120                 125

His Phe Arg Gln Leu Ala Pro Ala Val Leu Lys Gly Asn Phe Pro Gly
            130                 135                 140

Trp Arg Gly Tyr His Ile Arg Ser Asn Ala Gly Trp Ala His Ala Arg
145                 150                 155                 160

Asn Ala Leu Val Ala Ala Ile Arg Glu Ala Glu Lys Leu Gly Val Lys
                165                 170                 175

Phe Val Thr Gly Thr Gln Gly Arg Val Ile Thr Leu Ile Phe Glu Asn
                180                 185                 190

Asn Asp Val Lys Gly Ala Val Thr Ala Asp Gly Lys Ile Trp Arg Ala
            195                 200                 205

Glu Gln Thr Val Leu Cys Ala Gly Ala Asn Ala Ala Gln Phe Leu Asp
            210                 215                 220

Phe Lys Asp Gln Leu Arg Pro Thr Ala Trp Thr Leu Ala His Ile Arg
225                 230                 235                 240

Leu Lys Pro Glu Glu Arg Ala Leu Tyr Lys Asn Leu Pro Val Ile Phe
                245                 250                 255

Asn Ile Glu Lys Gly Phe Phe Phe Glu Pro Asp Glu Glu Arg Gly Glu
            260                 265                 270

Ile Lys Ile Cys Asp Glu His Pro Gly Tyr Thr Asn Met Val Lys Ser
        275                 280                 285

Ala Asp Gly His Leu Thr Ser Leu Pro Phe Glu Lys Thr Gln Ile Pro
    290                 295                 300

Lys Glu Ser Glu Ala Arg Val Arg Ala Leu Leu Ser Glu Thr Met Pro
305                 310                 315                 320

Gln Leu Ala Asp Arg Pro Phe Ser Phe Ala Arg Val Cys Trp Cys Ala
                325                 330                 335

Asp Thr Ala Asn Arg Glu Phe Ile Ile Asp Arg His Pro Glu His Pro
            340                 345                 350

Ser Leu Val Leu Gly Cys Gly Ala Ser Gly Arg Gly Phe Lys Tyr Leu
        355                 360                 365

Pro Ser Ile Gly Asn Leu Ile Val Asp Ala Ile Glu Asp Lys Val Pro
    370                 375                 380

Glu Lys Val His Lys Leu Thr Arg Trp Ser Pro Asp Ile Ala Val Asp
385                 390                 395                 400
```

```
Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
            420                 425                 430

Thr Ala Lys Leu
        435
```

<210> SEQ ID NO 20
<211> LENGTH: 438
<212> TYPE: PRT
<213> ORGANISM: Aspergillus fumigatus

<400> SEQUENCE: 20

```
Met Ala Val Thr Lys Ser Ser Leu Leu Ile Val Gly Ala Gly Thr
1               5                   10                  15

Trp Gly Thr Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
                35                  40                  45

Asn Asp Val Asn Lys Val Ile Ser Ser Gly Gln Tyr Ser Asn Asn Lys
50                  55                  60

Asp Glu Ile Glu Val Asn Glu Ile Leu Ala Glu Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
        115                 120                 125

Gln Phe Arg Lys Leu Ala Pro Glu Gly Val Leu Gln Gly Asp Phe Pro
130                 135                 140

Gly Trp Lys Gly Tyr Phe Ala Arg Ser Gly Ala Gly Trp Ala His Ala
145                 150                 155                 160

Arg Asn Ala Leu Val Ala Ala Arg Glu Ala Gln Arg Met Gly Val
                165                 170                 175

Lys Phe Val Thr Gly Thr Pro Gln Gly Arg Val Val Thr Leu Ile Phe
            180                 185                 190

Glu Asn Asn Asp Val Lys Gly Ala Val Thr Gly Asp Gly Lys Ile Trp
        195                 200                 205

Arg Ala Glu Arg Thr Phe Leu Cys Ala Gly Ala Ser Ala Gly Gln Phe
210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
        275                 280                 285

Gln Ser Ala Asp Gly Thr Met Met Ser Ile Pro Phe Glu Lys Thr Gln
290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                325                 330                 335
```

Cys Ala Asp Thr Ala Asn Arg Glu Phe Leu Ile Asp Arg His Pro Gln
                340                 345                 350

Tyr His Ser Leu Val Leu Gly Cys Gly Ala Ser Gly Arg Gly Phe Lys
            355                 360                 365

Tyr Leu Pro Ser Ile Gly Asn Leu Ile Val Asp Ala Met Glu Gly Lys
        370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
                405                 410                 415

Arg Val Met Asp Phe His Asp Val Lys Glu Trp Thr Asn Val Gln Tyr
            420                 425                 430

Arg Asp Ile Ser Lys Leu
            435

<210> SEQ ID NO 21
<211> LENGTH: 437
<212> TYPE: PRT
<213> ORGANISM: Aspergillus terreus

<400> SEQUENCE: 21

Met Pro Val Thr Lys Ser Ser Ile Leu Ile Ile Gly Ala Gly Thr
1               5                   10                  15

Trp Gly Cys Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
            35                  40                  45

Asn Asp Val Asn Lys Ile Ile Ser Ser Gly Gln Tyr Ser Ser Lys Lys
        50                  55                  60

Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
        115                 120                 125

Gln Phe Arg Gln Leu Ala Pro Gly Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Ala Arg Glu Ala Gln Arg Leu Gly Val Arg
                165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
        195                 200                 205

Ala Glu Gln Thr Ile Leu Cys Ala Gly Ala Ala Gly Gln Phe Leu
    210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Phe Glu Pro Asp Glu Glu Arg Gly

```
                    260                 265                 270
Glu Ile Lys Ile Cys Asp Glu His Pro Gly Tyr Thr Asn Met Thr Thr
            275                 280                 285

Gly Ala Asp Gly Arg Val Arg Ser Ile Pro Phe Glu Lys Thr Gln Val
        290                 295                 300

Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
            325                 330                 335

Ala Asp Thr Pro Asn Arg Glu Phe Ile Ile Asp Arg His Pro Glu Tyr
        340                 345                 350

Pro Ser Leu Val Leu Gly Cys Gly Ala Ser Gly Arg Gly Phe Lys Tyr
            355                 360                 365

Leu Pro Ser Ile Gly Ser Ile Ile Ala Asp Ala Met Glu Asp Lys Thr
        370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Gly Pro Asn Arg
                405                 410                 415

Val Met Asp Phe Asn Glu Val Lys Glu Trp Thr Asn Val Thr Gln Arg
            420                 425                 430

Asp Ile Ser Lys Leu
            435

<210> SEQ ID NO 22
<211> LENGTH: 440
<212> TYPE: PRT
<213> ORGANISM: Fusarium oxysporum

<400> SEQUENCE: 22

Ala Ser Thr Leu Thr Lys Gln Ser Gln Ile Leu Ile Val Gly Gly Gly
1               5                   10                  15

Thr Trp Gly Cys Ser Thr Ala Leu His Leu Ala Arg Arg Gly Tyr Thr
            20                  25                  30

Asn Val Thr Val Leu Asp Val Asn Arg Ile Pro Ser Pro Ile Ser Ala
        35                  40                  45

Gly His Asp Val Asn Lys Leu Ala Gly Arg Leu Ser Thr Ala Asp Ser
    50                  55                  60

Lys Gly Asp Asp Glu Asp Ser Ile Trp Lys Ala Leu Ser Tyr Ala Ala
65                  70                  75                  80

Ala Gln Gly Trp Leu His Asp Pro Val Phe Gln Pro Phe Cys His Asn
                85                  90                  95

Thr Gly Ser Val Val Ala Gly Ser Thr Pro Lys Ser Ile Lys Gln Leu
            100                 105                 110

Val Glu Asp Glu Ile Gly Asp Ile Asp Gln Tyr Thr Pro Leu Asn
        115                 120                 125

Thr Ala Glu Asp Phe Arg Lys Thr Met Pro Glu Gly Ile Leu Thr Gly
    130                 135                 140

Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
            180                 185                 190
```

```
Leu Ile Phe Glu Asp Gly Asp Val Arg Gly Ala Lys Thr Ala Asp Gly
            195                 200                 205

Lys Glu His Arg Ala Asp Arg Thr Ile Leu Ser Ala Gly Ala Ser Ala
        210                 215                 220

Glu Phe Phe Leu Asp Phe Glu Asn Gln Ile Gln Pro Thr Ala Trp Thr
225                 230                 235                 240

Leu Gly His Ile Gln Ile Thr Pro Glu Glu Thr Lys Leu Tyr Lys Asn
                245                 250                 255

Leu Pro Pro Leu Phe Asn Ile Asn Gln Gly Phe Phe Met Glu Pro Asp
            260                 265                 270

Glu Asp Leu His Gln Leu Lys Met Cys Asp Glu His Pro Gly Tyr Cys
        275                 280                 285

Asn Trp Val Glu Lys Pro Gly Ser Lys Tyr Pro Gln Ser Ile Pro Phe
290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
            340                 345                 350

Tyr His Pro Arg His Pro Ser Leu Val Ile Ala Ser Gly Asp Cys Gly
        355                 360                 365

Thr Gly Tyr Lys His Ile Thr Ser Ile Gly Lys Phe Ile Ser Asp Cys
        370                 375                 380

Met Glu Gly Thr Leu Glu Glu Arg Phe Ala Lys Tyr Trp Arg Trp Arg
385                 390                 395                 400

Pro Glu Lys Phe Thr Glu Phe Trp Gly Lys Asp Pro Leu Asp Arg Phe
                405                 410                 415

Gly Ala Asp Asp Lys Ile Met Asp Leu Pro Lys Ser Asp Val Glu Gly
            420                 425                 430

Trp Thr Asn Ile Lys Asn Asp Ile
        435                 440

<210> SEQ ID NO 23
<211> LENGTH: 445
<212> TYPE: PRT
<213> ORGANISM: Aspergillus oryzae

<400> SEQUENCE: 23

Met Thr Ser Ser Lys Leu Thr Pro Thr Ser Ile Leu Ile Val Gly
1               5                   10                  15

Ala Gly Thr Trp Gly Cys Ser Thr Ala Leu His Leu Ala Arg Arg Gly
                20                  25                  30

Tyr Lys Asn Val Thr Val Leu Asp Pro His Pro Val Pro Ser Pro Ile
            35                  40                  45

Ala Ala Gly Asn Asp Ile Asn Lys Ile Met Glu His Arg Glu Val Lys
        50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
            100                 105                 110

His Ile Gln Glu His Glu Ile Asp Ser Ser Asp Ala Glu Phe Ile Lys
        115                 120                 125
```

```
Leu Asn Thr Ala Glu Asp Phe Arg Lys Thr Met Pro Pro Gly Ile Leu
            130                 135                 140

Thr Gly Asn Phe Pro Gly Trp Lys Gly Trp Leu Asn Lys Thr Gly Ala
145                 150                 155                 160

Gly Trp Ile His Ala Lys Lys Ala Met Phe Ser Ala Tyr Thr Glu Ala
                165                 170                 175

Lys Arg Leu Gly Val Thr Phe Ile Thr Gly Ser Pro Glu Gly Asp Val
                180                 185                 190

Val Ser Leu Ile Tyr Glu Asn Gly Asp Val Val Gly Ala Arg Thr Ala
                195                 200                 205

Asp Gly Thr Val His Arg Ala Asp His Thr Ile Leu Ser Ala Gly Ala
            210                 215                 220

Gly Ser Asp Arg Leu Leu Asp Phe Lys Lys Gln Leu Arg Pro Thr Ala
225                 230                 235                 240

Trp Thr Leu Cys His Ile Arg Met Thr Pro Asp Glu Ala Lys Lys Tyr
                245                 250                 255

Arg Asn Leu Pro Val Leu Phe Asn Val Ala Lys Gly Phe Phe Met Glu
                260                 265                 270

Pro Asp Glu Asp Asn His Glu Leu Lys Ile Cys Asp Glu His Pro Gly
            275                 280                 285

Tyr Cys Asn Phe Val Pro Asp Pro Lys His Gly Gly Glu Val Arg Ser
        290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                325                 330                 335

Ser Phe Ala Arg Ile Cys Trp Asp Ala Asp Thr Val Asp Arg Ala Phe
                340                 345                 350

Leu Ile Asp Arg His Pro Glu Tyr Arg Ser Leu Leu Leu Ala Val Gly
            355                 360                 365

Gly Ser Gly Asn Gly Ala Met Gln Met Pro Thr Ile Gly Gly Phe Ile
        370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                405                 410                 415

Asn Arg Phe Gly Gly Pro Asn Lys Val Met Asp Phe Gln Lys Val Gly
                420                 425                 430

Glu Asn Glu Trp Thr Lys Ile Gly Asp Lys Ser Arg Leu
            435                 440                 445

<210> SEQ ID NO 24
<211> LENGTH: 445
<212> TYPE: PRT
<213> ORGANISM: Aspergillus fumigatus

<400> SEQUENCE: 24

Met Ala Pro Ser Ile Leu Ser Thr Glu Ser Ile Ile Val Ile Gly
1               5                   10                  15

Ala Gly Thr Trp Gly Cys Ser Thr Ala Leu His Leu Ala Arg Arg Gly
                20                  25                  30

Tyr Lys Asp Val Thr Val Leu Asp Pro His Pro Val Pro Ser Pro Ile
            35                  40                  45

Ala Ala Gly Asn Asp Ile Asn Lys Ile Met Glu His Ser Glu Leu Lys
```

```
            50                  55                  60
Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
                    100                 105                 110

His Ile Arg Lys Asp Glu Val Glu Pro Ser Glu Thr Asn Phe Val Lys
                    115                 120                 125

Leu Glu Thr Ala Glu Asp Phe Arg Arg Thr Met Pro Pro Gly Val Leu
                130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                    165                 170                 175

Lys Arg Leu Gly Val Arg Phe Val Thr Gly Ser Pro Glu Gly Asn Val
                180                 185                 190

Val Ser Leu Val Tyr Glu Asp Gly Asp Val Val Gly Ala Arg Thr Ala
                195                 200                 205

Asp Gly Arg Val His Lys Ala His Arg Thr Ile Leu Ser Ala Gly Ala
                210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                    245                 250                 255

Arg Asn Leu Pro Val Leu Phe Asn Ile Ala Lys Gly Phe Phe Met Glu
                260                 265                 270

Pro Asp Glu Asp Lys His Glu Leu Lys Ile Cys Asp Glu His Pro Gly
                275                 280                 285

Tyr Cys Asn Phe Leu Pro Asp Pro Asn Arg Pro Gly Gln Glu Lys Ser
                290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                    325                 330                 335

Ser Phe Ala Arg Ile Cys Trp Asp Ala Asp Thr Pro Asp Arg Ala Phe
                340                 345                 350

Leu Ile Asp Arg His Pro Glu His Pro Ser Leu Leu Val Ala Val Gly
                355                 360                 365

Gly Ser Gly Asn Gly Ala Met Gln Met Pro Thr Ile Gly Gly Phe Ile
                370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                    405                 410                 415

Asn Arg Phe Gly Gly Pro Asp Arg Ile Met Asp Phe Gln Gln Val Gly
                420                 425                 430

Glu Asp Gln Trp Thr Lys Ile Gly Glu Ser Arg Gly Pro
                435                 440                 445

<210> SEQ ID NO 25
<211> LENGTH: 427
<212> TYPE: PRT
<213> ORGANISM: Pichia sp.
```

<400> SEQUENCE: 25

| | | | | | | | | | | | | | | |
|---|---|---|---|---|---|---|---|---|---|---|---|---|---|---|
|Met|Glu|Ser|Ile|Ile|Ile|Val|Gly|Ala|Gly|Thr|Phe|Gly|Leu|Ser|Thr|
|1| | | |5| | | | |10| | | | |15| |

Ala Leu Gln Leu Ala Arg Asp Gly Tyr Lys Asn Ile Lys Cys Phe Asp
              20                  25                  30

Lys Phe Pro Val Pro Ser Glu Ile Ala Ala Gly Asn Asp Ser Asn Lys
              35                  40                  45

Ile Phe His Tyr Asp Tyr Val Ala Pro Leu Ala Lys Pro Asn Ser Lys
50                      55                  60

Glu Arg Leu Ser Leu Glu Ala Leu His Leu Trp Lys Thr Asp Pro Val
65                      70                  75                  80

Tyr Lys Pro Tyr Tyr His Pro Val Gly Phe Ile Leu Ala Ala Ser Ser
              85                  90                  95

Asp Ala Pro Leu Leu His Asp Lys Glu Tyr Tyr Glu Leu Gln Lys
              100                 105                110

Asn Gly Leu Arg Asn Tyr Arg Tyr Ile Ser Thr Pro Glu Glu Phe Arg
              115                 120                125

Glu Tyr Leu Pro Ile Leu Lys Gly Pro Leu Pro Asn Trp Arg Gly Tyr
130                      135                  140

Val Leu Asp Gly Asp Asn Gly Trp Leu His Ala Arg Asp Ser Leu Lys
145                      150                  155              160

Ser Ala Tyr Glu Glu Cys Lys Arg Leu Gly Val Glu Phe Val Phe Gly
              165                 170                175

Asp Asp Gly Glu Ile Val Glu Leu Leu Asn Glu Asn Gly Lys Leu Thr
              180                 185                190

Gly Ile Arg Ala Arg Ser Gly Ala Ile Phe Ser Ala Gln Lys Tyr Val
              195                 200                205

Leu Ser Ser Gly Ala Asn Ala Val Thr Leu Leu Asn Phe Gln Arg Gln
210                      215                  220

Leu Glu Gly Lys Cys Phe Thr Leu Ala His Phe Lys Val Thr Asp Glu
225                      230                  235              240

Glu Ala Lys Ala Phe Lys Ser Leu Pro Val Leu Phe Asn Ala Glu Lys
              245                 250                255

Gly Phe Phe Phe Glu Ala Asp Glu Asn Asn Glu Ile Lys Ile Cys Asn
              260                 265                270

Glu Tyr Pro Gly Phe Thr His Thr Asn Glu Ser Gly Glu Ser Ile Pro
              275                 280                285

Leu Tyr Arg Met Glu Ile Pro Leu Glu Ser Ala Leu Glu Ile Arg Gln
              290                 295                300

Tyr Leu Lys Glu Thr Met Pro Gln Phe Ala Asp Arg Pro Phe Thr Lys
305                      310                  315              320

Thr Arg Ile Cys Trp Cys Thr Asp Ser Pro Asp Met Gln Leu Ile Leu
              325                 330                335

Cys Thr His Pro Glu Tyr Thr Asn Leu Ile Val Ala Ser Gly Asp Ser
              340                 345                350

Gly Asn Ser Phe Lys Ile Met Pro Ile Ile Gly Lys Tyr Val Ser Lys
              355                 360                365

Val Val Thr Lys Gly Asp Lys Gly Leu Asp Pro Glu Asp Lys Glu Cys
              370                 375                380

Trp Lys Trp Arg Pro Glu Thr Trp Asp Lys Arg Gly Gln Val Arg Trp
385                      390                  395              400

Gly Gly Arg Tyr Arg Val Ala Asp Leu Asn Glu Ile Glu Glu Trp Val

```
                    405                 410                 415
Ser Val Glu Asn Pro Thr Pro His Lys Leu Glu
            420                 425

<210> SEQ ID NO 26
<211> LENGTH: 426
<212> TYPE: PRT
<213> ORGANISM: Debaryomyces hansenii

<400> SEQUENCE: 26

Met Asp Lys Pro Gly Lys Ile Leu Ile Ile Gly Ala Gly Thr Phe Gly
1               5                   10                  15

Leu Ser Thr Ala Leu His Leu Leu Arg Gln Gly Glu Lys Asp Val Ile
            20                  25                  30

Leu Val Asp Pro Tyr Ala Val Pro Ser Pro Phe Ser Ala Gly Asn Asp
        35                  40                  45

Val Asn Lys Ile Ile Gln Thr Thr Ser Asp Asp Phe Tyr Ser Lys
    50                  55                  60

Leu Ala Leu Glu Ala Leu Glu Met Trp Arg Glu Asp Asn Val Phe Asn
65                  70                  75                  80

Lys Ala Phe Ala Glu Thr Gly Ile Ile Tyr Ala Ala Thr Gly Lys Glu
                85                  90                  95

Gln Arg Glu Ser Ile Asp Tyr Arg Tyr Glu Tyr Leu Leu Gly Arg Lys
            100                 105                 110

Asp Lys Val Val Lys Leu Asn Ser Val Glu Asp Tyr Glu Lys Tyr Val
        115                 120                 125

Pro Asn Lys Glu Gly Ser Lys Ser Tyr Pro Asn Lys Phe Gln Lys Trp
    130                 135                 140

Tyr Gly Tyr Tyr Gln Glu Lys Asn Cys Gly Trp Ala Phe Ala Arg Leu
145                 150                 155                 160

Ala Leu Glu Asn Cys Val Glu Glu Cys Arg Lys Leu Gly Ala Lys Phe
                165                 170                 175

Val Ile Asp Ser Ala Glu Glu Leu Leu Phe Ser Glu Asp Gly Ala Cys
            180                 185                 190

Val Gly Val His Thr Ser Asn Gly Asn Ile Ile Glu Ala Asp Arg Thr
        195                 200                 205

Ile Ile Cys Ala Gly Ala Asn Ser Phe Lys Phe Leu Asn Phe Glu Gln
    210                 215                 220

Gln Leu Leu Ala Lys Cys Tyr Thr Leu Gly His Ile Lys Leu Thr Asp
225                 230                 235                 240

Asp Glu Ala Ala Leu Leu Lys Gly Met Pro Val Val Leu Asn Leu Asp
                245                 250                 255

Gly Gly Phe Val Phe Glu Pro Asp Leu Asn Asn Glu Ile Lys Phe Cys
            260                 265                 270

Asn Glu Phe Pro Gly Tyr Val Asn Ile Val Asn Glu Asp Ser Val Pro
        275                 280                 285

Ser Phe Lys Asp Ser Ile Pro Lys Glu Ala Glu Asp Gln Met Arg Ala
    290                 295                 300

Phe Leu Arg Gln Val Phe Pro Glu Phe Ala Glu Arg Glu Phe Ser Leu
305                 310                 315                 320

Ala Arg Ile Cys Trp Cys Thr Asp Thr Pro Asp Arg His Phe Leu Ile
                325                 330                 335

Cys Glu His Pro Gly His Lys Asn Leu Val Leu Gly Thr Gly Asp Ser
            340                 345                 350
```

Gly Gln Gly Phe Lys Tyr Met Pro Asn Val Gly Lys Tyr Ile Ser Gln
            355                 360                 365

Val Ala Leu Lys Gly Glu Asn Ser Leu Asp Lys Asp Lys Lys Glu Leu
        370                 375                 380

Trp Arg Trp Arg Pro Asp Met Gly Lys Lys Arg Asp Leu Lys Asp Leu
385                 390                 395                 400

Gln Gly Arg Tyr Gly Gly Ser Asn Glu Val Lys Asp Leu Lys Asn Val
            405                 410                 415

Lys Gln Trp Ser Asn Gly Lys Ser His Leu
        420                 425

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
atgatctatt cccatgatct tgttgag                                   27

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tgggaataga tcatggcaac aaggtgaacc                                30

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29 cttttcagt ttctcgatac ccttaggcgt                                30

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
agaaactgaa aaagtattac cagaaactgc                                30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
ttcgcagtcc attctgccgg tattgtgaaa                                30

<210> SEQ ID NO 32
<211> LENGTH: 30
<212> TYPE: DNA

<213> ORGANISM: Artificial
<220> FEATURE:
<223> OTHER INFORMATION: primer

<400> SEQUENCE: 32
atggactgcg aaagcacgcc taagggtatc            30

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
gaagaagcca aattcgccat tatacacaac            30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
gaatttggct tcttcatgga acctgatgag            30

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
gaatttggct tcttcctcga acctgatgag            30

<210> SEQ ID NO 36
<211> LENGTH: 27
<212> TYPE: DNA
<213> ORGANISM: Artificial
<220> FEATURE:
<223> OTHER INFORMATION: primer

<400> SEQUENCE: 36
cacctttatt acaccaaact catcagg            27

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
gtgtaataaa ggtgcaggac gaattcccag            30

HBA1C DEHYDROGENASE

CROSS-REFERENCE TO RELATED APPLICATIONS

This application is a National Stage application of PCT/JP2017/016058, filed Apr. 21, 2017, which claims priority from Japanese application JP 2016-086592, filed Apr. 22, 2016.

TECHNICAL FIELD

The present invention relates to an amadoriase having enhanced dehydrogenase activity, an amadoriase having lowered oxidase activity, and an amadoriase having enhanced dehydrogenase activity and lowered oxidase activity, capable of acting on HbA1c, genes and recombinant DNAs thereof, and a method for producing such amadoriases. The present invention also relates to a dehydrogenase that acts on HbA1c which can effectively be used as a diagnostic enzyme or a sensor for diabetes or for a measurement kit of a diabetes marker.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, glycated hemoglobin (HbA1c) has drawn attention as a glycemic control marker significant for diagnosis of diabetic patients and control of conditions in the field of clinical diagnosis of diabetes mellitus. The blood HbA1c level reflects the average blood glucose level for a given period of time in the past, and the measured value thereof serves as a significant indicator for diagnosis and control of diabetes conditions.

As a method for rapidly and readily measuring HbA1c, an enzymatic method using an amadoriase has been proposed, in which HbA1c is decomposed with e.g., a protease, and α-fructosyl valyl histidine (hereinafter referred to as "αFVH") or α-fructosyl valine (hereinafter referred to as "αFV") released from a β chain amino terminus thereof is quantified (see, for example, Patent Literatures 1 to 7).

In addition, methods for measuring HbA1c by using an amadoriase include a method in which HbA1c is digested with Glu-C protease, α-fructosyl hexapeptide (α-fructosyl-valyl-histidyl-leucyl-threonyl-proryl-glutamic acid; hereafter abbreviated as "αF6P") comprising 6 amino acids including valine at the glycated β-chain amino terminus is released, and the released αF6P is then quantified (see, for example, Patent Literatures 16, 17, 18, and 19). This method of assaying HbA1c using an enzyme is carried out in accordance with the HbA1c assay method (see Non-Patent Document 10) determined by the International Federation of Clinical Chemistry and Laboratory Medicine (IFCC).

However, proteases and peptidases can act on amadoriases, peroxidases, and other protein reagents. Accordingly, the present inventors developed an amadoriase capable of directly acting on HbA1c without a protease (Patent Document 20). Other similar reports have also been made (Patent Document 21). Such amadoriase transfers an electron to an oxygen molecule when oxidizing the glycated substrate.

An amadoriase catalyzes a reaction of oxidizing iminodiacetic acid or a derivative thereof (also referred to as an "Amadori compound") in the presence of oxygen to produce glyoxylic acid or α-ketoaldehyde, an amino acid or a peptide, and hydrogen peroxide.

Amadoriases have been found in bacteria, yeast, and fungi. For example, amadoriases having enzymatic activity on αFVH and/or αFV, which is particularly useful for measurement of HbA1c, and derived from the genera Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium, Arthrobacter, and Debaryomyces have been reported (e.g., Patent Documents 1 and 6 to 15 and Non-Patent Documents 1 to 11). In some of these documents, an amadoriase may also be referred to as, for example, ketoamine oxidase, fructosyl amino acid oxidase, fructosyl peptide oxidase, or fructosyl amine oxidase.

An amadoriase may be used in conjunction with a peroxidase and, by utilizing a colorimetric substrate, may be used for the assay of a glycated substrate in a sample. Conventional amadoriases are capable of transmitting electrons to oxygen molecules when oxidizing a glycated substrate. Such activity is referred to as an "oxidase activity." On the other hand, when a conventional amadoriase oxidizes a glycated substrate, it is also possible for the conventional amadoriase to transfer an electron to an electron acceptor (i.e., an electron mediator) that is different from an oxygen molecule. Such activity is referred to as "dehydrogenase activity." By lowering the oxidase activity of an enzyme and enhancing the dehydrogenase activity thereof, an electron can be preferentially transferred to an electron acceptor (i.e., an electron mediator) when oxidizing a glycated substrate. Thus, an electron from a glycated substrate can be assayed without being affected by oxygen in the sample.

There is disclosure of enhanced dehydrogenase activity of an amadoriase in the known literature. For example, it is shown that substitution of asparagine at position 56 of fructosyl amino acid oxidase derived from Phaeosphaeria nodorum with alanine leads to enhanced dehydrogenase activity ($V_{max}/K_m$ relative to αFV) by 2.3 times (Patent Document 16). However, the variant disclosed therein also has enhanced oxidase activity ($V_{max}/K_m$ relative to αFV) by 1.2 times compared with the wild-type. Accordingly, it is believed that such variant remains susceptible to oxygen. In addition, while the disclosed variant recognizes αFV as a substrate, it is believed that the disclosed variant does not directly act on HbA1c.

Patent Document 22 reports a mutation that enhances heat stability of an amadoriase, and describes a variant with enhanced heat stability that results from modification of Phe at position 267 with Tyr in the amino acid sequence of the amadoriase derived from the genus Coniochaeta (F267Y).

PRIOR ART DOCUMENTS

Patent Documents

Patent Document 1: WO 2004/104203
Patent Document 2: WO 2005/49857
Patent Document 3: JP 2001-95598 A Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2011/015325
Patent Document 17: WO 2008/108385
Patent Document 18: WO 2015/005258
Patent Document 19: WO 2013/162035
Patent Document 20: WO 2015/060429
Patent Document 21: WO 2015/005257
Patent Document 22: WO 2013/100006

Non-Patent Documents

Non-Patent Document 1: Biochem. Biophys. Res. Commun., 311, 104-11, 2003
Non-Patent Document 2: Biotechnol. Bioeng., 106, 358-66, 2010
Non-Patent Document 3: J. Biosci. Bioeng., 102, 241-3, 2006
Non-Patent Document 4: Eur. J. Biochem., 242, 499-505, 1996
Non-Patent Document 5: Arch. Microbiol., 178, 344-50, 2002
Non-Patent Document 6: Mar. Biotechnol., 6, 625-32, 2004
Non-Patent Document 7: Biosci. Biotechnol. Biochem., 59, 487-91, 1995
Non-Patent Document 8: Appl. Microbiol. Biotechnol., 74, 813-819, 2007
Non-Patent Document 9: Biosci. Biotechnol. Biochem., 66, 1256-61, 2002
Non-Patent Document 10: Biosci. Biotechnol. Biochem., 66, 2323-29, 2002
Non-Patent Document 11: Biotechnol. Letters 27, 27-32, 2005

SUMMARY OF THE INVENTION

Objects to be Attained by the Invention

It is an object of the present invention to provide an amadoriase that acts on HbA1c and has lowered oxidase activity and enhanced dehydrogenase activity. It is another object of the present invention to provide an amadoriase that acts on HbA1c and has activity, which is not substantially influenced by dissolved oxygen levels.

Means for Attaining the Objects

At present, there is almost no information available for lowering of the oxidase activity of an enzyme and enhancement of the dehydrogenase activity. Under such circumstances, the present inventors have conducted concentrated studies and, as a result, discovered that the above objects can be attained by introducing substitution of a particular amino acid residue into an amadoriase derived from the genus *Coniochaeta*. This has led to the completion of the present invention.

The present invention encompasses the following.
[1] A method for measurement of hemoglobin A1c in a sample comprising allowing HbA1c dehydrogenase capable of directly acting on hemoglobin A1c to act on a sample and measuring a reduced electron mediator that is not hydrogen peroxide generated by the action or an oxidized electron mediator that is not oxygen consumed by the action.
[2] The method for measurement according to [1], wherein the measurement is an electrochemical measurement using an HbA1c dehydrogenase, an enzyme electrode comprising HbA1c dehydrogenase or an enzyme sensor comprising, as a working electrode, the enzyme electrode, and an electron mediator that is not oxygen or wherein the measurement is an absorbance measurement using HbA1c dehydrogenase, a colorimetric substrate, and an electron mediator that is not oxygen.
[3] A dehydrogenase that directly acts on HbA1c and has a lower ratio of oxidase activity to dehydrogenase activity (OX/DH), compared with a (parent) amadoriase that directly acts on hemoglobin A1c prior to modification, wherein the dehydrogenase is:
(i) an HbA1c dehydrogenase, wherein, when the amino acid sequence of the amadoriase is aligned with the amino acid sequence of SEQ ID NO: 1, one or more amino acids at positions corresponding to the positions selected from the group consisting of positions 280, 269, 54, 241, and 267 of the amino acid sequence of SEQ ID NO: 1 are substituted, and wherein the HbA1c dehydrogenase is capable of directly acting on hemoglobin A1c and has dehydrogenase activity;
(ii) the HbA1c dehydrogenase as defined in (i) consisting of an amino acid sequence in which one or several amino acids at positions other than the positions corresponding to positions 280, 269, 54, 241, and 267 of the amino acid sequence of SEQ ID NO: 1 is(are) substituted, deleted, or added, wherein the HbA1c dehydrogenase is capable of directly acting on hemoglobin A1c and has dehydrogenase activity;
(iii) the HbA1c dehydrogenase as defined in (i) comprising an amino acid sequence having 70% or higher sequence identity with any of the amino acid sequences of SEQ ID NO: 1 and SEQ ID NOs: 3 to 14 over the full length and 90% or higher sequence identity between the amino acid sequence of the homologous region of SEQ ID NO: 1 and the amino acid sequence of the corresponding homologous region of the amadoriase, wherein the homologous region of SEQ ID NO: 1 consists of the amino acid sequence of positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 1, wherein the HbA1c dehydrogenase is capable of directly acting on hemoglobin A1c and has dehydrogenase activity;
(iv) the HbA1c dehydrogenase as defined in (i) comprising an amino acid sequence having 80% or higher sequence identity with any of the amino acid sequences of SEQ ID NO: 1 and SEQ ID NOs: 3 to 14 over the full length, wherein the HbA1c dehydrogenase is capable of directly acting on hemoglobin A1c and has dehydrogenase activity; or
(v) the HbA1c dehydrogenase as defined in (i) comprising an amino acid sequence having 90% or higher sequence identity between the amino acid sequence of the conserved region of SEQ ID NO: 1 and the amino acid sequence of the corresponding conserved region of the sequence of the naturally-occurring amadoriase from which the HbA1c dehydrogenase is derived, wherein the conserved region of SEQ ID NO: 1 consists of positions 11, 12, 13, 15, 17, 18, 20, 22, 23, 24, 25, 27, 29, 31, 36, 37, 41, 46, 47, 50, 51, 52, 54, 56, 57, 58, 75, 79, 82, 84, 85, 93, 95, 149, 158, 159, 162, 165, 166, 177, 180, 202, 208, 218, 220, 221, 222, 224, 228, 233, 239, 243, 246, 250, 255, 258, 260, 266, 267, 270, 272, 277, 278, 280, 281, 282, 284, 285, 286, 318, 321, 326, 329, 334, 339, 346, 347, 348, 351, 352, 354, 358, 359, 362, 363, 370, 373, 376, 382, 385, 386, 389, 406, 407, 409, 418, 425, and 427 of SEQ ID NO: 1, and wherein the HbA1c dehydrogenase is capable of directly acting on hemoglobin A1c and has dehydrogenase activity.

[4] The HbA1c dehydrogenase according to [3], wherein the amino acid at the position corresponding to position 280 of the amino acid sequence of SEQ ID NO: 1 is substituted with a polar amino acid selected from the group consisting of glutamine, serine, threonine, and asparagine, a charged amino acid selected from the group consisting of aspartic acid, glutamic acid, lysine, arginine, and histidine, or an amino acid selected from the group consisting of methionine, proline, phenylalanine, tyrosine, and tryptophan;

the amino acid at the position corresponding to position 269 of the amino acid sequence of SEQ ID NO: 1 is substituted with methionine, leucine, tyrosine, isoleucine, tryptophan, valine, or alanine;

the amino acid at the position corresponding to position 54 of the amino acid sequence of SEQ ID NO: 1 is substituted with an amino acid selected from the group consisting of asparagine, alanine, glutamine, histidine, glycine, and valine;

the amino acid at the position corresponding to position 241 of the amino acid sequence of SEQ ID NO: 1 is substituted with an amino acid selected from the group consisting of glutamine, lysine, glutamic acid, asparagine, arginine, aspartic acid, and histidine; or the amino acid at the position corresponding to position 267 of the amino acid sequence of SEQ ID NO: 1 is substituted with methionine, leucine, tyrosine, isoleucine, tryptophan, valine, or alanine.

[5] The HbA1c dehydrogenase according to [4], wherein the amino acid at the position corresponding to position 280 of the amino acid sequence of SEQ ID NO: 1 is substituted with glutamine, serine, histidine, threonine, asparagine, aspartic acid, glutamic acid, lysine, arginine, or methionine;

the amino acid at the position corresponding to position 269 of the amino acid sequence of SEQ ID NO: 1 is substituted with methionine, leucine, tyrosine, isoleucine, or tryptophan;

the amino acid at the position corresponding to position 54 of the amino acid sequence of SEQ ID NO: 1 is substituted with asparagine or alanine;

the amino acid at the position corresponding to position 241 of the amino acid sequence of SEQ ID NO: 1 is substituted with glutamine, glutamic acid, or lysine; or the amino acid at the position corresponding to position 267 of the amino acid sequence of SEQ ID NO: 1 is substituted with methionine, leucine, tyrosine, isoleucine, or tryptophan.

[6] The HbA1c dehydrogenase according to [5], wherein the amino acid at the position corresponding to position 280 of the amino acid sequence of SEQ ID NO: 1 is substituted with glutamine, serine, histidine, threonine, asparagine, aspartic acid, glutamic acid, lysine, arginine, or methionine;

the amino acid at the position corresponding to position 269 of the amino acid sequence of SEQ ID NO: 1 is substituted with methionine, leucine, or tyrosine;

the amino acid at the position corresponding to position 54 of the amino acid sequence of SEQ ID NO: 1 is substituted with asparagine or alanine;

the amino acid at the position corresponding to position 241 of the amino acid sequence of SEQ ID NO: 1 is substituted with glutamine, glutamic acid, or lysine; or the amino acid at the position corresponding to position 267 of the amino acid sequence of SEQ ID NO: 1 is substituted with methionine, leucine, or tyrosine.

[7] The HbA1c dehydrogenase according to [5], wherein the amino acid at the position corresponding to position 280 of the amino acid sequence of SEQ ID NO: 1 is substituted with glutamine or serine;

the amino acid at the position corresponding to position 269 of the amino acid sequence of SEQ ID NO: 1 is substituted with methionine, leucine, or tyrosine;

the amino acid at the position corresponding to position 241 of the amino acid sequence of SEQ ID NO: 1 is substituted with glutamine; or the amino acid at the position corresponding to position 267 of the amino acid sequence of SEQ ID NO: 1 is substituted with methionine, leucine, or tyrosine.

[8] The HbA1c dehydrogenase according to [5], wherein the amino acid at the position corresponding to position 280 of the amino acid sequence of SEQ ID NO: 1 is substituted with glutamine or histidine;

the amino acid at the position corresponding to position 269 of the amino acid sequence of SEQ ID NO: 1 is substituted with methionine or leucine; or the amino acid at the position corresponding to position 267 of the amino acid sequence of SEQ ID NO: 1 is substituted with methionine or leucine.

[9] The HbA1c dehydrogenase according to [5], wherein the amino acid at the position corresponding to position 280 of the amino acid sequence of SEQ ID NO: 1 is substituted with glutamine;

the amino acid at the position corresponding to position 269 of the amino acid sequence of SEQ ID NO: 1 is substituted with methionine or leucine; or the amino acid at the position corresponding to position 267 of the amino acid sequence of SEQ ID NO: 1 is substituted with methionine or leucine.

[10] The HbA1c dehydrogenase according to any one of [3] to [9], wherein the oxidase activity is reduced to less than 60% that of the amadoriase prior to modification (100%) or the ratio of oxidase activity to dehydrogenase activity (OX/DH) is reduced to less than 40% that of the amadoriase prior to modification (100%).

[11] The HbA1c dehydrogenase according to any one of [3] to [10], wherein the amadoriase is derived from the genus Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium, or Arthrobacter.

[12] The HbA1c dehydrogenase according to any one of [3] to [11], which comprises the amino acid sequence of any of SEQ ID NO: 1, SEQ ID NOs: 3 to 14, and SEQ ID NOs: 16 to 26 and has the amino acid substitution as defined in any of [3] to [9].

[13] The HbA1c dehydrogenase according to any one of [3] to [12], wherein, when the amino acid sequence of the HbA1c dehydrogenase is aligned with the amino acid sequence of SEQ ID NO: 1, one or more amino acids at positions corresponding to the positions selected from the group consisting of the positions indicated below of the amino acid sequence of SEQ ID NO: 1 is(are) substituted or deleted, and the HbA1c dehydrogenase is capable of directly acting on hemoglobin A1c and has dehydrogenase activity:

(A) substitution at positions 62, 63, 102, 106, 110, 113, 355, 419, 68, 356, 64, and/or 99;

(B) substitution at positions 262, 257, 249, 253, 337, 340, 232, 129, 132, 133, 44, 256, 231, and/or 81; and (C) deletion of 3 amino acid residues at positions 435, 436, and 437 from the carboxyl terminus.

[14] The HbA1c dehydrogenase according to [13], wherein, when the amino acid sequence of the HbA1c dehydrogenase is aligned with the amino acid sequence of SEQ ID NO: 1, one or more amino acids at positions corresponding to the positions selected from the group consisting of the positions indicated below of the amino acid sequence of SEQ ID NO: 1 is(are) substituted or deleted, and the HbA1c dehydrogenase is capable of directly acting on hemoglobin A1c and has dehydrogenase activity:

(A) substitution of the amino acid at the position corresponding to arginine at position 62 with alanine, asparagine, or aspartic acid, substitution of the amino acid at the position corresponding to leucine at position 63 with histidine or alanine, substitution of the amino acid at the position corresponding to glutamic acid at position 102 with lysine, substitution of the amino acid at the position corresponding to aspartic acid at position 106 with alanine, lysine, or arginine, substitution of the amino acid at the position corresponding to glutamine at position 110 with leucine or tyrosine, substitution of the amino acid at the position corresponding to alanine at position 113 with lysine or arginine, substitution of the amino acid at the position corresponding to alanine at position 355 with serine, substitution of the amino acid at the position corresponding to alanine at position 419 with lysine, substitution of the amino acid at the position corresponding to aspartic acid at position 68 with asparagine, substitution of the amino acid at the position corresponding to alanine at position 356 with threonine, substitution of the amino acid at the position corresponding to arginine at position 64 with glycine, serine, methionine, leucine, threonine, valine, or isoleucine, and substitution of the amino acid at the position corresponding to histidine at position 99 with serine;

(B) substitution of the amino acid at the position corresponding to asparagine at position 262 with histidine, substitution of the amino acid at the position corresponding to valine at position 257 with cysteine, serine, or threonine, substitution of the amino acid at the position corresponding to glutamic acid at position 249 with lysine or arginine, substitution of the amino acid at the position corresponding to glutamic acid at position 253 with lysine or arginine, substitution of the amino acid at the position corresponding to glutamine at position 337 with lysine or arginine, substitution of the amino acid at the position corresponding to glutamic acid at position 340 with proline, substitution of the amino acid at the position corresponding to aspartic acid at position 232 with lysine or arginine, substitution of the amino acid at the position corresponding to aspartic acid at position 129 with lysine or arginine, substitution of the amino acid at the position corresponding to aspartic acid at position 132 with lysine or arginine, substitution of the amino acid at the position corresponding to glutamic acid at position 133 with alanine, methionine, lysine, or arginine, substitution of the amino acid at the position corresponding to glutamic acid at position 44 with proline, substitution of the amino acid at the position corresponding to glycine at position 256 with lysine or arginine, substitution of the amino acid at the position corresponding to glutamic acid at position 231 with lysine or arginine, and substitution of the amino acid at the position corresponding to glutamic acid at position 81 with lysine or arginine; and (C) deletion of 3 amino acids at positions corresponding to proline at position 435, lysine at position 436, and leucine at position 437 from the carboxyl terminus.

[15] A reagent kit for measurement of HbA1c comprising the HbA1c dehydrogenase according to any one of [3] to [14].

[16] An enzyme electrode comprising the HbA1c dehydrogenase according to any one of [3] to [14].

[17] An enzyme sensor comprising the enzyme electrode according to [16] as a working electrode.

[18] The method for measurement according to [1] or [2], wherein the HbA1c dehydrogenase is the HbA1c dehydrogenase according to any one of [3] to [14].

This description includes the content as disclosed in the description and/or drawings of Japanese Patent Application No. 2016-086592, which is a priority document of the present application.

Effects of the Invention

The present invention can provide an amadoriase with excellent properties that can be used as a diagnostic enzyme for diabetes capable of measuring HbA1c without applying a protease or the like, is less susceptible to oxygen, and is capable of measurement with high sensitivity and for a sensor for measurement of a diabetes marker as well as a gene encoding such enzyme. With the use of such amadoriase, glycated hemoglobin can be measured with higher accuracy even in the presence of oxygen without applying a protease or the like.

BRIEF DESCRIPTION OF THE DRAWINGS

FIG. 1-1 shows examples of identical and similar amino acids in amino acid sequences of various known amadoriases. Co, Et, Py, Ar, Cc, Nv, Cn, Pn, An, En, Ul, and Pj are aligned.

FIG. 1-2 is a continuation of FIG. 1-1.
FIG. 1-3 is a continuation of FIG. 1-2.
FIG. 1-4 is a continuation of FIG. 1-3.
FIG. 1-5 is a continuation of FIG. 1-4.
FIG. 2-1 shows examples of identical and similar amino acids in amino acid sequences of various known amadoriases. In addition to the amadoriases shown in FIG. 1, Ao2, Af2, At, Fo, Ao1, Af1, Pi, and Dh are aligned.

FIG. 2-2 is a continuation of FIG. 2-1.
FIG. 2-3 is a continuation of FIG. 2-2.
FIG. 2-4 is a continuation of FIG. 2-3.
FIG. 2-5 is a continuation of FIG. 2-4.
FIG. 2-6 is a continuation of FIG. 2-5.
FIG. 2-7 is a continuation of FIG. 2-6.
FIG. 2-8 is a continuation of FIG. 2-7.

FIG. 2-9 is a continuation of FIG. 2-8.

FIG. 2-10 is a continuation of FIG. 2-9.

FIG. 3 shows oxidase activity and dehydrogenase activity of an amadoriase. FIG. 3 is merely a schematical illustration to explain enzyme reactions, and does not restrict properties, such as substrate specificity, of the enzyme.

FIG. 4 shows the results of HbA1c measurement using A1cDH.

FIG. 5 shows the results of plotting the current responses at various HbA1c concentrations.

EMBODIMENTS FOR CARRYING OUT THE INVENTION

Figure 3:
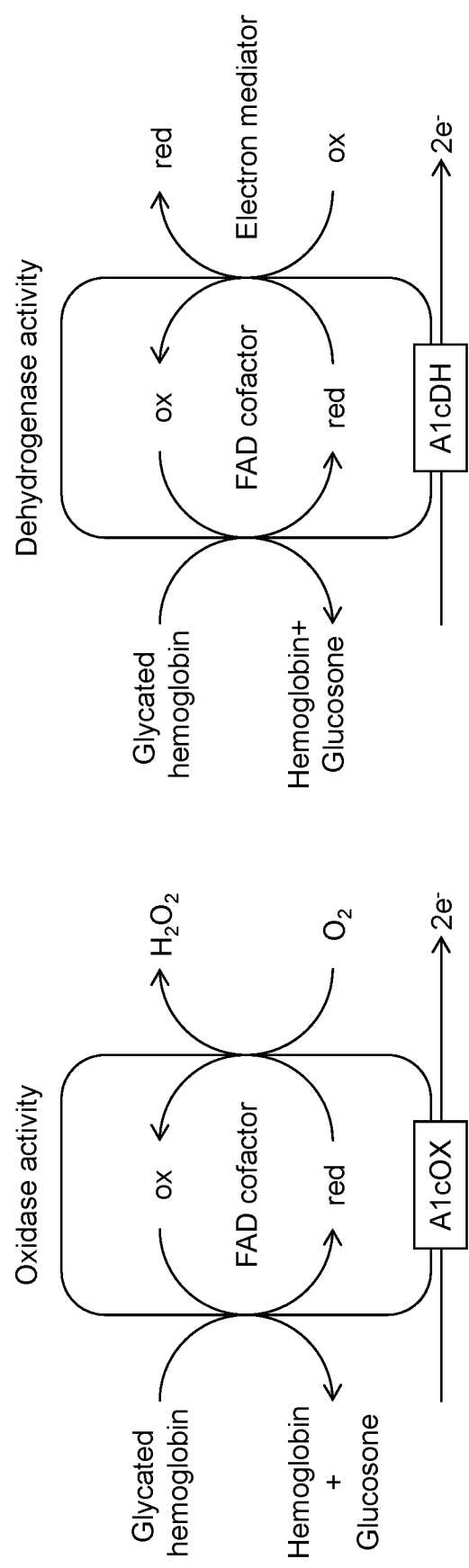

Hereafter, the present invention is described in detail.

The amadoriase according to the present invention can recognize a glycated protein or a glycated peptide as a substrate.

(Glycated Protein and Hemoglobin A1c)

The term "glycated protein" used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.

(Glycated Peptide and Fructosyl Peptide)

The term "glycated peptide" used herein refers to a non-enzymatically-glycated peptide derived from a glycated protein. Peptides that are directly and non-enzymatically glycated, products of degradation of glycated proteins by a protease or the like, and products of glycation of (poly) peptides constituting glycated proteins are included in glycated peptides. A "glycated peptide" is also referred to as a "fructosyl peptide." Regarding glycated proteins, examples of amino groups in the glycated peptide side chain include an amino terminal α-amino group and a ε-amino group in the lysine side chain within a peptide. However, in the present invention, the glycated peptide is, more specifically, an α-glycated peptide (α-fructosyl peptide). An α-glycated peptide is released and formed from a glycated protein having a glycated N-terminal α-amino acid by an arbitrary means, such as limited degradation with a protease or the like. Where the glycated protein of interest is hemoglobin A1c (HbA1c), for example, the α-glycated peptide is a glycated peptide cleaved from the HbA1c β-chain having the glycated N terminus. The HbA1c β-chain composed of 146 amino acids also falls under an α-glycated peptide (αF146P).

In one embodiment, the target substance (i.e., the substrate) on which the amadoriase of the present invention acts is HbA1c and more specifically the β-chain of HbA1c. In another embodiment, the target substance on which the amadoriase of the present invention acts is α-glycated peptide cleaved from the 3-chain of HbA1c, such as αFV to αF1281P, αFV to αF64P, αFV to αF32P, or αFV to αF16P. More specifically, it is α-fructosyl-valyl-histidyl-leucyl-threonyl-proryl-glutamic acid (αF6P). In another embodiment, the target substance on which the amadoriase of the present invention acts is α-fructosyl-valyl-histidine (αFVH) or α-fructosyl valine (αFV).

(Amadoriase)

An amadoriase is also referred to as ketoamine oxidase, fructosyl amino acid oxidase, fructosyl peptide oxidase, or fructosyl amine oxidase. An amadoriase is an enzyme that catalyzes the reaction which oxidizes iminodiacetic acid or a derivative thereof (Amadori compound) in the presence of oxygen to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

(Hba1c Oxidase)

Among various types of amadoriases, an amadoriase that has activity of recognizing HbA1c as a substrate and directly oxidizing HbA1c is referred to herein as "HbA1c oxidase", and may also be referred to as "A1cOX." An amadoriase that directly acts on HbA1c can be obtained based on, for example, WO 2015/060429. Such amadoriase can also be obtained based on WO 2015/005257. The descriptions thereof are incorporated herein by reference in their entirety. HbA1c oxidase may comprise one or more amino acid substitutions described in such known documents. Further, a mutation that alters substrate specificity or the like may be introduced into a known HbA1c oxidase.

Examples of possible amino acid substitutions in an amadoriase that directly acts on HbA1c include the following amino acid substitutions at positions corresponding to the positions of the amino acid sequence of SEQ ID NO: 1 described below:

(a) position 62 (arginine);
(b) position 63 (leucine);
(c) position 102 (glutamic acid);
(d) position 106 (aspartic acid);
(e) position 110 (glutamine);
(f) position 113 (alanine);
(g) position 355 (alanine);
(h) position 419 (alanine);
(i) position 68 (aspartic acid);
(j) position 356 (alanine).
(k) position 64 (arginine); and
(l) position 99 (histidine).

In such a case, preferably, (a) the amino acid at the position corresponding to position 62 of SEQ ID NO: 1 may be substituted with asparagine, alanine, aspartic acid, glutamine, glutamic acid, glycine, valine, leucine, isoleucine, cysteine, serine, methionine, threonine, or proline. Preferably, (b) the amino acid at the position corresponding to position 63 of SEQ ID NO: 1 may be substituted with histidine, alanine, or glycine. Preferably, (c) the amino acid at the position corresponding to position 102 of SEQ ID NO: 1 may be substituted with lysine. Preferably, (d) the amino acid at the position corresponding to position 106 of SEQ ID NO: 1 may be substituted with alanine, lysine, or arginine. Preferably, (e) the amino acid at the position corresponding to position 110 of SEQ ID NO: 1 may be substituted with leucine, tyrosine, phenylalanine, or histidine. Preferably, (f) the amino acid at the position corresponding to position 113 of SEQ ID NO: 1 may be substituted with lysine or arginine. Preferably, (g) the amino acid at the position corresponding to position 355 of SEQ ID NO: 1 may be substituted with serine. Optionally, (h) the amino acid at the position corresponding to position 419 of SEQ ID NO: 1 may be substituted with lysine. Optionally, (i) the amino acid at the position corresponding to position 68 of SEQ ID NO: 1 may be substituted with asparagine. Optionally, (j) the amino acid at the position corresponding to position 356 of SEQ ID NO: 1 may be substituted with threonine. Optionally, (k) the amino acid at the position corresponding to position 64 of SEQ ID NO: 1 may be substituted with glycine, serine, methionine, leucine, threonine, valine, or isoleucine. Optionally, (1) the amino acid at the position corresponding to position 99 of SEQ ID NO: 1 may be substituted with serine.

According to a particular embodiment, apart from or in addition to the mutations indicated above, the HbA1c oxidase may comprise one or more amino acid substitutions at positions indicated below or positions corresponding thereto:

(l) position 67 of SEQ ID NO: 1;
(m) position 72 of SEQ ID NO: 1;
(n) position 76 of SEQ ID NO: 1;
(o) position 96 of SEQ ID NO: 1;
(p) position 109 of SEQ ID NO: 1; and
(q) position 116 of SEQ ID NO: 1.

Optionally, (l) the amino acid at the position corresponding to position 67 of SEQ ID NO: 1 may be histidine. Optionally, (m) the amino acid at the position corresponding to position 72 of SEQ ID NO: 1 may be serine. Optionally, (n) the amino acid at the position corresponding to position 76 of SEQ ID NO: 1 may be alanine or phenylalanine. Optionally, (o) the amino acid at the position corresponding to position 96 of SEQ ID NO: 1 may be glutamic acid. Optionally, (p) the amino acid at the position corresponding to position 109 of SEQ ID NO: 1 may be arginine or lysine. Optionally, (q) the amino acid at the position corresponding to position 116 of SEQ ID NO: 1 may be arginine.

Mutations at the positions described above (i.e., positions 62, 63, 102, 106, 110, 113, 355, 419, 68, 356, 64, and 99 as well as positions 67, 72, 76, 96, 109, and 116) are examples of mutations that alter substrate specificity of an amadoriase. However, these are merely examples and mutations that alter substrate specificity are not limited thereto. In one embodiment, the amadoriase of the present invention comprises one or a plurality of mutations that alter substrate specificity.

(HbA1c Dehydrogenase According to the Present Invention)

In one embodiment, the present invention provides an HbA1c dehydrogenase. An HbA1c dehydrogenase can be prepared by introducing the mutation according to the present invention into an amadoriase. In one embodiment, an HbA1c dehydrogenase can be obtained based on an HbA1c oxidase (A1cOX). Examples of HbA1c oxidases include, but are not limited to, those described above and any HbA1c oxidase can be used, provided that the same can recognize HbA1c as a substrate and directly oxidize HbA1c. In another embodiment, a mutation according to the present invention can be introduced into an amadoriase to prepare an amadoriase with enhanced dehydrogenase activity, and then a mutation that alters substrate specificity can be introduced thereto in order to prepare an HbA1c dehydrogenase that directly acts on HbA1c.

The term "HbA1c dehydrogenase" used herein refers to an amadoriase that acts on HbA1c and has enhanced dehydrogenase activity, lowered oxidase activity, enhanced dehydrogenase activity and lowered oxidase activity, or a lower ratio of oxidase activity to dehydrogenase activity (OX/DH), compared with the (parent) amadoriase prior to the introduction of the mutation(s) of the present invention. It should be noted that this does not exclude (prohibit) the HbA1c dehydrogenase according to the present invention from having oxidase activity. An amadoriase that does not recognize HbA1c as a substrate at all; i.e., an amadoriase that does not act on HbA1c at all, is not encompassed within the scope of the HbA1c dehydrogenase according to the present invention.

In one embodiment, the HbA1c dehydrogenase according to the present invention is an HbA1c dehydrogenase prepared based on the amadoriase derived from the genus *Coniochaeta* (SEQ ID NO: 1). In one embodiment, the HbA1c dehydrogenase according to the present invention is an HbA1c dehydrogenase prepared based on the amadoriase derived from *Eupenicillium terrenum* (SEQ ID NO: 3), the ketoamine oxidase derived from *Pyrenochaeta* sp. (SEQ ID NO: 4), the ketoamine oxidase derived from *Arthrinium* sp. (SEQ ID NO: 5), the ketoamine oxidase derived from *Curvularia clavata* (SEQ ID NO: 6), the ketoamine oxidase derived from *Neocosmospora vasinfecta* (SEQ ID NO: 7), the fructosyl amino acid oxidase derived from *Cryptococcus neoformans* (SEQ ID NO: 8), the fructosyl peptide oxidase derived from *Phaeosphaeria nodorum* (SEQ ID NO: 9), the fructosyl amino acid oxidase derived from *Aspergillus nidulans* (SEQ ID NO: 10), the fructosyl peptide oxidase derived from *Emericella nidulans* (SEQ ID NO: 11), the fructosyl amino acid oxidase derived from *Ulocladium* sp. (SEQ ID NO: 12), the fructosyl amino acid oxidase derived from *Penicillium janthinellum* (SEQ ID NO: 13), the amadoriase Ao2 derived from *Aspergillus oryzae* (SEQ ID NO: 19), the amadoriase Aft derived from *Aspergillus fumigatus* (SEQ ID NO: 20), the amadoriase At derived from *Aspergillus terreus* (SEQ ID NO: 21), the amadoriase Fo derived from *Fusarium oxysporum* (SEQ ID NO: 22), the amadoriase Ao1 derived from *Aspergillus oryzae* (SEQ ID NO: 23), the amadoriase Af1 derived from *Aspergillus fumigatus* (SEQ ID NO: 24), the amadoriase Pi derived from *Pichia* sp. (SEQ ID NO: 25), or the amadoriase Dh derived from *Debaryomyces hansenii* (SEQ ID NO: 26) or an equivalent of any thereof.

Examples of such HbA1c dehydrogenases include an amadoriase comprising an amino acid sequence having a high degree of sequence identity with any of SEQ ID NO: 1, SEQ ID NOs: 3 to 14, and SEQ ID NOs: 16 to 26 (e.g., 30% or higher, 35% or higher, 40% or higher, 45% or higher, 50% or higher, 55% or higher, 60% or higher, 65% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher) and an amadoriase comprising an amino acid sequence derived from any of SEQ ID NO: 1, SEQ ID NOs: 3 to 14, and SEQ ID NOs: 16 to 26 having deletion, substitution, addition, and/or insertion of one or several amino acids.

The HbA1c dehydrogenase according to the present invention may be prepared based on, for example, an amadoriase derived from an organism species belonging to the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium, Arthrobacter,* or *Debaryomyces*. In particular, an HbA1c dehydrogenase acting on HbA1c, having dehydrogenase activity, and comprising an amino acid sequence having a high degree of sequence identity with the sequence of any of SEQ ID NO: 1, SEQ ID NOs: 3 to 14, and SEQ ID NOs: 16 to 26 as described above is preferable.

An HbA1c dehydrogenase can be obtained by substitution, addition, or deletion of at least 1 amino acid residue in the amino acid sequence of an HbA1c oxidase.
(Substitution for Enhancing Dehydrogenase Activity or Lowering Oxidase Activity)

Examples of amino acid substitutions for enhancing dehydrogenase activity and/or lowering oxidase activity include substitutions of amino acids at positions corresponding to the positions of the amino acid sequence of SEQ ID NO: 1 described below. Such amino acid substitution may also be referred to as a mutation that enhances dehydrogenase activity according to the present invention, a mutation that lowers oxidase activity according to the present invention, a mutation that enhances dehydrogenase activity and/or lowers oxidase activity according to the present invention, or simply a mutation or substitution according to the present invention.

(1) Substitution at the position corresponding to position 280 with, for example, a polar amino acid selected from the group consisting of glutamine, serine, threonine, and asparagine, a charged amino acid selected from the group consisting of aspartic acid, glutamic acid, lysine, arginine, and histidine, or an amino acid selected from the group consisting of methionine, proline, phenylalanine, tyrosine, and tryptophan.

(2) Substitution at the position corresponding to position 267 with, for example, a hydrophobic amino acid residue selected from the group consisting of tyrosine, leucine, methionine, tryptophan, isoleucine, valine, cysteine, and alanine.

(3) Substitution at the position corresponding to position 269 with, for example, a hydrophobic amino acid residue selected from the group consisting of tyrosine, leucine, methionine, tryptophan, isoleucine, valine, cysteine, and alanine.

(4) Substitution at the position corresponding to position 54 with, for example, asparagine, alanine, glutamine, histidine, glycine, or valine.

(5) Substitution at the position corresponding to position 241 with, for example, glutamine, lysine, glutamic acid, asparagine, aspartic acid, arginine, or histidine.

For convenience of description, glutamine, serine, threonine, and asparagine may be referred to herein as "polar amino acid(s)". Further, aspartic acid, glutamic acid, lysine, arginine, and histidine may be referred to as "charged amino acid(s)." Further, alanine, cysteine, valine, isoleucine, leucine, methionine, phenylalanine, tyrosine, and tryptophan may be referred to as "hydrophobic amino acid(s)." Furthermore, methionine, phenylalanine, tyrosine, tryptophan, and proline may be referred to as "bulky amino acid(s)."

The HbA1c dehydrogenase according to the present invention may comprise at least 1 or a plurality of the amino acid substitutions described above. For example, such dehydrogenase comprises the amino acid substitution (1), (2), (3), (4), or (5) described above.

In particular, a variant comprising an amino acid substitution at a position corresponding to the amino acid position described below and having enhanced dehydrogenase activity and lowered oxidase activity is preferable:

(1) Substitution at the position corresponding to position 280 with, for example, glutamine, serine, histidine, threonine, aspartic acid, glutamic acid, methionine, lysine, arginine, or asparagine.

(2) Substitution at the position corresponding to position 267 with, for example, tyrosine, leucine, or methionine.

(3) Substitution at the position corresponding to position 269 with, for example, tyrosine, leucine, or methionine.

(4) Substitution at the position corresponding to position 54 with, for example, asparagine or alanine.

(5) Substitution at the position corresponding to position 241 with, for example, glutamine, lysine, or glutamic acid.

The HbA1c dehydrogenase according to the present invention may comprise an amino acid substitution for enhancing dehydrogenase activity and/or lowering oxidase activity at positions corresponding to the positions of the amino acid sequence of SEQ ID NO: 1. Further, the HbA1c dehydrogenase according to the present invention may comprise deletion, insertion, addition, and/or substitution of one or several amino acids (e.g., 1 to 30, 1 to 20, or 1 to 15, such as 1 to 10, preferably 1 to 5, more preferably 1 to 3, and particularly preferably 1) at positions other than the amino acid substitutions mentioned above. The present invention further encompasses an amadoriase variant that results from amino acid substitution for enhancing dehydrogenase activity and/or lowering oxidase activity and amino acid substitution for improving properties other than properties for enhancing dehydrogenase activity, such as substrate specificity, said variant comprising an amino acid sequence having amino acid sequence identity of, for example, 30% or higher, 35% or higher, 40% or higher, 45% or higher, 50% or higher, 55% or higher, 60% or higher, 65% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher between the amino acid sequence in regions other than the amino acid substitutions described above and the amino acid sequence of any of SEQ ID NO: 1, SEQ ID NOs: 3 to 14, and SEQ ID NOs: 16 to 26, directly acting on HbA1c, and having modified dehydrogenase activity.

An amadoriase having the amino acid sequence of SEQ ID NO: 1 is an amadoriase (CFP-T7) derived from the genus *Coniochaeta* produced by *E. coli* harboring a recombinant plasmid referred to as "pKK223-3-CFP-T7" in WO 2007/125779 (Accession Number: FERM BP-10593), which is a modified amadoriase with excellent heat stability previously discovered by the present inventors. CFP-T7 is a triple variant obtained by successively introducing artificial mutations into positions 272, 302, and 388 of a naturally-occurring amadoriase derived from the genus *Coniochaeta*.

CFP-T7-H35 disclosed in WO 2015/060429 results from introduction of amino acid substitutions R62D, L63H, E102K, D106K, Q110L, A113K, and A355S into CFP-T7. CFP-T7-H37 (SEQ ID NO: 14) results from introduction of mutations D68N/A356T into CFP-T7-H35.

Concerning the amino acid substitutions described above, while an amino acid position indicates a position in the amino acid sequence of the amadoriase derived from the genus *Coniochaeta* of SEQ ID NO: 1, with regard to amino acid sequences of amadoriases derived from other organisms, the amino acid at the position corresponding to the position of the amino acid sequence of SEQ ID NO: 1 is substituted. The meaning of the expression "position corresponding to ( . . . )" is described below.

(Additional Substitution)
(Amino Acid Substitution that Enhances Surfactant Tolerance of Amadoriase)

The present inventors reported that surfactant tolerance of an amadoriase can be enhanced by substitution of amino acid residues thereof (see, for example, WO 2015/020200, incorporated herein by reference in its entirety).

Examples of amino acid substitutions that enhance surfactant tolerance of an amadoriase include substitutions of amino acids at positions corresponding to the positions of the amino acid sequence of SEQ ID NO: 1 described below:
  (i) position 262;
  (ii) position 257;
  (iii) position 249;
  (iv) position 253;
  (v) position 337;
  (vi) position 340;
  (vii) position 232;
  (viii) position 129;
  (ix) position 132;
  (x) position 133;
  (xi) position 44;
  (xii) position 256;
  (xiii) position 231; and
  (xiv) position 81.

Optionally, the amino acid at the position corresponding to position 262 may be substituted with histidine. Optionally, the amino acid at the position corresponding to position 257 may be substituted with cysteine, serine, or threonine. Optionally, the amino acid at the position corresponding to position 249 may be substituted with lysine or arginine. Optionally, the amino acid at the position corresponding to position 253 may be substituted with lysine or arginine. Optionally, the amino acid at the position corresponding to position 337 may be substituted with lysine or arginine. Optionally, the amino acid at the position corresponding to position 340 may be substituted with proline. Optionally, the amino acid at the position corresponding to position 232 may be substituted with lysine or arginine. Optionally, the amino acid at the position corresponding to position 129 may be substituted with lysine or arginine. Optionally, the amino acid at the position corresponding to position 132 may be substituted with lysine or arginine. Optionally, the amino acid at the position corresponding to position 133 may be substituted with alanine, methionine, lysine, or arginine. Optionally, the amino acid at the position corresponding to position 44 may be substituted with proline. Optionally, the amino acid at the position corresponding to position 256 may be substituted with lysine or arginine. Optionally, the amino acid at the position corresponding to position 231 may be substituted with lysine or arginine. Optionally, the amino acid at the position corresponding to position 81 may be substituted with lysine or arginine.

In this description, mutations at these positions (i.e., positions 44, 133, 253, 257, 262, 337, and 340 as well as positions 249, 232, 129, 132, 256, 231, and 81) may also be referred to as mutations that enhance surfactant tolerance of an amadoriase. In one embodiment, the amadoriase according to the present invention may comprise a mutation that further enhances surfactant tolerance.

(Amino Acid Deletion that Improves Heat Stability of the Amadoriase)

The present inventors previously reported that heat stability of an amadoriase can be improved by deletion of 3 amino acid residues from the carboxyl terminus thereof (see WO 2013/100006, incorporated herein by reference in its entirety). In one embodiment, the amadoriase of the present invention may comprise deletion of 3 amino acid residues from the carboxyl terminus thereof, in addition to the substitution described above. The term "deletion of 3 amino acid residues from the carboxyl terminus" used herein may be referred to as deletion that improves heat stability.

(Obtaining Genes Encoding Amadoriases)

In order to obtain genes encoding amadoriases according to the present invention described above (hereinafter, also merely referred to as "amadoriase genes"), generally used gene cloning methods can be used. For example, chromosomal DNA or mRNA can be extracted from a microorganism fungus body or various cells having the ability to produce an amadoriase by conventional techniques, such as the method described in "Current Protocols in Molecular Biology" (WILEY Interscience, 1989). In addition, cDNA can be synthesized using mRNA as the template. A chromosomal DNA or cDNA library can be constructed using the chromosomal DNA or cDNA obtained in such a manner.

Subsequently, DNA including the entire sequence of a target amadoriase gene can be obtained by a method of synthesizing an appropriate probe DNA based on the amino acid sequence of the amadoriase mentioned above and selecting an amadoriase gene from a chromosomal DNA or cDNA library using the probe DNA. Alternatively, an appropriate primer DNA may be designed based on the amino acid sequence mentioned above, DNA including the target gene fragment encoding the amadoriase gene may be amplified by an appropriate polymerase chain reaction (PCR) technique, such as the 5' RACE or 3' RACE method, and the resulting DNA fragments may then be linked to obtain DNA comprising the entire length of the amadoriase gene of interest.

A preferable example of a gene encoding an amadoriase thus obtained is an amadoriase gene derived from the genus *Coniochaeta* (JP 2003-235585 A).

The amadoriase genes are preferably linked to various vectors using conventional techniques from the perspective of handling. Examples include the recombinant plasmid pKK223-3-CFP (JP 2003-235585 A) prepared by inserting DNA encoding the amadoriase gene derived from the *Coniochaeta* sp. NISL 9330 strain into the pKK223-3 vector (GE Healthcare).

(Vector)

Vectors that can be used in the present invention are not limited to the plasmid vectors above. For example, any other vector known in the art, such as bacteriophage or cosmid vectors, can be used. In particular, for example, pBluescriptII SK+ (manufactured by Stratagene Corporation) is preferable.

(Mutation of Amadoriase Gene)

Mutation of an amadoriase gene can be performed by any known method depending on the intended form of mutation. More specifically, methods of bringing a chemical mutagen into contact with and allowing to act on an amadoriase gene or recombinant DNA comprising such gene integrated therein, ultraviolet application methods, genetic engineering techniques, methods making extensive use of protein engineering techniques, or various other methods can be extensively used.

Examples of chemical mutagens used in the mutation mentioned above include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the drug mentioned above at concentrations of from 0.5 M to 12 M. The ultraviolet application may also be performed according to conventional techniques as described above (Gendai Kagaku, pp. 24-30, June, 1989).

As the method making extensive use of protein engineering techniques, in general, a technique known as site-specific mutagenesis can be used. Examples include the Kramer method (Nucleic Acids Res., 12, 9441, 1984; Methods Enzymol., 154, 350, 1987; and Gene, 37, 73, 1985), the Eckstein method (Nucleic Acids Res., 13, 8749, 1985; Nucleic Acids Res., 13, 8765, 1985; and Nucleic Acids Res, 14, 9679, 1986), and the Kunkel method (Proc. Natl. Acid. Sci. U.S.A., 82, 488, 1985; and Methods Enzymol., 154, 367, 1987). Examples of a specific method of conversion of a nucleotide sequence in DNA include the use of a commercially available kit (Transformer Mutagenesis Kit, Clonetech; EXOIII/Mung Bean Deletion Kit, Stratagene; or Quick Change Site Directed Mutagenesis Kit, Stratagene).

The technique known as the general polymerization chain reaction (PCR) technique can also be used (Technique, 1, 11, 1989). In addition to the conventional genetic mutation techniques above, the modified amadoriase genes of interest can also be directly synthesized by an organic synthesis method or enzyme synthesis method.

The nucleotide sequences of DNA of the amadoriase genes obtained by the methods mentioned above may be determined or verified by, for example, using a multi-capillary DNA analysis system, CEQ2000 (Beckman Coulter Inc.) or Applied Biosystems 3130xl genetic analyzer (Thermo Fisher Scientific).

(Transformation/Transduction)

The amadoriase genes obtained as described above may be integrated into a vector such as a bacteriophage vector, a cosmid vector, or a plasmid vector used in transformation of a prokaryotic or eukaryotic cell by a conventional technique, and a host corresponding to each vector can be transformed or transduced by conventional techniques. For example, a host of interest, such as a microorganism belonging to the genus *Escherichia*, which specifically may be a strain of *E. coli* K-12, preferably a strain of *E. coli* JM109, *E. coli* DH5a (manufactured by Takara Bio Inc.), a strain of *E. coli* B, or preferably a strain of *E. coli* BL21 (manufactured by NIPPON GENE CO., LTD.) may be transformed using the obtained recombinant DNA, or such recombinant DNA may be transduced into the host cells, so as to obtain the resulting strain.

(Amino Acid Sequence Identity or Similarity)

The amino acid sequence identity or similarity can be computed by a program such as maximum matching or search homology of GENETYX Ver. 11 (manufactured by GENETYX) or a program such as maximum matching or multiple alignment of DNASIS Pro (manufactured by Hitachi Solutions, Ltd.). In order to compute amino acid sequence identity, two or more amadoriases may be aligned, and the positions of identical amino acids in such two or more amadoriases may be determined. The identical regions in amino acid sequences can be determined based on such information.

Further, positions having similar amino acids in two or more amadoriases may be examined. For example, a plurality of amino acid sequences can be subjected to alignment using CLUSTALW and, in such case, Blosum62 can be used as the algorithm and a plurality of amino acid sequences can be subjected to alignment and amino acids determined to be similar as a result of such alignment may be referred to as "similar amino acids." In the variant of the present invention, amino acid substitution can be carried out between such similar amino acids. By carrying out such alignments, it is possible to examine regions having identical amino acid sequences and positions being occupied by similar amino acids regarding a plurality of amino acid sequences. Based on such information, homologous regions (conserved regions) in the amino acid sequences can be determined.

The term "homologous region(s)" used herein refers to region(s) consisting of identical or similar amino acids at corresponding positions in the reference amadoriase and in the comparative amadoriase, when two or more amadoriases are aligned, wherein the region(s) consist(s) of 3 or more, 4 or more, 5 or more, 6 or more, 7 or more, 8 or more, 9 or more, or 10 or more continuous amino acids. For example, FIG. 1 shows the alignment of amadoriases having 74% or higher sequence identity over the full-length amino acid sequences. In such sequences, the region of positions 10 to 32 with reference to the sequence of the amadoriase derived from *Coniochaeta* sp. of SEQ ID NO: 1 consists of identical or similar amino acids, and, therefore, such region falls under a homologous region. Similarly, regions of positions 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. of SEQ ID NO: 1 can be (can fall under) homologous regions.

Preferably, the homologous region of an amadoriase is the region consisting of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. of SEQ ID NO: 1.

More preferably, the homologous region of an amadoriase is the region consisting of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. of SEQ ID NO: 1.

The HbA1c dehydrogenase according to the present invention comprises an amino acid sequence having, when aligned with the amadoriase comprising an amino acid sequence of any of SEQ ID NO: 1, SEQ ID NOs: 3 to 14, and SEQ ID NOs: 16 to 26, for example, 30% or higher, 35% or higher, 40% or higher, 45% or higher, 50% or higher, 55% or higher, 60% or higher, 65% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher amino acid sequence identity over the full length; is capable of directly acting on HbA1c; and has dehydrogenase activity. In addition, the amino acid sequence of the homologous region of the HbA1c dehydrogenase according to the present invention exhibits, for example, 70% or higher, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher sequence identity with the amino acid sequence of the homologous region of SEQ ID NO: 1.

The term "conserved region(s)" used herein refers to a region(s) consisting of identical or similar amino acids at corresponding positions in the reference amadoriase and in the comparative amadoriase, when two or more amadoriases are aligned. For example, FIG. 2 shows the alignment of amadoriases having 30% or higher sequence identity over the full-length amino acid sequences. In such sequence, the positions 11, 12, 13, 15, 17, 18, 20, 22, 23, 24, 25, 27, 29, 31, 36, 37, 41, 46, 47, 50, 51, 52, 54, 56, 57, 58, 75, 79, 82, 84, 85, 93, 95, 149, 158, 159, 162, 165, 166, 177, 180, 202, 208, 218, 220, 221, 222, 224, 228, 233, 239, 243, 246, 250, 255, 258, 260, 266, 267, 270, 272, 277, 278, 280, 281, 282, 284, 285, 286, 318, 321, 326, 329, 334, 339, 346, 347, 348, 351, 352, 354, 358, 359, 362, 363, 370, 373, 376, 382, 385, 386, 389, 406, 407, 409, 418, 425, and 427 consist of the identical or similar amino acids with reference to the sequence of the amadoriase derived from Coniochaeta sp. of SEQ ID NO: 1 and, therefore, fall under the conserved region. With reference to the sequence of the amadoriase derived from Coniochaeta sp. of SEQ ID NO: 1, similarly, the positions 15, 17, 18, 20, 22, 23, 24, 25, 27, 29, 31, 41, 46, 47, 51, 52, 54, 56, 57, 79, 82, 93, 149, 158, 159, 162, 177, 180, 202, 208, 221, 222, 233, 243, 250, 258, 266, 267, 270, 278, 280, 282, 284, 285, 318, 334, 347, 348, 351, 362, 363, 373, 376, 386, 407, 409, and 418 consist of the identical or similar amino acids and, therefore, fall under the conserved region.

It should be noted that the homologous region(s) and the conserved region(s) described above are regions of amino acid sequences of naturally-occurring amadoriases. Corresponding amino acids in such homologous region or conserved region of the modified amadoriases derived from a naturally-occurring amadoriase via introduction of various mutations may be substituted. Amino acids in such regions need not be necessarily identical or similar to each other after modification.

In one embodiment, for example, a modified amadoriase (e.g., HbA1c oxidase) can be prepared from a naturally-occurring amadoriase via introduction of a mutation. Subsequently, the mutation according to the present invention can be introduced into the modified amadoriase to prepare HbA1c dehydrogenase. In such case, sequence identity between the conserved regions should not be determined between the amino acid sequence of SEQ ID NO: 1 and that of the modified amadoriase. Rather, sequence identity should be determined between the amino acid sequence of SEQ ID NO: 1 and that of the naturally-occurring amadoriase from which the modified amadoriase is derived.

Accordingly, sequence identity between the amino acid sequence in the conserved region of a naturally-occurring amadoriase from which the HbA1c dehydrogenase according to the present invention is derived and the amino acid sequence of a conserved region of SEQ ID NO: 1 may, for example, be 70% or higher, 75% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher. For example, sequence identity is 100% in one embodiment. In addition, the HbA1c dehydrogenase according to the present invention comprises an amino acid sequence having, when aligned with the amino acid sequence of an amadoriase of any of SEQ ID NO: 1, SEQ ID NOs: 3 to 14, and SEQ ID NOs: 16 to 26, for example, 30% or higher, 35% or higher, 40% or higher, 45% or higher, 50% or higher, 55% or higher, 60% or higher, 65% or higher, 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, or 99% or higher sequence identity over the full length; directly acts on HbA1c; and has dehydrogenase activity.

(Identification of Corresponding Positions)

The term (the) "position corresponding to" a given position refers to the position in an amino acid sequence of an amadoriase derived from another organism species that corresponds to the amino acid at a particular position in the amino acid sequence of an amadoriase derived from the genus Coniochaeta of SEQ ID NO: 1, unless otherwise specified. The term "corresponding position" used herein may also be referred to as "equivalent position." Further, the "amino acid at a position corresponding to" a particular position optionally may be referred to as a "corresponding amino acid."

A method of identifying a "corresponding position" in another amino acid sequence relative to a particular position in a given amino acid sequence can be performed by, for example, comparing amino acid sequences using a known algorithm such as the Lipman-Pearson method to assign maximum identity to conserved amino acid residues present in the amino acid sequence of each amadoriase. By aligning the amino acid sequences of the amadoriases by such method, the positions of the homologous amino acid residues in each of the amadoriase sequences can be determined, regardless of insertion or deletion of amino acid residues in the amino acid sequences. Homologous positions are considered to exist at the same positions in the three-dimensional structures, and amino acid residues at such homologous positions are expected to exert similar effects in terms of specificity of the amadoriase of interest.

FIGS. 1 and 2 show sequences of amadoriases derived from various types of known organism species. The amino acid sequence of SEQ ID NO: 1 is shown on the uppermost line. Various sequences shown in FIG. 1 each have 70% or higher sequence identity with the sequence of SEQ ID NO: 1 and these sequences are aligned using a known algorithm. Various sequences shown in FIG. 2 each have 30% or higher sequence identity with the sequence of SEQ ID NO: 1 and these sequences are aligned using a known algorithm. Based on FIGS. 1 and 2, the sites of mutations in the amino acid sequence of the amadoriase derived from other organism species corresponding to the amino acid at the particular position in the amino acid sequence of the amadoriase belonging to the genus Coniochaeta can be identified. In addition, corresponding positions and corresponding amino acids in such corresponding positions can be identified. FIG. 1 shows amino acid sequences of the amadoriase belonging to the genus Coniochaeta (SEQ ID NO: 1), the amadoriase derived from Eupenicillium terrenum (SEQ ID NO: 3), the ketoamine oxidase derived from Pyrenochaeta sp. (SEQ ID NO: 4), the ketoamine oxidase derived from Arthrinium sp. (SEQ ID NO: 5), the ketoamine oxidase derived from Curvularia clavata (SEQ ID NO: 6), the ketoamine oxidase derived from Neocosmospora vasinfecta (SEQ ID NO: 7), the fructosyl amino acid oxidase derived from Cryptococcus neoformans (SEQ ID NO: 8), the fructosyl peptide oxidase derived from Phaeosphaeria nodorum (SEQ ID NO: 9), the fructosyl amino acid oxidase derived from *Aspergillus nidulans* (SEQ ID NO: 10), the fructosyl peptide oxidase derived from *Emericella nidulans* (SEQ ID NO: 11), the fructosyl amino acid oxidase derived from *Ulocladium* sp. (SEQ ID NO: 12), and the fructosyl amino acid oxidase derived from *Penicillium janthinellum* (SEQ ID NO: 13). FIG. 2 shows, in addition to the amino acid sequences of the amadoriase derived from the genus *Coniochaeta* (SEQ ID NO: 1) and the like shown in FIG. 1, amino acid sequences of the amadoriase Ao2 derived from *Aspergillus oryzae* (also designated FaoAo2; SEQ ID NO: 19), the amadoriase Aft derived from *Aspergillus fumigatus* (also designated Amadoriase II; SEQ ID NO: 20), the amadoriase At derived from *Aspergillus terreus* (also designated FAOD-A; SEQ ID NO: 21), the amadoriase Fo derived from *Fusarium oxysporum* (SEQ ID NO: 22), the amadoriase Ao1 derived from *Aspergillus oryzae* (also designated FaoAo 1; SEQ ID NO: 23), the amadoriase Af1 derived from *Aspergillus fumigatus* (also designated Amadoriase I; SEQ ID NO: 24), the amadoriase Pi derived from *Pichia* sp. (SEQ ID NO: 25), and the amadoriase Dh derived from *Debaryomyces hansenii* (SEQ ID NO: 26).

(Amino Acids at Positions Corresponding to Particular Positions)

The term "amino acid at the position corresponding to position 280 of the amino acid sequence of SEQ ID NO: 1" used herein refers to the amino acid at the position corresponding to position 280 in the amadoriase sequence of SEQ ID NO: 1, when the identified amino acid sequence of the amadoriase is compared with the amino acid sequence of the amadoriase derived from the genus *Coniochaeta* of SEQ ID NO: 1. Thus, the amino acid of interest can be identified based on FIG. 1 or 2 showing the amino acid sequences aligned by the method for identifying the "corresponding position" described above. The same applies to the amino acids at the positions corresponding to positions 267, 269, 54, and 241 of the amino acid sequence of SEQ ID NO: 1.

That is, the amino acid at the "position corresponding to position 280 of the amino acid sequence of SEQ ID NO: 1" is cysteine at position 280 in the amadoriase derived from *Eupenicillium terrenum*, cysteine at position 278 in the ketoamine oxidase derived from *Pyrenochaeta* sp., cysteine at position 280 in the ketoamine oxidase derived from *Arthrinium* sp., cysteine at position 278 in the ketoamine oxidase derived from *Curvularia clavata*, cysteine at position 280 in the ketoamine oxidase derived from *Neocosmospora vasinfecta*, cysteine at position 280 in the fructosyl amino acid oxidase derived from *Cryptococcus neoformans*, cysteine at position 276 in the fructosyl peptide oxidase derived from *Phaeosphaeria nodorum*, cysteine at position 280 in the fructosyl amino acid oxidase derived from *Aspergillus nidulans*, cysteine at position 280 in the fructosyl peptide oxidase derived from *Emericella nidulans*, cysteine at position 278 in the fructosyl amino acid oxidase derived from *Ulocladium* sp., and cysteine at position 280 in the fructosyl amino acid oxidase derived from *Penicillium janthinellum*.

In the sequences of SEQ ID NOs: 1 and 3 to 13, the positions corresponding to positions 280, 267, 269, 54, and 241 of the amino acid sequence of SEQ ID NO: 1 are as shown in the following table.

TABLE 1

| | Name | | | | | | |
|---|---|---|---|---|---|---|---|
| | CFP-T7 | EFP-T5 | PyFX | ArFX | CcFX | NvFX | CnFX |
| | | | | Origin | | | |
| aa | *Coniochaeta* sp. | *E. terrenum* | *Pyrenochaeta* sp. | *Arthrinium* sp. SEQ ID NO | *C. clavata* | *N. vasinfecta* | *C. neoformans* |
| position | SEQ 1 | SEQ 3 | SEQ 4 | SEQ 5 | SEQ 6 | SEQ 7 | SEQ 8 |
| 280 | C280 | C280 | C278 | C280 | C278 | C280 | C280 |
| 267 | F267 | F267 | F265 | F267 | F265 | F267 | F267 |
| 269 | F269 | F269 | F267 | F269 | F267 | F269 | F269 |
| 54 | D54 | D54 | D54 | D54 | D54 | D54 | D54 |
| 241 | Y241 | F241 | Y239 | Y241 | Y239 | Y241 | Y241 |

| | Name | | | | |
|---|---|---|---|---|---|
| | PnFX | AnFX | EnFX | UlFX | PjFX |
| | | | Origin | | |
| aa | *P. nodorum* | *A. nidulans* | *E. nidulans* SEQ ID NO | *Ulocladium* sp. | *P. janthinellum* |
| position | SEQ 9 | SEQ 10 | SEQ 11 | SEQ 12 | SEQ 13 |
| 280 | C276 | C280 | C280 | C278 | C280 |
| 267 | F263 | F267 | F267 | F265 | F267 |
| 269 | F265 | F269 | I269 | F267 | F269 |
| 54 | D54 | D53 | D53 | D54 | D54 |
| 241 | Y237 | F241 | F241 | Y239 | F241 |

For example, the amino acid at the position corresponding to position 267 of SEQ ID NO: 1 is phenylalanine at position 267 in the amadoriase derived from *Eupenicillium terrenum* (SEQ ID NO: 3). Other positions can also be identified with reference to the table above.

In addition, positions corresponding to positions 280, 267, 269, 54, and 241 of the amino acid sequence of SEQ ID NO: 1 with regard to the amadoriase Ao2 derived from *Aspergillus oryzae* (SEQ ID NO: 19), the amadoriase Aft derived from *Aspergillus fumigatus* (SEQ ID NO: 20), the amadoriase At derived from *Aspergillus terreus* (SEQ ID NO: 21), the amadoriase Fo derived from *Fusarium oxysporum* (SEQ ID NO: 22), the amadoriase Ao1 derived from *Aspergillus oryzae* (SEQ ID NO: 23), the amadoriase Af1 derived from *Aspergillus fumigatus* (SEQ ID NO: 24), the amadoriase Pi derived from *Pichia* sp. (SEQ ID NO: 25), and the amadoriase Dh derived from *Debaryomyces hansenii* (SEQ ID NO: 26) are as shown in the table below.

TABLE 2

| | | | | | Name | | | | |
|---|---|---|---|---|---|---|---|---|---|
| | CFP-T7 | Ao2 | Af2 | At | Fo | Ao1 | Af1 | Pi | Dh |
| | | | | | Origin | | | | |
| aa | *Coniochaeta* sp. | *A. oryzae* | *A. fumigatus* | *A. terreus* | *F. oxysporum* | *A. oryzae* | *A. fumigatus* | *Pichia* sp. | *D. hansenii* |
| | | | | | SEQ ID NO | | | | |
| position | SEQ 1 | SEQ 19 | SEQ 20 | SEQ 21 | SEQ 22 | SEQ 23 | SEQ 24 | SEQ 25 | SEQ 26 |
| 280 | C280 | C276 | C278 | C277 | C281 | C283 | C283 | C271 | C272 |
| 267 | F267 | F262 | F264 | F263 | F267 | F269 | F269 | F258 | F259 |
| 269 | F269 | F264 | F266 | F265 | M269 | M271 | M271 | F260 | F261 |
| 54 | D54 | D50 | D50 | D50 | D51 | D53 | D53 | D45 | D48 |
| 241 | Y241 | L236 | L238 | L237 | L241 | L243 | L243 | L232 | L233 |

In the table, for example, the amino acid at the position corresponding to position 280 of SEQ ID NO: 1 is cysteine at position 276 in amadoriase Ao2 derived from *Aspergillus oryzae* (SEQ ID NO: 19).

(Corresponding Positions of Mutations for Modification of Substrate Specificity)

In the present invention, the amino acid at "the position corresponding to position 62 of the amino acid sequence of SEQ ID NO: 1" is the amino acid corresponding to position 62 in the sequence of SEQ ID NO: 1, when the identified amino acid sequence of the amadoriase is compared with the amino acid sequence of SEQ ID NO: 1. Thus, the amino acid of interest can be identified based on FIGS. 1 and 2 showing the amino acid sequences aligned by the method described above. The same applies to the amino acids at the positions corresponding to positions 63, 102, 106, 110, 113, 355, 419, 68, 356, 64, 99, and further, to positions 262, 257, 249, 253, 337, 340, 232, 129, 132, 133, 44, 256, 231, and 81 of the amino acid sequence of SEQ ID NO: 1 indicated below.

In the sequences of SEQ ID NOs: 1 and 3 to 13, positions corresponding to the positions 62, 63, 102, 106, 110, 113, 355, 419, 68, 356, 64, and 99 of the amino acid sequence of SEQ ID NO: 1 are as shown in the table below.

TABLE 3

| | | | | Name | | | |
|---|---|---|---|---|---|---|---|
| | CFP-T7 | EFP-T5 | PyFX | ArFX | CcFX | NvFX | CnFX |
| | | | | Origin | | | |
| aa | *Coniochaeta* sp. | *E. terrenum* | *Pyrenochaeta* sp. | *Arthrinium* sp. | *C. clavata* | *N. vasinfecta* | *C. neoformans* |
| | | | | SEQ ID NO | | | |
| position | SEQ 1 | SEQ 3 | SEQ 4 | SEQ 5 | SEQ 6 | SEQ 7 | SEQ 8 |
| 62 | R62 | R62 | R62 | R62 | R62 | R62 | R62 |
| 63 | L63 | L63 | L63 | L63 | L63 | L63 | I63 |
| 102 | E102 | E102 | K102 | K102 | E102 | E102 | E102 |
| 106 | D106 | N106 | D106 | A106 | D106 | G106 | S106 |
| 110 | Q110 | K110 | A110 | Q110 | A110 | E110 | S110 |
| 113 | A113 | T113 | T113 | T113 | A113 | K113 | A113 |
| 355 | A355 | A355 | A353 | A356 | A353 | S355 | A355 |

TABLE 3-continued

| | | | | | | | |
|---|---|---|---|---|---|---|---|
| 419 | A419 | G419 | A418 | A421 | A418 | A420 | A420 |
| 68 | D68 | D68 | D68 | D68 | D68 | D68 | D68 |
| 356 | A356 | N356 | A354 | A357 | A354 | A356 | N356 |
| 64 | R64 | R64 | R64 | R64 | R64 | R64 | R64 |
| 99 | H99 | S99 | H99 | G99 | H99 | S99 | H99 |

| | Name | | | | |
|---|---|---|---|---|---|
| | PnFX | AnFX | EnFX | UlFX | PjFX |
| | | | Origin | | |
| aa | *P. nodorum* | *A. nidulans* | *E. nidulans* | *Ulocladium* sp. | *P. janthinellum* |
| | | | SEQ ID NO | | |
| position | SEQ 9 | SEQ 10 | SEQ 11 | SEQ 12 | SEQ 13 |
| 62 | S62 | R61 | R61 | R62 | R62 |
| 63 | L63 | L62 | L62 | L63 | L63 |
| 102 | K102 | E101 | E101 | K102 | E102 |
| 106 | D106 | G105 | K105 | D106 | S106 |
| 110 | G110 | K109 | R109 | A110 | K110 |
| 113 | A113 | S112 | S112 | A113 | D113 |
| 355 | A351 | A355 | A355 | A353 | A355 |
| 419 | S416 | A420 | A420 | A418 | S419 |
| 68 | D68 | D67 | D67 | D68 | D68 |
| 356 | A352 | N356 | N356 | A354 | N356 |
| 64 | R64 | R63 | R63 | R64 | R64 |
| 99 | H99 | S98 | S98 | H99 | S99 |

In the sequences of the amadoriase Ao2 derived from *Aspergillus oryzae* (SEQ ID NO: 19), the amadoriase Af2 derived from *Aspergillus fumigatus* (SEQ ID NO: 20), the amadoriase At derived from *Aspergillus terreus* (SEQ ID NO: 21), the amadoriase Fo derived from *Fusarium oxysporum* (SEQ ID NO: 22), the amadoriase Ao1 derived from *Aspergillus oryzae* (SEQ ID NO: 23), the amadoriase Af1 derived from *Aspergillus fumigatus* (SEQ ID NO: 24), the amadoriase Pi derived from *Pichia* sp. (SEQ ID NO: 25), and the amadoriase Dh derived from *Debaryomyces hansenii* (SEQ ID NO: 26), positions corresponding to the positions 62, 63, 102, 106, 110, 113, 355, 419, 68, 356, 64, and 99 of the amino acid sequence of SEQ ID NO: 1 are as shown in the table below. In the table, there is no position corresponding to position 68 of SEQ ID NO: 1 concerning Dh. As such, with regard to Dh, the position corresponding to position 68 of SEQ ID NO: 1 is not selected as the position for amino acid substitution. The same applies to other positions for which corresponding positions are not defined.

TABLE 4

| | Name | | | | | | | |
|---|---|---|---|---|---|---|---|---|
| | CFP-T7 | Ao2 | Af2 | At | Fo | Ao1 | Af1 | Pi | Dh |
| | | | | | Origin | | | | |
| aa | *Coniochaeta* sp. | *A. oryzae* | *A. fumigatus* | *A. terreus* | *F. oxysporum* | *A. oryzae* | *A. fumigatus* | *Pichia* sp. | *D. hansenii* |
| | | | | | SEQ ID NO | | | | |
| position | SEQ 1 | SEQ 19 | SEQ 20 | SEQ 21 | SEQ 22 | SEQ 23 | SEQ 24 | SEQ 25 | SEQ 26 |
| 62 | R62 | G58 | G58 | G58 | L59 | R61 | S61 | D53 | T56 |
| 63 | L63 | Q59 | Q59 | Q59 | S60 | E62 | E62 | Y54 | S57 |
| 102 | E102 | A104 | E104 | E104 | K107 | S109 | A109 | A98 | E96 |
| 106 | D106 | R108 | R108 | R108 | Q111 | H113 | H113 | H102 | S100 |
| 110 | Q110 | R112 | R112 | R112 | D115 | H117 | D117 | Y106 | R104 |
| 113 | A113 | P115 | P115 | P115 | G118 | D120 | E120 | E109 | Y107 |
| 355 | A355 | R341 | R343 | R342 | R347 | R350 | R350 | M332 | R332 |
| 419 | A419 | F410 | F412 | F411 | F416 | F419 | F419 | W400 | Y404 |
| 68 | D68 | K64 | K64 | K64 | K65 | E67 | S67 | A59 | — |
| 356 | A356 | E342 | E344 | E343 | M348 | A351 | A351 | Q333 | H333 |
| 64 | R64 | Y60 | Y60 | Y60 | T61 | V63 | L63 | V55 | D58 |
| 99 | H99 | C101 | C101 | T101 | S104 | H106 | H106 | S95 | T93 |

(Corresponding Positions of Mutations for Improvement of Surfactant Tolerance)

In the sequences of SEQ ID NOs: 1 and 3 to 13, positions corresponding to the positions 44, 133, 253, 257, 262, 337, 340, 249, 232, 129, 132, 256, 231, and 81 of the amino acid sequence of SEQ ID NO: 1 are as shown in the table below.

TABLE 5

| | Name | | | | | | |
|---|---|---|---|---|---|---|---|
| | CFP-T7 | EFP-T5 | PyFX | ArFX | CcFX | NvFX | CnFX |
| | | | | Origin | | | |
| aa | Coniochaeta sp. | E. terrenum | Pyrenochaeta sp. | Arthrinium sp. | C. clavata | N. vasinfecta | C. neoformans |
| | | | | SEQ ID NO | | | |
| position | SEQ 1 | SEQ 3 | SEQ 4 | SEQ 5 | SEQ 6 | SEQ 7 | SEQ 8 |
| 44 | E44 | K44 | P44 | P44 | P44 | P44 | L44 |
| 133 | E133 | E133 | E133 | A133 | E133 | A133 | E133 |
| 253 | E253 | A253 | A251 | E253 | E251 | V253 | E253 |
| 257 | V257 | V257 | T255 | C257 | V255 | C257 | C257 |
| 262 | N262 | D262 | N260 | H262 | N260 | H262 | N262 |
| 337 | Q337 | K337 | K335 | Q338 | T335 | K337 | K337 |
| 340 | E340 | E340 | E338 | E341 | E338 | P340 | E340 |
| 249 | E249 | K249 | K247 | H249 | E247 | E249 | E249 |
| 232 | D232 | D232 | D230 | E232 | D230 | E232 | G232 |
| 129 | D129 | E129 | D129 | D129 | D129 | D129 | S129 |
| 132 | D132 | D132 | D132 | D132 | D132 | E132 | D132 |
| 256 | G256 | N256 | D254 | G256 | N254 | G256 | E256 |
| 231 | E231 | E231 | E229 | E231 | E229 | E231 | E231 |
| 81 | E81 | N81 | E81 | H81 | E81 | N81 | N81 |

| | Name | | | | |
|---|---|---|---|---|---|
| | PnFX | AnFX | EnFX | UlFX | PjFX |
| | | | Origin | | |
| aa | P. nodorum | A. nidulans | E. nidulans | Ulocladium sp. | P. janthinellum |
| | | | SEQ ID NO | | |
| position | SEQ 9 | SEQ 10 | SEQ 11 | SEQ 12 | SEQ 13 |
| 44 | P44 | P43 | P43 | P44 | P44 |
| 133 | E131 | E132 | E132 | K133 | D133 |
| 253 | R249 | A253 | A253 | E251 | Q253 |
| 257 | S253 | T257 | T257 | V255 | V257 |
| 262 | N258 | D262 | D262 | N260 | D262 |
| 337 | K333 | N337 | N337 | T335 | K337 |
| 340 | K336 | E340 | E340 | E338 | E340 |
| 249 | E245 | A249 | A249 | S247 | Q249 |
| 232 | E228 | E232 | E232 | D230 | D232 |
| 129 | D127 | E128 | E128 | D129 | E129 |
| 132 | D130 | D131 | D131 | D132 | D132 |
| 256 | N252 | N256 | N256 | N254 | G256 |
| 231 | H227 | E231 | E231 | Q229 | E231 |
| 81 | E81 | N80 | N80 | E81 | N81 |

In the sequences of the amadoriase Ao2 derived from Aspergillus oryzae (SEQ ID NO: 19), the amadoriase Af2 derived from Aspergillus fumigatus (SEQ ID NO: 20), the amadoriase At derived from Aspergillus terreus (SEQ ID NO: 21), the amadoriase Fo derived from Fusarium oxysporum (SEQ ID NO: 22), the amadoriase Ao1 derived from Aspergillus oryzae (SEQ ID NO: 23), the amadoriase Af1 derived from Aspergillus fumigatus (SEQ ID NO: 24), the amadoriase Pi derived from Pichia sp. (SEQ ID NO: 25), and the amadoriase Dh derived from Debaryomyces hansenii (SEQ ID NO: 26), positions corresponding to the positions 44, 133, 253, 257, 262, 337, 340, 249, 232, 129, 132, 256, 231, and 81 of the amino acid sequence of SEQ ID NO: 1 are as shown in the table below.

TABLE 6

| | | | | Name | | | | |
|---|---|---|---|---|---|---|---|---|
| | CFP-T7 | Ao2 | Af2 | At | Fo | Ao1 | Af1 | Pi | Dh |
| | | | | | Origin | | | | |
| aa | Coniochaeta sp. | A. oryzae | A. fumigatus | A. terreus | F. oxysporum | A. oryzae | A. fumigatus | Pichia sp. | D. hansenii |
| | | | | | SEQ ID NO | | | | |
| position | SEQ 1 | SEQ 19 | SEQ 20 | SEQ 21 | SEQ 22 | SEQ 23 | SEQ 24 | SEQ 25 | SEQ 26 |
| 44 | E44 | T40 | P40 | P40 | R41 | P43 | P43 | P35 | A38 |
| 133 | E133 | Q131 | K132 | Q131 | K135 | K137 | R137 | E127 | K126 |
| 253 | E253 | L248 | L250 | Q249 | L253 | K255 | Q255 | A244 | L245 |
| 257 | V257 | L252 | I254 | M253 | L257 | L259 | L259 | L248 | M249 |
| 262 | N262 | N257 | N259 | N258 | N262 | N264 | N264 | N253 | N254 |
| 337 | Q337 | A323 | A325 | A324 | A329 | A332 | A332 | A314 | A314 |
| 340 | E340 | P326 | P328 | P327 | P332 | P335 | P335 | P317 | E317 |
| 249 | E249 | E244 | E246 | E245 | E249 | D251 | E251 | E240 | D241 |
| 232 | D232 | D227 | N229 | D228 | N232 | K234 | K234 | R223 | Q224 |
| 129 | D129 | E127 | E128 | E127 | E131 | E133 | E133 | E123 | E122 |
| 132 | D132 | R130 | R131 | R130 | R134 | R136 | R136 | R126 | E125 |
| 256 | G256 | N251 | N253 | N252 | N256 | N258 | N258 | S247 | G248 |
| 231 | E231 | K226 | K228 | K227 | E231 | K233 | K233 | Q222 | E223 |
| 81 | E81 | T83 | N83 | N83 | H86 | N88 | T88 | T77 | E75 |

(Corresponding Positions of Deletions for Improvement of Heat Stability)

The term "positions corresponding to 3 amino acid residues at the carboxyl terminus of the amadoriase sequence of SEQ ID NO: 1" used herein refers to 3 amino acid residues corresponding to the 3 amino acid residues at the carboxyl terminus of the amino acid sequence of SEQ ID NO: 1, when the amino acid sequence of the target amadoriase is compared with the amino acid sequence of an amadoriase derived from SEQ ID NO: 1. The sequence comprising 3 residues at these positions in the amadoriase sequence derived from the genus *Coniochaeta* comprises proline at position 435, lysine at position 436, and leucine at position 437, and the amino acid sequence at positions corresponding thereto can be identified based on FIGS. 1 and 2 showing the amino acid sequences aligned in the manner described above.

Incidentally, in the case of eukaryotes, the "peroxisome targeting signal 1 (PTS1) sequence", which is a signal sequence for transporting a protein to the peroxisome and is a motif composed of 3 amino acids at the carboxyl terminus, is known. Well-known conventional PTS1 motifs include a motif composed of the sequence: (proline/serine/alanine/cysteine)-(lysine/histidine/arginine/asparagine)-(leucine/methionine) (see, for example, FEBS J., 272, 2362, 2005, Plant Cell Physiol., 38, 759, 1997, and Eur. J. Cell Biol., 71, 248, 1996). According to such finding, the region of "positions corresponding to 3 amino acid residues at the carboxyl terminus of the amadoriase sequence of SEQ ID NO: 1" corresponds to the so-called PTS1 motif of an amadoriase. Accordingly, in one embodiment, the "positions corresponding to 3 amino acid residues at the carboxyl terminus of the amadoriase sequence of SEQ ID NO: 1" can also be understood as the "positions corresponding to the PTS1 motif."

Specifically, 3 amino acid residues at the carboxyl terminus of the amadoriase derived from *Eupenicillium terrenum* consist of alanine at position 435, histidine at position 436, and leucine at position 437, 3 amino acid residues at the carboxyl terminus of the ketoamine oxidase derived from *Pyrenochaeta* sp. consist of alanine at position 438, lysine at position 439, and leucine at position 440; 3 amino acid residues at the carboxyl terminus of the ketoamine oxidase derived from *Arthrinium* sp. consist of histidine at position 450, lysine at position 451, and leucine at position 452; 3 amino acid residues at the carboxyl terminus of the ketoamine oxidase derived from *Curvularia clavata* consist of serine at position 438, lysine at position 439, and leucine at position 440; 3 amino acid residues at the carboxyl terminus of the fructosyl peptide oxidase derived from *Phaeosphaeria nodorum* consist of alanine at position 435, asparagine at position 436, and leucine at position 437; 3 amino acid residues at the carboxyl terminus of the fructosyl amino acid oxidase derived from *Aspergillus nidulans* consist of alanine at position 436, lysine at position 437, and methionine at position 438; 3 amino acid residues at the carboxyl terminus of the fructosyl peptide oxidase derived from *Emericella nidulans* consist of alanine at position 436, lysine at position 437, and methionine at position 438; 3 amino acid residues at the carboxyl terminus of the fructosyl amino acid oxidase derived from *Ulocladium* sp. consist of alanine at position 439, lysine at position 440, and leucine at position 441; and 3 amino acid residues at the carboxyl terminus of the fructosyl amino acid oxidase derived from *Penicillium janthinellum* consist of alanine at position 435, lysine at position 436, and leucine at position 437.

Incidentally, in one embodiment, the "positions corresponding to 3 amino acid residues at the carboxyl terminus of the amadoriase sequence of SEQ ID NO: 1;" i.e., the "positions corresponding to the PTS1 motif," may, by nature, lack the one residue on the C terminus side (leucine/methionine). For example, in the ketoamine oxidase derived from *Neocosmospora vasinfecta*, the "positions corresponding to 3 amino acid residues at the carboxyl terminus of the amadoriase sequence of SEQ ID NO: 1;" i.e., the "positions corresponding to the PTS1 motif," are composed of serine at position 440 and arginine at position 441. As for the fructosyl amino acid oxidase derived from *Cryptococcus neoformans*, it is considered that the positions corresponding to 3 amino acid residues at the carboxyl terminus of the amadoriase sequence of SEQ ID NO: 1 do not exist.

In the sequences of the amadoriase Ao2 derived from *Aspergillus oryzae* (SEQ ID NO: 19), the amadoriase Aft derived from *Aspergillus fumigatus* (SEQ ID NO: 20), the amadoriase At derived from *Aspergillus terreus* (SEQ ID NO: 21), the amadoriase Fo derived from *Fusarium oxysporum* (SEQ ID NO: 22), the amadoriase Ao1 derived from

*Aspergillus oryzae* (SEQ ID NO: 23), the amadoriase Af1 derived from *Aspergillus fumigatus* (SEQ ID NO: 24), the amadoriase Pi derived from *Pichia* sp. (SEQ ID NO: 25), and the amadoriase Dh derived from *Debaryomyces hansenii* (SEQ ID NO: 26), the "positions corresponding to 3 amino acid residues at the carboxyl terminus of the amadoriase sequence of SEQ ID NO: 1;" i.e., the "positions corresponding to the PTS1 motif," are as shown in the table below. With regard to Pi, position 427 may also be deleted when deleting positions 424, 425, and 426 (deletion of 4 amino acid residues from the carboxyl terminus). For convenience of description, deletion of 4 amino acid residues from the carboxyl terminus of Pi is encompassed within the scope of deletion of 3 amino acid residues from the carboxyl terminus of the amadoriase sequence of SEQ ID NO: 1. Positions for which a corresponding position with reference to SEQ ID NO: 1 are not defined are not be selected as the position for amino acid deletion.

the aid of streptomycin sulfate, protamine sulfate, or manganese sulfate, according to need. Ammonium sulfate, alcohol, or acetone is added to the solution, so as to fractionate the solution, and sediments are then collected to obtain the crude enzymes of the amadoriases.

A purified amadoriase enzyme preparation can be obtained from the crude enzyme of the amadoriase mentioned above by a method appropriately selected from among: gel filtration methods using Sephadex, Superdex, or Ultrogel; adsorption-elution methods using ion exchange carriers; electrophoretic methods using polyacrylamide gels, etc.; adsorption-elution methods using hydroxyapatite; sedimentation methods such as sucrose density-gradient centrifugation; affinity chromatography methods; and fractionation methods using a molecular sieve membrane, a hollow-fiber membrane, etc. Alternatively, the methods mentioned above can adequately be performed in combination, so as to obtain a purified amadoriase enzyme preparation. Thus, the amadoriase of interest having enhanced dehydrogenase activity can be obtained.

Amadoriases contained in the kit according to the present invention can be naturally-occurring amadoriases derived from the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium,* or *Arthrobacter* or variants thereof. Such variants comprise one or more amino acid substitutions at positions corresponding to amino acids selected from the group consisting of cysteine at position 280, phenylalanine at position 267, phenylalanine at position 269, aspartic acid at position 54, and tyrosine at position 241 of the amino acid sequence of SEQ ID NO: 1. A person skilled in the art can readily determine whether or not a certain type of amadoriase or a variant thereof can be used for the kit according to the present invention (i.e., whether or not such amadoriase has dehydrogenase activity of interest) by, for example, the test method described below.

TABLE 7

| | | | | | Name | | | | |
|---|---|---|---|---|---|---|---|---|---|
| | CFP-T7 | Ao2 | Af2 | At | Fo | Ao1 | Af1 | Pi | Dh |
| | | | | | Origin | | | | |
| aa | *Coniochaeta* sp. | *A. oryzae* | *A. fumigatus* | *A. terreus* | *F. oxysporum* | *A. oryzae* | *A. fumigatus* | *Pichia* sp. | *D. hansenii* |
| | | | | | SEQ ID NO | | | | |
| position | SEQ 1 | SEQ 19 | SEQ 20 | SEQ 21 | SEQ 22 | SEQ 23 | SEQ 24 | SEQ 25 | SEQ 26 |
| 435 | P435 | A434 | S436 | S435 | — | S443 | — | H424 | S424 |
| 436 | K436 | K435 | K437 | K436 | — | R444 | — | K425 | H425 |
| 437 | L437 | L436 | L438 | L437 | — | L445 | — | L426 | L426 |

(Production of the Amadoriase of the Present Invention)

In order to produce the amadoriase of the present invention using a strain having the capability to produce such amadoriase obtained as described above, the strain may be cultured by a conventional solid culture method while liquid culture is preferably adopted where possible.

Examples of media to culture the strains mentioned above include media prepared by adding one or more inorganic salts selected from among, for example, sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

It is appropriate to adjust the initial pH of the media to 7 to 9. Culture can be performed under any conditions. For example, culture can be performed at 20° C. to 42° C., preferably at about 30° C. for 4 to 24 hours, and more preferably at about 30° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove the solid content, and nucleic acid is removed with (Enhanced Dehydrogenase Activity of the Amadoriase According to the Present Invention)

The amadoriase according to the present invention obtained has lowered oxidase activity and/or enhanced dehydrogenase activity, compared with the amadoriase prior to modification as a result of mutation of its amino acid sequence via genetic modification or other means. More specifically, the ratio of "oxidase activity" to "dehydrogenase activity" is lower than that prior to modification. The term "oxidase activity" refers to activity that transfers an electron to an oxygen molecule when oxidizing the substrate. The term "dehydrogenase activity" refers to activity that transfers a hydride ($H^-$) to an electron acceptor when oxidizing the substrate.

Low oxidase activity is desirable in order to reduce influence of oxygen when measuring glycated hemoglobin using a sensor. On the other hand, from the perspective of reactivity with the substrate, high dehydrogenase activity is desirable. That is, a low OX/DH ratio (i.e., a ratio of oxidase activity (OX) to dehydrogenase activity (DH)) of the amadoriase) is preferable and a low oxidase activity and high dehydrogenase activity (DH) of the amadoriase is preferable for the measurement of glycated hemoglobin using electron mediators. For the convenience of description, properties of an amadoriase may be described in terms of DH/OX indicating the ratio of dehydrogenase activity to oxidase activity or OX/DH indicating the ratio of oxidase activity to dehydrogenase activity herein. In one embodiment, the modified amadoriase of the present invention has enhanced dehydrogenase activity compared with that prior to modification. In one embodiment, the modified amadoriase of the present invention has lowered oxidase activity compared with that prior to modification. In one embodiment, the modified amadoriase of the present invention has a low ratio of oxidase activity to dehydrogenase activity (i.e., a high DH/OX ratio), compared with that prior to modification. In one embodiment, the modified amadoriase of the present invention has enhanced dehydrogenase activity and lowered oxidase activity, compared with those prior to modification. Specifically, the modified amadoriase according to the present invention preferably has a DH/OX ratio, indicating the ratio of dehydrogenase activity to oxidase activity, of 1.3 times or greater, 2 times or greater, 3 times or greater, 4 times or greater, 5 times or greater, 10 times or greater, 20 times or greater, 30 times or greater, 40 times or greater, 50 times or greater, 100 times or greater, 200 times or greater, 300 times or greater, 400 times or greater, or 450 times or greater than that prior to modification (i.e., 1.0 times). Further, the modified amadoriase according to the present invention preferably has an OX/DH ratio, indicating the ratio of oxidase activity to dehydrogenase activity, of less than 90%, less than 80%, less than 75%, less than 50%, less than 40%, less than 31%, less than 30%, less than 20%, less than 10%, less than 5%, less than 4.5%, less than 4%, less than 3.6%, less than 3%, less than 2%, less than 1%, less than 0.5%, or, for example, less than 0.2% compared to the OX/DH ratio prior to modification (100%).

The ratio of oxidase activity to dehydrogenase activity can be measured under any conditions using conventional methods of amadoriase activity measurement and the results can be compared with those prior to modification. For example, the oxidase activity measured at pH 7.0 with the addition of 1 mM of a certain type of glycated substrate, such as αFV, can be divided by the dehydrogenase activity measured with the addition of 1 mM of the glycated substrate, such as αFV, so as to determine the ratio. By this, the ratio of oxidase activity to dehydrogenase activity can be computed, and the computed ratios prior to modification and after modification may be compared. The substrate may be HbA1c or αF6P.

(High-Throughput Screening)

An amadoriase can further be subjected to high-throughput screening, so as to obtain a functional amadoriase variant (e.g., HbA1c dehydrogenase). For example, a library of a transformant or transductant comprising the transgenic amadoriase gene may be prepared and the resulting library may then be subjected to high-throughput screening using a microtiter plate. Alternatively, the library may be subjected to ultrahigh-throughput screening based on droplet microfluidics. For example, a combinatorial library of variant genes encoding variants can be constructed and a large population of variant amadoriases can be subjected to screening by means of phage display (e.g., Chem. Rev., 105 (11): 4056-72, 2005), yeast display (e.g., Comb. Chem. High Throughput Screen., 2008; 11(2): 127-34), or bacterial display (e.g., Curr. Opin. Struct. Biol., 17: 474-80, 2007). A reference may be made to Agresti et al, "Ultrahigh-throughput screening in drop-based microfluidics for directed evolution," Proceedings of the National Academy of Sciences, 107 (9): 4004-4009, March 2010. The description thereof concerning the technique for ultrahigh-throughput screening, which may be employed for screening of an amadoriase variant is incorporated herein by reference. For example, a library can be constructed by error-prone PCR. Alternatively, a mutation may be introduced into a target, which is a position described herein or position corresponding thereto, via saturation mutagenesis, so as to construct a library. Adequate cells, such as electrocompetent EBY-100 cells, can be transformed using a library and approximately $10^7$ variants can be obtained. Yeast cells transformed with the library can then be subjected to cell sorting. A polydimethoxylsiloxane (PDMS) microfluidic device prepared via standard soft-lithography may be used. Monodisperse droplets can be prepared using a flow-focusing device. The prepared droplets separately comprising variants can be applied to an adequate sorting device. Cells can be selected based on dehydrogenase activity. Mutagenesis and selection may be repeated a plurality of times.

When producing the HbA1c dehydrogenase according to the present invention, the order of introducing mutations is not particularly limited. It is also possible to first introduce a mutation for enhancing dehydrogenase activity according to the present invention into a starting amadoriase and then introduce a mutation for modification of substrate specificity or the like into the amadoriase having dehydrogenase activity and/or carry out screening if needed and the resultant can be made as a dehydrogenase that acts on HbA1c.

(Method for Measuring Amadoriase Activity)

Activity of an amadoriase comprises oxidase activity and dehydrogenase activity, and such activity can be measured via various techniques. An exemplary method for measuring amadoriase activity is described below.

In order to evaluate enzyme properties, glycated amino acid, such as HbA1c, αF6P, or fructosyl valine (FV), and a glycated peptide, such as fructosyl-valyl-histidine (FVH), can be used as the substrate. FV and FVH can be synthesized and purified in accordance with the method of Sakagami et al. (JP Patent Application Publication 2001-95598 A). A synthetic substrate (αF6P) can be used.

(Method for Measurement of Oxidase Activity Using αF6P as the Substrate)

Here, measurement of oxidase activity using αF6P as the substrate is described. In one embodiment, regarding enzyme titer, the amount of an enzyme capable of generating 1 μmol of hydrogen peroxide per minute can be defined as 1 U, when measurement is carried out using αF6P as the substrate. It should be noted that the definition above is merely for convenience of description of the methods for evaluating properties and measurements of enzymes and such definition does not indicate that the HbA1c dehydrogenase according to the present invention recognizes only αF6P as a substrate. The same applies to the method for measurement of dehydrogenase activity.

Preparation of Reagents (Reagent 1) 0.1 M phosphate buffer (pH 6.5) containing 5 U/ml peroxidase and 0.49 mm 4-aminoantipyrine Peroxidase (5.0 kU, manufactured by Kikkoman Corporation) and 100 mg of 4-aminoantipyrine (manufactured by Wako Pure Chemical Industries, Ltd.) are dissolved in a 0.1 M potassium phosphate buffer (pH 6.5), and the volume of the solution is fixed to 1,000 ml.

(Reagent 2) 15 mM TOOS solution

TOOS (N-ethyl-N-(2-hydroxy-3-sulfopropyl)-m-toluidine sodium, 500 mg, manufactured by Dojindo Laboratories) is dissolved in ion-exchange water, and the volume of the solution is fixed to 100 ml.

(Reagent 3) Substrate solution (30 mM; final concentration: 1 mM)

αF6P (257.1 mg, manufactured by Peptide Institute, Inc.) is dissolved in ion-exchange water, and the volume of the solution is fixed to 10 ml.

Method for Measurement

Reagent 1 (675 μl), 25 μl of Reagent 2, and 25 μl of an enzyme solution are mixed, and the mixture is preliminarily heated at 37° C. for 5 minutes. Subsequently, 25 μl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute ($\Delta As$) at 555 nm. A control solution is prepared in the manner described above, except that 25 μl of ion-exchange water is added instead of 25 μl of Reagent 3, and the change in absorbance per minute ($\Delta A0$) at 555 nm thereof is determined. The oxidase activity (U/ml) is calculated using the equation shown below.

$$\text{Oxidase activity (U/ml)} = \{(\Delta As - \Delta A0) \times 0.75 \times df\}/(39.2 \times 0.5 \times 0.025)$$

$\Delta As$: the change in absorbance of the reaction solution per minute $\Delta A0$: the change in absorbance of the control solution per minute 39.2: the millimole absorbance index of quinoneimine dye generated by the reaction ($mM^{-1} \cdot cm^{-1}$)

0.5: the number of moles of quinoneimine dye generated by 1 mol of hydrogen peroxide df: the dilution factor (Method for Measurement of Dehydrogenase Activity Using ααF6P as the Substrate)

Here, a method for measurement of dehydrogenase activity using αF6P as the substrate is described. Regarding the enzyme titer, in one embodiment, the amount of an enzyme capable of generating 1 μmol of a formazan dye per minute can be defined as 1 U, when measurement is carried out using αF6P as the substrate.

Preparation of Reagents (Reagent 4): 0.25 M Phosphate buffer (pH 6.5)
(Reagent 5): 10 mM WST-3 solution WST-3 (690 mg, 2-(4-iodophenyl)-3-(2,4-dinitrophenyl)-5-(2,4-disulfophenyl)-2H-tetrazolium, monosodium salt, manufactured by Dojindo Laboratories) is dissolved in ion-exchange water, and the volume of the solution is fixed to 100 ml.

(Reagent 6) 5.4 mM mPMS solution mPMS (180 mg, 1-methoxy-5-methylphenazinium methylsulfate, manufactured by Dojindo Laboratories) is dissolved in ion-exchange water, and the volume of the solution is fixed to 100 ml.

Method for Measurement

Reagent 4 (270 μl), Reagent 5 (150 μl), Reagent 6 (25 μl), ion-exchange water (255 μl), and an enzyme solution (25 μl) are mixed, and the mixture is preliminarily heated at 37° C. for 5 minutes. Subsequently, 25 μl of Reagent 3 is added, the resultant is thoroughly mixed, and the absorbance at 433 nm is then measured using a spectrophotometer (U-3010, manufactured by Hitachi High-Technologies). A control solution is prepared in the manner described above, except that 25 μl of ion-exchange water is added instead of 25 μl of the enzyme solution. Dehydrogenase activity (U/ml) is calculated using the equation shown below.

$$\text{Dehydrogenase activity (U/ml)} = \{(\Delta As - \Delta A0) \times 0.75 \times df\}/(31 \times 0.025)$$

$\Delta As$ the change in absorbance of the reaction solution per minute $\Delta A_0$: the change in absorbance of the control solution per minute 31: the millimole absorbance index of the formazan dye of WST-3 generated by the reaction ($mM^{-1} \cdot cm^{-1}$) df: the dilution factor (Method for Measurement of Dehydrogenase Activity Using HbA1c as the Substrate)

Here, a method for measurement of dehydrogenase activity using HbA1c as the substrate is described. In one embodiment, regarding the enzyme titer, the amount of an enzyme capable of generating 1 μmol of a formazan dye per minute can be defined as 1 U, when measurement is carried out using HbA1c as the substrate.

Preparation of Reagents (Reagent 7): 1.84 mg/ml HbA1c solution
(Reagent 8): 10% n-dodecyl-β-D-maltoside
(Reagent 9): 185 mM Phosphate buffer (pH 6.0)
(Reagent 5): 10 mM WST-3 solution Method for Measurement First, Reagent 7 (540 μl) is mixed with Reagent 8 (60 μl), and then the mixture is heated at 98° C. for 5 minutes to prepare an HbA1c sample pre-treatment solution. Subsequently, Reagent 5 (125 μl), an enzyme solution (62.5 μl), and ion-exchange water (7.5 μl) are mixed into Reagent 9 (305 μl), and the mixture is preliminarily heated at 37° C. for 5 minutes. Subsequently, the HbA1c sample pre-treatment solution (125 is mixed therewith, the mixture is agitated, and the absorbance at 433 nm is then measured using a spectrophotometer. A control experiment is performed with the addition of 62.5 μl of an amadoriase that does not act on HbA1c instead of 62.5 μl of the enzyme solution. Dehydrogenase activity (U/ml) is calculated using the equation shown below.

$$\text{Dehydrogenase activity (U/ml)} = \{(\Delta As - \Delta A0) \times 0.625 \times df\}/(31 \times 0.0625)$$

$\Delta As$: the change in absorbance of the reaction solution per minute $\Delta A_0$: the change in absorbance of the control solution per minute 31: the millimole absorbance index of the formazan dye of WST-3 generated by the reaction ($mM^{-1} \cdot cm^{-1}$)

df: the dilution factor (Reagent Kit, Sensor, and Method for Measurement)

In one embodiment, the present invention provides a kit for measurement of HbA1c and an apparatus for measurement of HbA1c comprising HbA1c dehydrogenase. This kit or apparatus may optionally comprise an electron mediator. In one embodiment, the present invention provides a method for measurement of HbA1c using HbA1c dehydrogenase.

In one embodiment, the present invention provides an enzyme electrode comprising an HbA1c dehydrogenase fixed thereto. In one embodiment, the HbA1c dehydrogenase may be applied, adsorbed, or fixed onto the enzyme electrode. In another embodiment, an electron mediator may also be applied, adsorbed, or fixed onto the electrode. Examples of electrodes that can be used include carbon electrodes and metal electrodes made of platinum, gold, silver, nickel, and palladium. Examples of materials constituting carbon electrodes include pyrolytic graphite carbon (PG), glassy carbon (GC), carbon paste, and plastic formed carbon (PFC). The measurement system may be a two-electrode system or a three-electrode system. For example, an enzyme can be fixed onto a working electrode. Examples of reference electrodes include standard hydrogen electrodes, reversible hydrogen electrodes, silver-silver chloride electrodes (Ag/AgCl), palladium-hydrogen electrodes, and saturated calomel electrodes. From the perspective of stability and reproducibility, Ag/AgCl is preferable.

An enzyme can be fixed onto an electrode via crosslinking, coating with the use of a dialysis membrane, embedding into a polymeric matrix, using a photocrosslinkable polymer, using an electroconductive polymer, using an oxidation-reduction polymer, or via other means. Alternatively, an enzyme may be fixed into a polymer or adsorbed and fixed onto an electrode together with an electron mediator. These techniques may be adopted in combination.

The HbA1c dehydrogenase according to the present invention can be used for various types of electrochemical measurement techniques using, for example, a potentiostat or galvanostat. Examples of electrochemical measurement techniques include various techniques, such as amperometry, potentiometry, and coulometry. For example, a current generated upon oxidation of the reduced mediator by an applied voltage can be measured via amperometry, so as to determine the concentration of the glycated substrate in the sample. While the voltage being applied varies depending on the conditions of a mediator or an apparatus, for example, the same can be −1000 to +1000 mV (v.s., Ag/AgCl).

HbA1c concentration can be measured in the manner described below. For example, a buffer is introduced into a temperature-controlled cell and the temperature is maintained at a constant level. Examples of mediators that can be used include potassium ferricyanide and phenazine methosulfate. As a working electrode, an electrode comprising the HbA1c dehydrogenase according to the present invention fixed thereon is used, and a counter electrode (e.g., a platinum electrode) and reference electrode (e.g., an Ag/AgCl electrode) are used. A certain level of voltage is applied to a carbon electrode, a sample comprising HbA1c is added after the current is stabilized, and an increased current is then measured. In accordance with a calibration curve prepared from HbA1c solutions at standard concentrations, the concentration of HbA1c in the sample can be calculated.

Further, in order to reduce the amount of a solution necessary for measurement, a printed electrode can be used. In such case, an electrode is preferably formed on an insulated substrate. Specifically, an electrode is preferably formed on a substrate by means of photolithography or printing techniques, such as screen printing, gravure printing, or flexography. Examples of materials constituting insulated substrates include silicon, glass, ceramics, polyvinyl chloride, polyethylene, polypropyrene, and polyester. Use of materials having high tolerance against various solvents or chemicals is more preferable.

In one embodiment, the present invention provides a sensor comprising the enzyme electrode.

In another embodiment, the concentration of the amadori compound in a sample can be determined by measuring a current generated upon an enzyme reaction using the enzyme electrode according to the present invention. For example, an enzyme electrode is used as a working electrode, and it is used together with a counter electrode and a reference electrode. A counter electrode can, for example, be a platinum electrode, and a reference electrode can, for example, be an Ag/AgCl electrode. While maintaining the temperature at a constant level, electrodes are introduced into a buffer containing a mediator. A voltage is applied to the working electrode, a sample is added thereto, and a change in the current is then measured.

Mediators used for the method, the kit, the apparatus, and the sensor for measurement according to the present invention (also referred to as an "artificial electron mediator," an "artificial electron acceptor," or an "electron mediator") are not particularly limited, provided that such mediators are capable of receiving electrons from the HbA1c dehydrogenase according to the present invention. Examples of mediators include, but are not limited to, quinones, phenazines, viologens, cytochromes, phenoxazines, phenothiazines, ferricyanides such as potassium ferricyanide, ferredoxins, ferrocenes, osmium complexes, and derivatives thereof, and examples of phenazine compounds include, but are not limited to, PMS and methoxy PMS. Unless specified otherwise, the term "electron mediator" used herein does not encompass oxygen or hydrogen peroxide.

In one embodiment, the HbA1c dehydrogenase according to the present invention has enhanced dehydrogenase activity, compared with the enzyme prior to modification. In one embodiment, the HbA1c dehydrogenase according to the present invention has lowered oxidase activity, compared with the enzyme prior to modification. In one embodiment, the HbA1c dehydrogenase according to the present invention has a lowered ratio of oxidase activity/dehydrogenase activity (OX/DH), compared with the enzyme prior to modification. In one embodiment, the HbA1c dehydrogenase according to the present invention has enhanced dehydrogenase activity and lowered oxidase activity, compared with the enzyme prior to modification. The enzyme reaction catalyzed by such HbA1c dehydrogenase according to the present invention is not influenced by oxygen, is not substantially influenced by oxygen, or is less likely to be influenced by oxygen. The HbA1c dehydrogenase according to the present invention can be used for the same applications (same use) as those of conventional amadoriases. Further, the HbA1c dehydrogenase according to the present invention can be used for measurement of the concentration of the glycated substrate, such as HbA1c, in a sample, and this can be utilized, for example, for diagnosis of diabetes. The amadoriase according to the present invention can also be used as an enzyme electrode. This can be utilized in various types of electrochemical measurement techniques. The HbA1c dehydrogenase according to the present invention can further be used as an enzyme sensor. Furthermore, the HbA1c dehydrogenase according to the present invention can be used for a kit for measuring a diabetes marker. In one embodiment, the present invention provides a method for measurement of hemoglobin A1c in a sample comprising allowing an HbA1c dehydrogenase capable of directly acting on hemoglobin A1c to act on a sample, and measuring a reduced electron mediator that is not hydrogen peroxide generated by such action or an oxidized electron mediator that is not oxygen consumed by such action. The measurement system may be a solution system or a dry system. In addition, measurement may be electrochemical measurement using an enzyme, enzyme electrode, or enzyme electrode for an enzyme sensor or the measurement may be absorbance measurement using a colorimetric substrate. It should be noted that the applications described above are examples and the use of the HbA1c dehydrogenase according to the present invention is not limited thereto.

EXAMPLES

Hereafter, the present invention is described in greater detail with reference to the examples, although the technical scope of the present invention is not limited to these examples.

Example 1

(Mutation for Enhancing Dehydrogenase Activity)
(1) Preparation of DNA of Recombinant Plasmid pKK223-3-CFP-T7-H38

SEQ ID NO: 14 shows the amino acid sequence of the enzyme (CFP-T7-H37) that is modified from the fructosyl peptide oxidase derived from Coniochaeta sp. to act on fructosyl hexapeptide. A strain of E. coli JM109 comprising the recombinant plasmid comprising the CFP-T7-H37 gene (SEQ ID NO: 15) (pKK223-3-CFP-T7-H37) (WO 2015/060429) was inoculated into 2.5 ml of LB-amp media (1% (w/v) bactotrypton, 0.5% (w/v) peptone, 0.5% (w/v) NaCl, and 50 µg/ml ampicillin) and shake culture was carried out at 37° C. for 20 hours to obtain a culture product.

The culture product was centrifuged at 7,000 rpm for 5 minutes to collect the cells. Subsequently, the recombinant plasmid pKK223-3-CFP-T7-H37 was extracted and purified therefrom using QIAGEN tip-100 (manufactured by QIAGEN), and 2.5 µl of DNA of the recombinant plasmid pKK223-3-CFP-T7-H37 was obtained.

(2) Site-Directed Modification Procedure of DNA of Recombinant Plasmid pKK223-3-CFP-T7-H37

PCR was carried out under the conditions described below using DNA of the recombinant plasmid pKK223-3-CFP-T7-H37 as the template, synthetic oligonucleotides of SEQ ID NOs: 27 and 28, and KOD-Plus- (Toyobo Co., Ltd.).

That is, 5 µl of 10× KOD-Plus- buffer, 5 µl of a dNTPs mixture in which each dNTP was adjusted at 2 mM, 2 µl of a 25 mM $MgSO_4$ solution, 50 ng of DNA of pKK223-3-CFP-T7 as the template, 15 pmol each of the synthetic oligonucleotides, and 1 unit of KOD-Plus-were mixed, and sterilized water was added thereto in order to bring the total amount of the solution to 50 µl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was subjected to electrophoresis on 1.0% agarose gel, and specific amplification of a DNA of about 6,000 bp was confirmed. The DNA obtained in such a manner was treated with a restriction enzyme DpnI (manufactured by New England Biolabs), the remaining template DNA was cleaved, strains of E. coli JM109 were transformed, and the transformants were then spread on LB-amp agar media. The grown colonies were inoculated into LB-amp media and shake-cultured therein, and plasmid DNA was isolated in the same manner as in (1) above. The nucleotide sequence of the DNA encoding the amadoriase in the plasmid was determined using a multi-capillary DNA analysis system (Applied Biosystems 3130xl Genetic Analyzer; manufactured by Life Technologies). As a result, the recombinant plasmid (pKK223-3-CFP-H38) encoding the modified amadoriase (SEQ ID NO: 16) resulting from substitution of arginine at position 64 with glycine of the amino acid sequence of SEQ ID NO: 14 was obtained.

Next, using the recombinant plasmid pKK223-3-CFP-H38 as the template, oligonucleotides of SEQ ID NOs: 29 and 30, and KOD-Plus-, PCR was carried out, E. coli JM109 was transformed, and the nucleotide sequence of the DNA encoding the amadoriase in the plasmid DNA harbored by the grown colonies was determined under the conditions described above. As a result, a recombinant plasmid (pKK223-3-CFP-H39) encoding a modified amadoriase (SEQ ID NO: 17) in which arginine at position 64 of the amino acid sequence of SEQ ID NO: 14 is substituted with glycine and leucine at position 110 is substituted with tyrosine was obtained.

Next, using the recombinant plasmid pKK223-3-CFP-T7-H39 as the template, oligonucleotides of SEQ ID NOs: 31 and 32, and KOD-Plus-, PCR was carried out, E. coli JM109 was transformed, and the nucleotide sequence of the DNA encoding the amadoriase in the plasmid DNA harbored by the grown colonies was determined under the conditions described above. As a result, a recombinant plasmid (pKK223-3-CFP-H40) encoding a modified amadoriase (SEQ ID NO: 18) in which arginine at position 64 of the amino acid sequence of SEQ ID NO: 14 is substituted with glycine, leucine at position 110 is substituted with tyrosine, and histidine at position 99 is substituted with serine was obtained.

Next, using the recombinant plasmid pKK223-3-CFP-H38 as the template, oligonucleotides of SEQ ID NOs: 33 and 34, and KOD-Plus-, PCR was carried out, E. coli JM109 was transformed, and the nucleotide sequence of the DNA encoding the amadoriase in the plasmid DNA harbored by the grown colonies was determined under the conditions described above. As a result, a recombinant plasmid (pKK223-3-CFP-H38-dh1) encoding a modified amadoriase in which arginine at position 64 of the amino acid sequence of SEQ ID NO: 14 is substituted with glycine and phenylalanine at position 269 is substituted with methionine was obtained.

Next, using the recombinant plasmid pKK223-3-CFP-H38 as the template, oligonucleotides of SEQ ID NOs: 35 and 33, and KOD-Plus-, PCR was carried out, E. coli JM109 was transformed, and the nucleotide sequence of the DNA encoding the amadoriase in the plasmid DNA harbored by the grown colonies was determined under the conditions described above. As a result, a recombinant plasmid (pKK223-3-CFP-H38-dh2) encoding a modified amadoriase in which arginine at position 64 of the amino acid sequence of SEQ ID NO: 14 is substituted with glycine and phenylalanine at position 269 is substituted with leucine was obtained.

Next, using the recombinant plasmid pKK223-3-CFP-H38 as the template, oligonucleotides of SEQ ID NOs: 36 and 37, and KOD-Plus-, PCR was carried out, E. coli JM109 was transformed, and the nucleotide sequence of the DNA encoding the amadoriase in the plasmid DNA harbored by the grown colonies was determined under the conditions described above. As a result, a recombinant plasmid (pKK223-3-CFP-H38-dh3) encoding a modified amadoriase in which arginine at position 64 of the amino acid sequence of SEQ ID NO: 14 is substituted with glycine and cysteine at position 280 is substituted with glutamine was obtained.

Next, using the recombinant plasmid pKK223-3-CFP-H40 as the template, oligonucleotides of SEQ ID NOs: 33 and 34, and KOD-Plus-, PCR was carried out, *E. coli* JM109 was transformed, and the nucleotide sequence of the DNA encoding the amadoriase in the plasmid DNA harbored by the grown colonies was determined under the conditions described above. As a result, a recombinant plasmid (pKK223-3-CFP-H40-dh1) encoding a modified amadoriase in which arginine at position 64 of the amino acid sequence of SEQ ID NO: 14 is substituted with glycine, leucine at position 110 is substituted with tyrosine, histidine at position 99 is substituted with serine, and phenylalanine at position 269 is substituted with methionine was obtained.

Next, using the recombinant plasmid pKK223-3-CFP-H40 as the template, oligonucleotides of SEQ ID NOs: 35 and 33, and KOD-Plus-, PCR was carried out, *E. coli* JM109 was transformed, and the nucleotide sequence of the DNA encoding the amadoriase in the plasmid DNA harbored by the grown colonies was determined under the conditions described above. As a result, a recombinant plasmid (pKK223-3-CFP-H40-dh2) encoding a modified amadoriase in which arginine at position 64 of the amino acid sequence of SEQ ID NO: 14 is substituted with glycine, leucine at position 110 is substituted with tyrosine, histidine at position 99 is substituted with serine, and phenylalanine at position 269 is substituted with leucine was obtained.

Next, using the recombinant plasmid pKK223-3-CFP-H40 as the template, oligonucleotides of SEQ ID NOs: 36 and 37, and KOD-Plus-, PCR was carried out, *E. coli* JM109 was transformed, and the nucleotide sequence of the DNA encoding the amadoriase in the plasmid DNA harbored by the grown colonies was determined under the conditions described above. As a result, a recombinant plasmid (pKK223-3-CFP-H40-dh3) encoding a modified amadoriase in which arginine at position 64 of the amino acid sequence of SEQ ID NO: 14 is substituted with glycine, leucine at position 110 is substituted with tyrosine, histidine at position 99 is substituted with serine, and cysteine at position 280 is substituted with glutamine was obtained.

Next, using the recombinant plasmid pKK223-3-CFP-H40-dh3 as the template, oligonucleotides of SEQ ID NOs: 33 and 34, and KOD-Plus-, PCR was carried out, *E. coli* JM109 was transformed, and the nucleotide sequence of the DNA encoding the amadoriase in the plasmid DNA harbored by the grown colonies was determined under the conditions described above. As a result, a recombinant plasmid (pKK223-3-CFP-H40-dh4) encoding a modified amadoriase in which arginine at position 64 of the amino acid sequence of SEQ ID NO: 14 is substituted with glycine, leucine at position 110 is substituted with tyrosine, histidine at position 99 is substituted with serine, phenylalanine at position 269 is substituted with methionine, and cysteine at position 280 is substituted with glutamine was obtained.

(3) Production of Various Types of Modified Amadoriases

Strains of *E. coli* JM109 harboring the recombinant plasmids obtained in the manner described above were cultured in 4 ml of LB-amp media supplemented with 0.1 mM IPTG at 25° C. for 16 hours. Thereafter, the resulting cultured strains were suspended in a 10 mM phosphate buffer (pH 7.5), the strains were ultrasonically disintegrated, and the resultants were centrifuged at 15,000 rpm for 10 minutes to prepare 0.5 ml each of crude enzyme solutions.

(4) Evaluation of Oxidase Activity and Dehydrogenase Activity of Various Types of Modified Amadoriases The crude enzyme solutions thus prepared were designated as samples, and, with the use of αF6P as a substrate, oxidase activity and dehydrogenase activity of various types of modified amadoriases were evaluated in accordance with the method for measurement of oxidase activity and the method for measurement of dehydrogenase activity described below.

(Method for Measurement of Oxidase Activity Using αF6P as the Substrate)
Preparation of Reagents
(Reagent 1): 0.1M phosphate buffer (pH 6.5) containing 5 U/ml peroxidase (manufactured by Kikkoman Corporation) and 0.49 mM 4-aminoantipyrine (manufactured by Wako Pure Chemical Industries, Ltd.)
(Reagent 2): 15 mM TOOS (manufactured by Dojindo Laboratories) solution
(Reagent 3): 30 mM αF6P (manufactured by Peptide Institute, Inc.) solution (final concentration: 1 mM)

Reagent 1 (675 μl), 25 μl of Reagent 2, and 25 μl of an enzyme solution are mixed, and the mixture is preliminarily heated at 37° C. for 5 minutes. Subsequently, 25 μl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute (ΔAs) at 555 nm. A control solution is prepared in the manner described above, except that 25 μl of ion-exchange water is added instead of 25 μl of Reagent 3, and the change in absorbance per minute (ΔA0) at 555 nm thereof is determined. The amount of an enzyme (enzyme activity) capable of generating 1 μmol of hydrogen peroxide per minute is defined as 1 U, when measurement is carried out using αF6P as the substrate at the final concentration of 1 mM. The oxidase activity (U/ml) is calculated using the equation shown below.

$$\text{Oxidase activity (U/ml)} = \{(\Delta As - \Delta A0) \times 0.75 \times df\} / (39.2 \times 0.5 \times 0.025)$$

ΔAs: the change in absorbance of the reaction solution per minute
ΔA0: the change in absorbance of the control solution per minute
39.2: the millimole absorbance index of quinoneimine dye generated by the reaction (mM$^{-1}$·cm$^{-1}$)
0.5: the number of moles of quinoneimine dye generated by 1 mol of hydrogen peroxide
df: the dilution factor (Method for Measurement of Dehydrogenase Activity Using αF6P as the Substrate)
Preparation of Reagents
(Reagent 3): 30 mM αF6P (manufactured by Peptide Institute, Inc.) solution (final concentration: 1 mM)
(Reagent 4): 0.25 M phosphate buffer (pH 6.5)
(Reagent 5): 10 mM WST-3 (manufactured by Dojindo Laboratories) solution
(Reagent 6): 5.4 mM mPMS (manufactured by Dojindo Laboratories) solution Reagent 4 (270 μl), Reagent 5 (150 μl), Reagent 6 (25 μl), ion-exchange water (255 μl), and an enzyme solution (25 μl) are mixed, and the mixture is preliminarily heated at 37° C. for 5 minutes. Subsequently, 25 μl of Reagent 3 is added, the resultant is thoroughly mixed, and the absorbance at 433 nm is then measured using a spectrophotometer (U-3010, manufactured by Hitachi High-Technologies). A control solution is prepared in the manner described above, except that 25 μl of ion-exchange water is added instead of 25 μl of the enzyme solution. The amount of an enzyme capable of generating 1 μmol of formazan dye per minute is defined as 1 U, when measurement is carried out using αF6P as the substrate at the final concentration of 1 mM. Dehydrogenase activity (U/ml) is calculated using the equation shown below.

$$\text{Dehydrogenase activity (U/ml)} = \{(\Delta As - \Delta A0) \times 0.75 \times df\}/(31 \times 0.025)$$

ΔAs: the change in absorbance of the reaction solution per minute

ΔA₀: the change in absorbance of the control solution per minute

31: the millimole absorbance index of the formazan dye of WST-3 generated by the reaction (mM$^{-1}$·cm$^{-1}$)

df: the dilution factor

The results are shown in Table 8 and Table 9. In Table 8, "CFP-H38" indicates an amadoriase derived from the strain of *E. coli* JM109 (pKK223-3-CFP-H38). In Table 9, "CFP-H40" indicates an amadoriase derived from the strain of *E. coli* JM109 (pKK223-3-CFP-H40). In this example, CFP-T7-H37, which is an amadoriase derived from the strain of *E. coli* JM109 (pKK223-3-CFP-T7-H37), is employed as the original enzyme for mutation. Therefore, descriptions concerning "Amino acid mutations" in the table do not include various points of mutations that have already been introduced into CFP-T7-H37. In the table, oxidase activity (%) and dehydrogenase activity (%) are expressed in percentage terms relative to the oxidase activity (U/ml) of the original enzyme CFP-T7-H38 or CFP-T7-H40 designated to be 100. In the table, "OX/DH (%)" is expressed in percentage terms relative to the OX/DH ratio of the original enzyme CFP-T7-1-138 or CFP-T7-H40 designated to be 100.

TABLE 8

| Amadoriase | Amino acid mutation based on CFP-H37 (SEQ ID NO: 14) | Oxidase activity (%) | Dehydrogenase activity (%) | OX/DH | OX/DH (%) |
|---|---|---|---|---|---|
| CFP-H38 | R64G | 100 | 8.94 | 11.2 | 100 |
| CFP-H38-dh1 | R64G, F269M | 53.4 | 24.0 | 2.23 | 20.0 |
| CFP-H38-dh2 | R64G, F269L | 28.3 | 8.23 | 3.43 | 30.7 |
| CFP-H38-dh3 | R64G, C280Q | 1.0 | 3.22 | 0.30 | 2.7 |

TABLE 9

| Amadoriase | Amino acid mutation based on CFP-H37 (SEQ ID NO: 14) | Oxidase activity (%) | Dehydrogenase activity (%) | OX/DH | OX/DH (%) |
|---|---|---|---|---|---|
| CFP-H40 | R64G, H99S, L110Y | 100 | 16 | 6.2 | 100 |
| CFP-H40-dh1 | R64G, H99S, L110Y, F269M | 21 | 16 | 1.3 | 21 |
| CFP-H40-dh2 | R64G, H99S, L110Y, F269L | 7.5 | 5.4 | 1.4 | 23 |
| CFP-H40-dh3 | R64G, H99S, L110Y, C280Q | 13 | 29 | 0.45 | 7.3 |
| CFP-H40-dh4 | R64G, H99S, L110Y, F269M, C280Q | 1.9 | 5.4 | 0.35 | 5.7 |

As shown in Table 8, each of the mutations F269M, F269L, and C280Q reduced (lowered) the ratio of oxidase activity to dehydrogenase activity (OX/DH) of the modified enzymes, relative to CFP-H38.

As shown in Table 9, each of the mutations F269M, F269L, and C280Q reduced the ratio of oxidase activity to dehydrogenase activity (OX/DH) of the modified enzymes, relative to CFP-H40. In addition, the F269M/C280Q double mutant produced from CFP-H40 was found to have a further lowered ratio of oxidase activity to dehydrogenase activity (OX/DH).

Example 2

(Production and Purification of CFP-H38-Dh3)

Strains of *E. coli* JM109 (CFP-H38-dh3) were inoculated into 200 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 40 ml of a crude enzyme solution.

After the column loaded with Q-sepharose FF (GE Healthcare) was equilibrated with a 10 mM potassium phosphate buffer (pH 7.5), the crude enzyme solution containing CFP-H38-dh3 was applied, so as to allow amadoriases to bind to the anion-exchange resin. Thereafter, a 10 mM potassium phosphate buffer (pH 7.5) containing 30 mM NaCl was applied in an amount equivalent to 20 column volumes, so as to elute contaminating proteins, the proteins bound to the resin were eluted with the aid of a 10 mM potassium phosphate buffer (pH 7.5) containing 80 mM NaCl, and fractions having amadoriase activity were then collected.

Each of the obtained fractions having amadoriase activity were concentrated using Amicon Ultra Ultracel-30K (Millipore) and purified using HiLoad 26/60 Superdex 200. Resin equilibration and elution were carried out using a 10 mM potassium phosphate buffer (pH 6.5) containing 150 mM NaCl. Purity of the eluted fractions was evaluated via SDS-PAGE, fractions containing no contaminating proteins were collected, and the collected fractions were designated as purified samples of CFP-H38-dh3.

Example 3

(Evaluation of Dehydrogenase Activity of CFP-H38-Dh3 on HbA1c)

With the use of a spectrophotometer (U-3010, manufactured by Hitachi High-Technologies), dehydrogenase activity of CFP-H38-dh3 on HbA1c was evaluated in the manner described below.

(Reagent 7): 1.84 mg/ml HbA1c solution (manufactured by BBI solution)

(Reagent 8): 10% n-dodecyl-β-D-maltoside (manufactured by Dojindo Laboratories)

(Reagent 9): 185 mM phosphate buffer (pH 6.0)

(Reagent 5): 10 mM WST-3 solution (Reagent 10): 8.8 mg/ml (4.1 U/ml) CFP-H38-dh3 solution (U represents dehydrogenase activity relative to 1 mM αF6P as the substrate)

(Reagent 11): 8.8 mg/ml of CFP-T7 solution

First, Reagent 7 (540 μl) was mixed with Reagent 8 (60 μl), and then the mixture was heated at 98° C. for 5 minutes to prepare an HbA1c sample pre-treatment solution. Subsequently, Reagent 5 (125 μl), Reagent 10 (62.5 μl), and ion-exchange water (7.5 μl) were mixed with Reagent 9 (305 μl), and the mixture was pre-heated at 37° C. for 5 minutes. Subsequently, the HbA1c sample pre-treatment solution (125 μl) was mixed therewith, the mixture was agitated, and the absorbance at 433 nm was then measured using a spectrophotometer. A control experiment was performed with the addition of 62.5 μl of Reagent 11 instead of 62.5 μl of Reagent 10. CFP-T7 is an amadoriase that does not react with αF6P or HbA1c (see WO 2015/060429).

Figure 4:
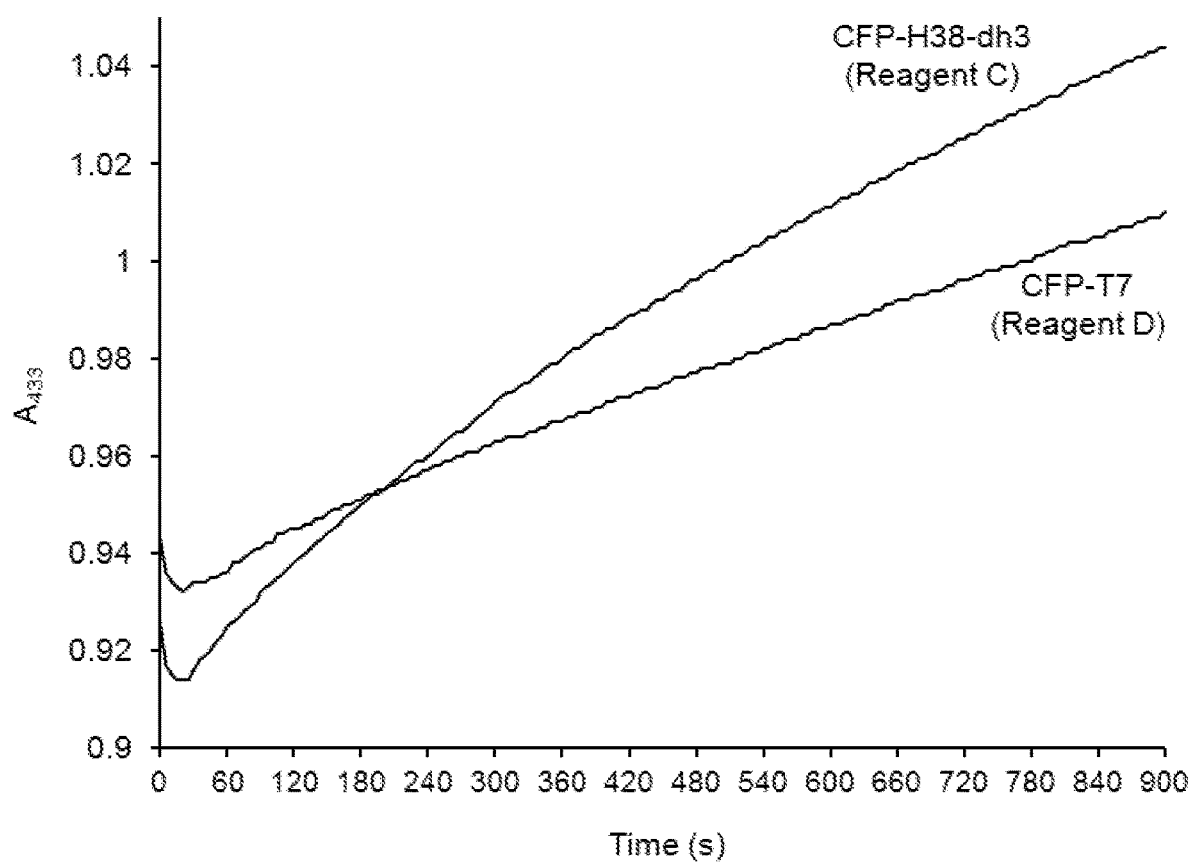

The results are shown in FIG. 4. With the use of A1cDH according to the present invention, a significant increase was observed in the absorbance, compared with the control. That is, it was confirmed that CFP-H38-dh3 exhibited dehydrogenase activity on HbA1c.

Example 4

(Quantification of HbA1c Using a Printed Electrode)

Figure 5:
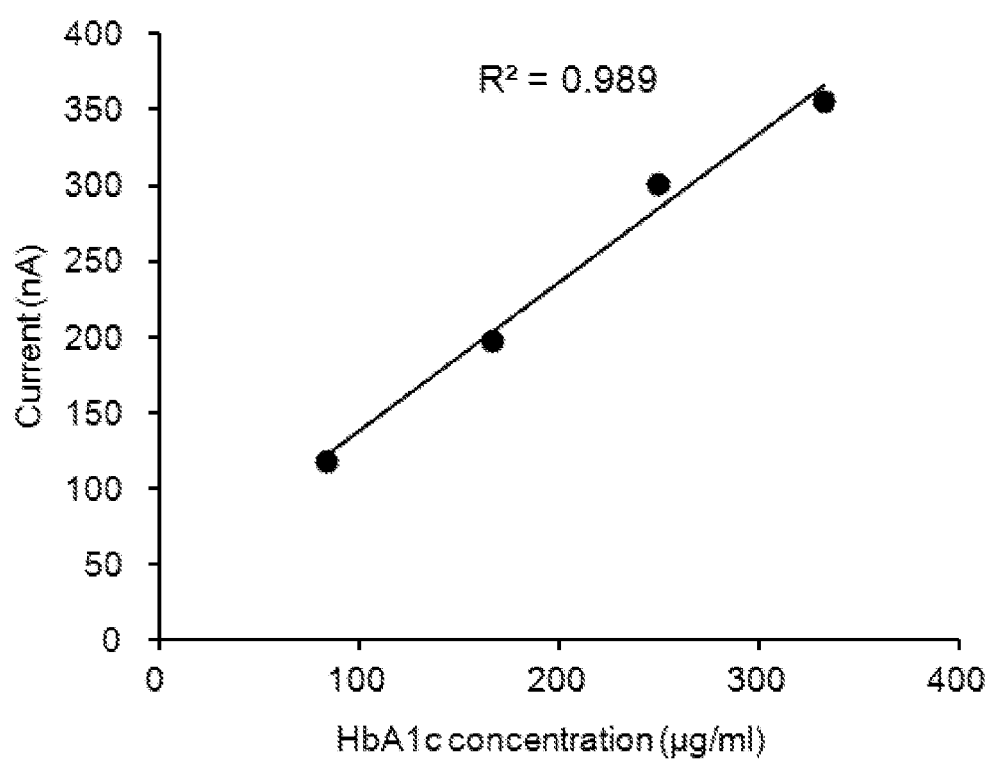

First, with the use of the HbA1c sample pre-treatment solution prepared in Example 3, an HbA1c solution containing 20 mM phosphate buffer (pH 6.5), 1 M KCl, and 0.65% n-dodecyl-β-D-maltoside was prepared. HbA1c concentration was adjusted to the 4 levels of 83, 166, 249, and 332 μg/ml. The prepared solution of HbA1c (10 μl) and 4 μl of 500 mM RuCl$_3$ (manufactured by Tokyo Chemical Industry Co., Ltd.) were mixed on the screen-printed carbon electrodes (DRP-110, manufactured by DropSens). The screen-printed carbon electrode was connected to the ALS electrochemical analyzer (814D, manufactured by BAS) with the aid of a cable connector (CAC, manufactured by DropSens), and then 6 μl of 38.4 mg/ml (17.8 U/ml) CFP-H38-dh3 solution was applied to the electrodes, the reaction was allowed to proceed with the application of the voltage of +200 mV (vs. Ag/AgCl), and the current level was measured 60 seconds later. FIG. 5 shows the results of plotting of the current responses at relevant cHbA1c concentrations.

As shown in FIG. 5, HbA1c was quantified with high accuracy using CFP-H38-dh3.

All publications, patents, and patent applications cited herein are incorporated herein by reference in their entirety.

BRIEF DESCRIPTION OF SEQUENCES

SEQ ID NO: 1: the amadoriase derived from the genus *Coniochaeta* (CFP-T7)
SEQ ID NO: 2: the gene sequence of CFP-T7
SEQ ID NO: 3: the amadoriase derived from *Eupenicillium terrenum*
SEQ ID NO: 4: the ketoamine oxidase derived from *Pyrenochaeta* sp.
SEQ ID NO: 5: the ketoamine oxidase derived from *Arthrinium* sp.
SEQ ID NO: 6: the ketoamine oxidase derived from *Curvularia clavata*
SEQ ID NO: 7: the ketoamine oxidase derived from *Neocosmospora vasinfecta*
SEQ ID NO: 8: the fructosyl amino acid oxidase derived from *Cryptococcus neoformans*
SEQ ID NO: 9: the fructosyl peptide oxidase derived from *Phaeosphaeria nodorum*
SEQ ID NO: 10: the fructosyl amino acid oxidase derived from *Aspergillus nidulans*
SEQ ID NO: 11: the fructosyl peptide oxidase derived from *Emericella nidulans*
SEQ ID NO: 12: the fructosyl amino acid oxidase derived from *Ulocladium* sp.
SEQ ID NO: 13: the fructosyl amino acid oxidase derived from *Penicillium janthinellum*
SEQ ID NO: 14: the amino acid sequence of CFP-T7-R62D/L63H/E102K/D106K/Q110L/A113K/A355S/D68N/A356T (CFP-T7-H37)
SEQ ID NO: 15: the nucleotide sequence of CFP-T7-H37
SEQ ID NO: 16: the amino acid sequence of CFP-T7-H38 (CFP-T7-H37-R64G)
SEQ ID NO: 17: the amino acid sequence of CFP-T7-H39 (CFP-T7-H37-R64G/L110Y)
SEQ ID NO: 18: the amino acid sequence of CFP-T7-H40 (CFP-T7-H37-R64G/L110Y/H99S)
SEQ ID NO: 19: Ao2 (derived from *Aspergillus oryzae*; also designated FaoAo2)
SEQ ID NO: 20: Af2 (derived from *Aspergillus fumigatus*; also designated Amadoriase II)
SEQ ID NO: 21: At (derived from *Aspergillus terreus*; also designated FAOD-A)
SEQ ID NO: 22: Fo (derived from *Fusarium oxysporum*)
SEQ ID NO: 23: Ao1 (derived from *Aspergillus oryzae*; also designated FaoAo1)
SEQ ID NO: 24: Af1 (derived from *Aspergillus fumigatus*; also designated Amadoriase I)
SEQ ID NO: 25: Pi (derived from *Pichia* sp.)
SEQ ID NO: 26: Dh (derived from *Debaryomyces hansenii*)
SEQ ID NO: 27: primer sequence (for introduction of R64G)
SEQ ID NO: 28: primer sequence (for introduction of R64G)
SEQ ID NO: 29: primer sequence (for introduction of L110Y)
SEQ ID NO: 30: primer sequence (for introduction of L110Y)
SEQ ID NO: 31: primer sequence (for introduction of H99S)
SEQ ID NO: 32: primer sequence (for introduction of H99S)
SEQ ID NO: 33: primer sequence (for introduction of F269M)
SEQ ID NO: 34: primer sequence (for introduction of F269M)
SEQ ID NO: 35: primer sequence (for introduction of F269L)
SEQ ID NO: 36: primer sequence (for introduction of C280Q)
SEQ ID NO: 37: primer sequence (for introduction of C280Q)

All publications, patents, and patent applications cited herein are incorporated herein by reference in their entirety.

The invention claimed is:

1. A method for measurement of hemoglobin A1c in a sample comprising contacting an HbA1c dehydrogenase directly acting on hemoglobin A1c with hemoglobin A1c in a sample and measuring a reduced electron mediator that is not hydrogen peroxide generated by the action or an oxidized electron mediator that is not oxygen consumed by the action, wherein a protease is not applied to the sample, and wherein the measurement is solely based on measuring the dehydrogenase activity of the HbA1c dehydrogenase.

2. The method for measurement according to claim 1, wherein said measurement is an electrochemical measurement using an HbA1c dehydrogenase, an enzyme electrode comprising HbA1c dehydrogenase or an enzyme sensor comprising, as a working electrode, said enzyme electrode, and an electron mediator that is not oxygen or wherein said measurement is an absorbance measurement using HbA1c dehydrogenase, a colorimetric substrate, and an electron mediator that is not oxygen.

* * * * *